(12) United States Patent
Shyur et al.

(10) Patent No.: US 8,492,131 B2
(45) Date of Patent: Jul. 23, 2013

(54) FUNGAL LACCASES AND USES THEREOF

(75) Inventors: Lie-Fen Shyur, Taipei (TW); Chih-An Hsu, Taipei County (TW)

(73) Assignee: Academia Sinica, Taipei (TW)

( * ) Notice: Subject to any disclaimer, the term of this patent is extended or adjusted under 35 U.S.C. 154(b) by 511 days.

(21) Appl. No.: 12/777,569

(22) Filed: May 11, 2010

(65) Prior Publication Data

US 2011/0281323 A1 Nov. 17, 2011

(51) Int. Cl.
*C12N 9/02* (2006.01)
*C07K 14/00* (2006.01)
*C12P 21/00* (2006.01)

(52) U.S. Cl.
USPC ............................ 435/189; 435/69.1; 530/350

(58) Field of Classification Search
USPC .................................. 435/189, 69.1; 530/350
See application file for complete search history.

(56) References Cited

FOREIGN PATENT DOCUMENTS

JP     2006-158252     6/2006

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Khammuang et al., "Laccase From Spent Mushroom Compost of *Lentinus polychrous* Lev, and its Potential for Remazol Brilliant Blue R Decolourisation," Biotechnology 6(3):408-413 (2007).
D'Annibale et al., "Substrate Specificity of Laccase from *Lentinus edodes*," Acta Biotechnol. 16(4):257-270 (1996).

* cited by examiner

*Primary Examiner* — Delia Ramirez
(74) *Attorney, Agent, or Firm* — Occhiuti Rohlicek & Tsao LLP

(57) ABSTRACT

Novel laccases from *Cerrena* sp. WR1 and *Lentinus* sp. and uses thereof.

7 Claims, 13 Drawing Sheets

A.

B.

C.

D.

A.

B.

A.

B.

C.

A

B

US 8,492,131 B2

FUNGAL LACCASES AND USES THEREOF

BACKGROUND OF THE INVENTION

Laccases (benzenebiol:oxygen oxidoreductase; EC 1.10.3.2) are multi-copper-containing oxidases found in various organisms, e.g., insect, plant, and fungi.

They catalyze oxidation of a broad range of compounds, e.g., diphenol, polyphenol, diamine, and aromatic amine. Many of these compounds are important raw materials for making various industrial products. Others are toxic components contained in industrial wastes.

Laccases have great potential in industrial applications, such as biopulping, biobleaching, food processing, bioremediation, and wastewater treatment.

SUMMARY OF THE INVENTION

The present invention is based on an unexpected discovery that six novel laccases, three from *Cerrena* sp. WR1 (i.e., Lcc1, Lcc2, and Lcc3) and the other three from *Lentinus* sp. (LccA, LccB, and LccC), exhibit high laccase activity.

Accordingly, one aspect of this invention features an isolated polypeptide containing an amino acid sequence at least 85% (e.g., 90%, 95%, or 98%) identical to one of SEQ ID NOs:1-6, referring to mature laccases Lcc1, Lcc2, Lcc3, LccA, LccB, and LccC, respectively. In one example, the isolated polypeptide has the amino acid sequence of one of SEQ ID NOs:7-12, referring to precursor (i.e., including an N-terminal signal peptide) Lcc1, Lcc2, Lcc3, LccA, LccB, and LccC, respectively.

Another aspect of the invention features an isolated nucleic acid (e.g., an expression vector) containing a nucleotide sequence coding for one of the laccases mentioned above. In one example, the nucleotide sequence is one of SEQ ID NOs:13-18, coding for SEQ ID NOs:1-6, respectively. In another example, it is one of SEQ ID NOs:19-24, coding for SEQ ID NOs:7-12, respectively. Preferably, the nucleotide sequence is in operative linkage with a suitable promoter for expressing the encoded polypeptide in a host cell.

The terms "isolated polypeptide" and "isolated nucleic acid" used herein respectively refer to a polypeptide and a nucleic acid substantially free from naturally associated molecules. A preparation containing the polypeptide or nucleic acid is deemed as "an isolated polypeptide" or "an isolated nucleic acid" when the naturally associated molecules in the preparation constitute at most 20% by dry weight. Purity can be measured by any appropriate method, e.g., column chromatography, polyacrylamide gel electrophoresis, and HPLC.

Also within the scope of this invention is a method of oxidizing a laccase substrate (i.e., a compound that can be oxidized by a laccase) by contacting one of the laccases mentioned above with the substrate. In one example, the substrate is hardwood stem, softwood stem, nut shell, corn cob, paper (e.g., newspaper or waste paper from chemical pulps), straw (e.g., straw from rice, wheat, barley, oat, or rye), sorted refuse, leaf, cotton seeds hair, swine waste, cattle manure, grass (e.g., switch grass, Coastal Bermuda grass, S32 rye grass, Grass Esparto, Grass Sabai, Grass Elephant), sugar cane bagasse, bamboo, fiber (e.g., Bast fiber Seed flax, Bast fiber Kenaf, Bast fiber Jute, Leaf fiber Abaca, Leaf fiber Sisal, or Leaf fiber Henequen), coffee pulp, banana waste, and yucca waste. In another example, the substrate is an aromatic dye, such as a polyphenol-containing dye.

The details of one or more embodiments of the invention are set forth in the description below. Other features or advantages of the present invention will be apparent from the following drawings and detailed description of two examples, and also from the appended claims.

BRIEF DESCRIPTION OF THE DRAWINGS

The drawings are first described.

DETAILED DESCRIPTION OF THE INVENTION

Figure 1:
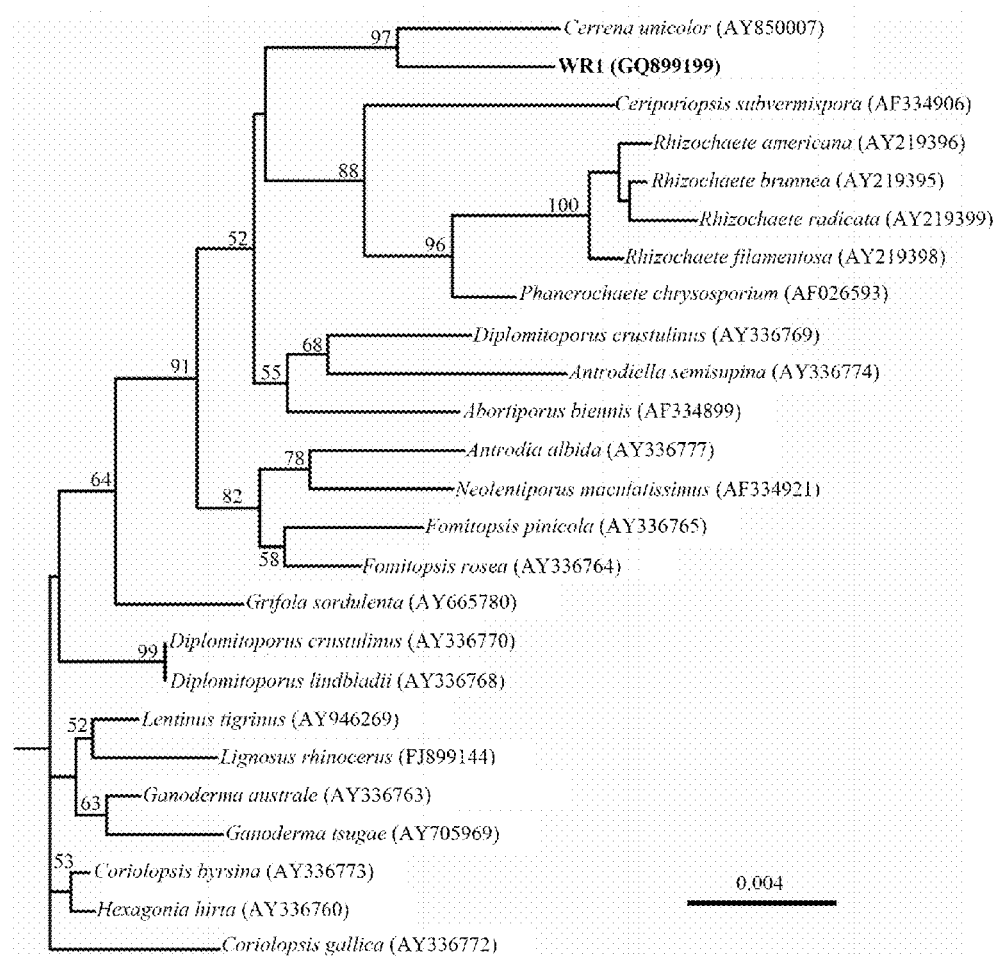
FIG. 1 is a diagram showing the phylogenetic relationship between *Cerrena* sp. WR1 and other fungal strains. Bootstrap values at nodes refer to the percentage of 500 replicates. Scale bar: base substitutions per 100 bases.

Described below are laccases Lcc1, Lcc2, and Lcc3, isolated from *Cerrena* sp. WR1, and laccases LccA, LccB, and LccC, isolated from *Lentinus* sp. The amino acid sequences of these enzymes, in precursor form, and their coding sequences are shown below.

*Cerrena* sp. WR1 Lcc1 (GenBank accession no. GQ899201)

```
ATGCTTAACTTTAATTCGCTTTCCACCTTCGCAGTCCTTGCTTTGTCGATGCGCGCAAATGCCGCTATCGGTCCTGTCACTGACTTAGAA      30
 M  L  N  F  N  S  L  S  T  F  A  V  L  A  L  S  M  R  A  N  A  A  I  G  P  V  T  D  L  E

ATCACGAACGGCACCATCTCTCCCGATGGCTATTCTCGTGCAGCCGTCCTTGCTGGAGGCTCTTTCCCCGGCCCACTTATCACAGGAAAC      60
 I  T  N  G  T  I  S  P  D  G  Y  S  R  A  A  V  L  A  G  G  S  F  P  G  P  L  I  T  G  N

Cu²⁺ binding site-I
AAAAGTGACAACTTCCAAATCAACGTTGTGAACTCGTTGGCCGATTCCGACATGCTTAAGTCTACAACCGTTCACTGGCACGGTTTCTTC      90
 K  S  D  N  F  Q  I  N  V  V  N  S  L  A  D  S  D  M  L  K  S  T  T  V  H  W  H  G  F  F CAAAAGGGTACCAACTGGGCTGACGGCCCTGCTTTCGTCAACCAGTGTCCCATTGCGACGGGCAACTCTTTCTTTACAACTTCAACGCT      120
 Q  K  G  T  N  W  A  D  G  P  A  F  V  N  Q  C  P  I  A  T  G  N  S  F  L  Y  N  F  N  A Cu²⁺ binding site-I
ACGGACCAGGCTGGTACTTTCTGGTACCATTCTCACTTGGAGACTCAGTACTGTGATGGTCTTCGTGGCCCGATGGTTGTCTATGACCCA      150
 T  D  Q  A  G  T  F  W  Y  H  S  H  L  E  T  Q  Y  C  D  G  L  R  G  P  M  V  V  Y  D  P GACGATCCTCATGCTGACCTCTACGATGTCGACGACGATAGCACTGTCATTACTCTTGCCGATTGGTATCACACCCTTGCTCGACTTGGT      180
 D  D  P  H  A  D  L  Y  D  V  D  D  D  S  T  V  I  T  L  A  D  W  Y  N  T  L  A  R  L  G GCCCGCTTTCCCGACTTCGGACGTACTTTGATCAACGGTTTGGGCCGTTACAGCGATGGTAACACAACCGATCTCGCTGTCATTACTGTC      210
 A  A  F  P  T  S  D  A  T  L  I  N  G  L  G  R  Y  S  D  G  W  T  T  D  L  A  V  I  T  V GAATCCGGCAAGAGGTACCGATTCAGGCTGGTCAGCATTTCTTGCGATCCCAACTTCACTTTCTCCATCGACAACCACACCATGACAATC      240
 E  S  G  K  R  Y  R  F  R  L  V  S  I  S  C  D  P  N  F  T  F  S  I  D  W  H  T  M  T  I ATCGAGGCTGATGCTGTCAACTATACACCCCTCGATGTTGACGAGATTCAAATCTTCGCTGGTCAACGTTACTCCTTCATTCTCACTGCC      270
 I  E  A  D  A  V  N  Y  T  P  L  D  V  D  E  I  Q  I  F  A  G  Q  R  Y  S  F  I  L  T  A AACCAGACCGTCGACAACTACTCGATTCGTGCTGACCCCAACGTTGGTACGACTGGCTTCGACAATGGCATCAACTCCGCTATCCTTCGT      300
 N  Q  T  V  D  N  Y  W  I  R  A  D  P  N  V  G  T  T  G  F  D  N  G  I  N  S  A  I  L  R TACAGCGGTGCCGACGAGGTCGAGCCTACCACCAACCAGACCACCAGTACTAACCCTCTTGTTGAGGCTAACTTGGTTCCTCTCGATGGT      330
 Y  S  G  A  D  E  V  E  P  T  T  N  Q  T  T  S  T  N  P  L  V  E  A  N  L  V  P  L  D  G GCTGCTGCTCCCGGTGAAGCTGTCGCTGGAGGTGTTGACTATGCGCTGAACTTGGCTCTCGCTTTCGACGGTACAAACCTCGATTTCACC      360
 A  A  A  P  G  E  A  V  A  G  G  V  D  Y  A  L  N  L  A  L  A  F  D  G  T  N  L  D  F  T GTCAACGGTTACGAGTACACCTCTCCTACCGTCCCAGTCCTACTCCAAATTCTCAGCGGTGCCTCTTCCGTCGACGACTTGCTCCCCAGT      390
 V  N  G  Y  E  Y  T  S  P  T  V  P  V  L  L  Q  I  L  S  G  A  S  S  V  D  D  L  L  P  S Cu²⁺ binding site-III
GGAAGCATTTACTCACTGCCAAGCAACTCCACTATCGAGCTCAGTATTCCCGCACTTGCCGTCGGTGCTCCCCACCCTATCCATTTGCAC      420
 G  S  I  Y  S  L  P  S  N  S  T  I  E  L  S  I  P  A  L  A  V  G  A  P  H  P  I  H  L  H GGTCACACTTTCTCTGTCGTTCGTAGTGCCGGATCCACCACCTACAACTACGACAACCCCCCTCGTCGTGACGTCGTCAGCATTGGTACC      450
 G  H  T  F  S  V  V  R  S  A  G  S  T  T  Y  N  Y  D  N  P  P  R  R  D  V  V  S  I  G  T Cu²⁺ binding site-IV
GCCACTGATGATAACGTTACCATTCGTTTCACCACCGACAACCCGGGACCTTGGTTCCTCCACTGTCACATTGACTTCCACTTGGAAGCT      480
 A  T  D  D  N  V  T  I  R  F  T  T  D  N  P  G  P  W  F  L  H  C  H  I  D  F  H  L  E  A GGTTTCGCAGTCGTCTTTGCTGAAGACTTTAATGACACTGCTTCTGCTAACACTGTCACCACTGAATGGAGCGACCTCTGCACTACCTAC      510
 G  F  A  V  V  F  A  E  D  F  N  D  T  A  S  A  N  T  V  T  T  E  W  S  D  L  C  T  T  Y GATGCCCTCTCCTCCGATGACCTCTAA (SEQ ID NO: 19)                                                  518
 D  A  L  S  S  D  D  L  *  (SEQ ID NO: 7)
```

*Cerrena* sp. WR1 LCC2 (GenBank accession no. GQ899202)

```
ATGATTAACTTTAATTCGTTACTTACTTTCACAGTCCTAGCACTGTCGATGCGCGCACATGCCGCTATCGGTCCCGTCACTGACCTCACA      30
 M  I  N  F  N  S  L  L  T  F  T  V  L  A  L  S  M  R  A  H  A  A  I  G  P  V  T  D  L  T

ATCACTAATGCCACCATTTCCCCGGATGGTTTCTCTCGTCAAGCCGTGCTTGCTGGAGGTGTTTTCCCTGGTCCGCTTATTACCGGAAAC      60
 I  T  N  A  T  I  S  P  D  G  F  S  R  Q  A  V  L  A  G  G  V  F  P  G  P  L  I  T  G  N

Cu²⁺ binding site-I
AAGGGGCGACAACTTCCAAATCAATGTTGTTAATTCATTGGAAAACTCTGACATGCTTAAGTCTACGACCATTCACTGCACGGTTTCTTC      90
 K  G  D  N  F  Q  I  N  V  V  N  S  L  E  N  S  D  M  L  K  S  T  T  I  H  W  H  G  F  F CAGAAGGGTACCAACTGGGCCGATGGTCCTGCCTTCGTTAACCAATGCCCAATCGCCACGGGCAACTCTTTCCTGTACAACTTCAACGCA      120
 Q  K  G  T  N  W  A  D  G  P  A  F  V  N  Q  C  P  I  A  T  G  N  S  F  L  Y  N  F  N  A Cu²⁺ binding site-II
GACGACCAGGCTGGTACATTCTGGTACCACTCTCACTTGTCTACTCAATATTGCGATGGTCTCCGAGGCCCTATGGTCGTCTACGACCCG      150
 D  D  Q  A  G  T  F  W  Y  H  S  H  L  S  T  Q  Y  C  D  G  L  R  G  P  M  V  V  Y  D  P AACGATCCTCACGCTTCCCTCTACGATGTTGATGATGAGAGCACTGTGATTACCCTCGCCGATTGGTACCACACCCTTGCCCGACTTGGT      180
 N  D  P  H  A  S  L  Y  D  V  D  D  E  S  T  V  I  T  L  A  D  W  Y  H  T  L  A  R  L  G GCAGCCTTTCCCGACTGCGGATGCTACCCTCATTAACGGCTTGGGTCGTTACAGCGATGGTACTTCGGACCTTGTGATCACCGTT      210
 A  A  F  P  T  A  D  A  T  L  I  N  G  L  G  R  Y  S  D  G  T  S  D  L  A  V  I  T  V GAGTCCGGAAAGAGGTACCGATTCCGATTGGTCAACATTTCTTGCGACCCCAACTACACTTTCTCTATCGACAACCACACATTCACCGTC      240
 E  S  G  K  R  Y  R  F  R  L  V  N  I  S  C  D  P  N  Y  T  F  S  I  D  N  H  T  F  T  V ATTGAGGTCGATGGTGTCAACCACGCGGCGCTTGATGTCGATGAAATCCAGATCTTCGCTGGTCAACGTTACTCCTTTGTTCTCACTGCT      270
 I  E  V  D  G  V  N  H  A  A  L  D  V  D  E  I  Q  I  F  A  G  Q  R  Y  S  F  V  L  T  A AACCAAACCGTCGACAACTACTGGATCCGTGCAAACCCCAATCTCGGAACCACCGGCTTCGACAACGGCATCAACTCCGCTATCCTTCGT      300
 N  Q  T  V  D  N  Y  W  I  R  A  N  P  N  L  G  T  T  G  F  D  N  G  I  N  S  A  I  L  R
```

```
                    N  Q  T  V  D  N  Y  W  I  R  A  N  P  N  L  G  T  T  G  F  D  N  G  I  N  S  A  I  L  R
TACAGCGGTGCTAACGAGACTGAACCCACCACCACCCAGACCACCGCTACTGCTGCTCTCAGCGAAGCTAGCTCGTTCCTCTCGAGGAC              330
 Y  S  G  A  N  E  T  E  P  T  T  T  Q  T  T  A  T  A  A  L  S  E  A  S  L  V  P  L  E  D
CCTGCTGCTCCTGGTGAGGCCGTTGCCGGAGGTGTCGATTATGCTTTGAACTTGGCATTCGCTTCGACGGTGCCAACCTTGACTTCACA              360
 P  A  A  P  G  E  A  V  A  G  G  V  D  Y  A  L  N  L  A  F  A  F  D  G  A  N  L  D  F  T
GTCAACGGTGAAACCTACGTCTCCCCTACCGTCCCCGTCCTCCTCCAAATTCTTAGCGGTGCTTCCTCGTCTCTGACTTGCTCCCTGCC              390
 V  N  G  E  T  Y  V  S  P  T  V  P  V  L  L  Q  I  L  S  G  A  S  S  V  S  D  L  L  P  A

Cu²⁺ binding site-III
GGAAGCGTCTACTCCTTGCCCAGCAACTCCACCATCGAGCTCAGCATGCCTGGAGGTGTCGTCGGTGGTGGTCACCCCCTTCACTTGCAC              420
 G  S  V  Y  S  L  P  S  N  S  T  I  E  L  S  M  P  G  G  V  V  G  G  G  H  P  L  H  L  H GGTCACGCCTTCTCCGTTGTTCGTAGTGCCGGCTCTGACACTTACAACTACGTCAACCCCCCTCGCCGTGATGTTGTCAACATTGGTGCT              450
 H  A  F  S  V  V  R  S  A  G  S  D  T  Y  N  Y  V  N  P  P  R  R  D  V  V  N  I  G  A Cu²⁺ binding site-IV
GCTGGTGACAACGTCACTATCCGTTTCACCACTGACAACCCCGGACCCTGGTTCCTCCACTGCCACATCGATTTCCACTTGGAAGCTGGC              480
 A  G  D  N  V  T  I  R  F  T  T  D  N  P  G  P  W  F  L  H  C  H  I  D  F  H  L  E  A  G
TTCGCTGTCGTCTTTGCTGAGGACTTCAACGCCACCGCTTCTTCTAACACCGTCACCACTGAGTGGAGCAACCTTTGCACCACCTACGAC              510
 F  A  V  V  F  A  E  D  F  N  A  T  A  S  S  N  T  V  T  T  E  W  S  N  L  C  T  T  Y  D
GCCCTCTCTGCCGACGATCAGTAA (SEQ ID NO: 20)                                                                 517
 A  L  S  A  D  D  Q  *  (SEQ ID NO: 8)
Cerrena sp. WR1 Lcc3 (GenBank accesstion no. GQ899203)

ATGGCCTTCCGAACCGGGTTTTCCGCTTTCATCTCTCTCAGCCTTGCCCTTGGTGCACTCGCTGCTATCGGTCCTGTTGCTGACCTTCAC              30
 M  A  F  R  T  G  F  S  A  F  I  S  L  S  L  A  L  G  A  L  A  A  I  G  P  V  A  D  L  H
ATCACGGATGCGAACGTTTCTCCTGATGGCTTCACTCGACCTGCTGTCCTTGCTGGTGGCACCTTCCCCGGCCCTCTCATTACGGGAAAG              60
 I  T  D  A  N  V  S  P  D  G  F  T  R  P  A  V  L  A  G  G  T  F  P  G  P  L  I  T  G  K
CAGGGTGACAACTTCCAGATCAATGTCATCGACGAACTCACGGACGCGACTATGTTGAAGTCTACGTCTATTCATTGGCACGGTATCTTC              90
 Q  G  D  N  F  Q  I  N  V  I  D  E  L  T  D  A  T  M  L  K  S  T  S  I  H  W  H  G  I  R
CAGAAAGGCACCAACTGGGCTGACGGCCCCTCCTTCGTCAATCAGTGCCCCATCACTACAGGAAACTCGTTCCTGTACGACTTTTCTGTC              120
 Q  K  G  T  N  W  A  D  G  P  S  F  V  N  Q  C  P  I  T  T  G  N  S  F  L  Y  D  F  S  V

Cu²⁺ binding site-II
CCCGACCAGACCGGGACGTACTGGTATCACAGTCATTATCACCCAGTACTGTGACGGTTTGCGAGGAGCCCTTGTCATTTACGACGAC              150
 P  D  Q  T  G  T  Y  W  Y  H  S  H  L  S  T  Q  Y  C  D  G  L  R  G  A  L  V  I  Y  D  D
AATGATCCTCACAAGGATCTCTATGATGTTGATGATGAGACTACCGTCATCACCCTCGCCGACTGGTATCATACCCAGGCTCGCCTGATC              180
 N  D  P  H  K  D  L  Y  D  V  D  D  E  T  T  V  I  T  L  A  D  W  Y  H  T  Q  A  R  L  I
ACTGGTGTCCCTGTCTCCGATGCGACTCTGATCAACGGTCTTGGCCGTTATCTTAATGGCCCAACCGATGCTCCGCTCGCTGTTATCACT              210
 T  G  V  P  V  S  D  A  T  L  I  N  G  L  G  R  Y  L  N  G  P  T  D  A  P  L  A  V  I  T
GTCGACCAAGGAAAACGTTATCGTTTCCGTCTCGTCTCTATTTCATGCGACCCGAACTTCGTCTTCTCCATTGACAACCATTCCATGACT              240
 V  D  Q  G  K  R  Y  R  F  R  L  V  S  I  S  C  D  P  N  F  V  F  S  I  D  N  H  S  M  T
GTCATTGAAGTCGATGCTGTCAACAGCCAGCCTCTCGTCGTCGACTCTATTCAAATCTTCGCGGCACAGCGATACTCTTTCATTTTGAAT              270
 V  I  E  V  D  A  V  N  S  Q  P  L  V  V  D  S  I  Q  I  F  A  A  Q  R  Y  S  F  I  L  N
GCCAACCAAAGTGTCGGAAACTACTGGATCCGTGCCAACCCCAACTTGGGCAACACTGGTTTTACGAATGGCATTAACTCGGCCATTCTT              300
 A  N  Q  S  V  G  N  Y  W  I  R  A  N  P  N  L  G  N  T  G  F  T  N  G  I  N  S  A  I  L
CGGTACAATGGTGCTCCTGTTGCTGAGCCAACACCACCCAAACTGCTAGCACCAACCCCTTGAACGAGGTTAACCTTCACCCTCTAGTT              330
 R  Y  N  G  A  P  V  A  E  P  N  T  T  Q  T  A  S  T  N  P  L  N  E  V  N  L  H  P  L  V
CCCACGCCCGTCCCTGGTACTCCTCAGCCTGGCGGTGTTGATGTGTCCAGAACCTTGTCCTCGGTTTCAGCGGCGGCAAGTTCACTATC              360
 P  T  P  V  P  G  T  P  Q  P  G  G  V  D  V  V  Q  N  L  V  L  G  F  S  G  G  K  F  T  I
AACGGTGTTGCCTTTTCTCCCCCGACGGTCCCAGTTCTCCTTCAAATCCTTAGCGGTACTACTACTGCCCAAGATCTTCTTCCCACTGGA              390
 N  G  V  A  F  S  P  P  T  V  P  V  L  L  Q  I  L  S  G  T  T  T  A  Q  D  L  L  P  T  G Cu²⁺ binding site-III
TCCATTATCGAGCTTCCCCTCGGAAAGACTGTTGAACTTACCCTGGCAGCGGGCGTTCTCGGTGGTCCCCACCCCTTCCACTTGCACGGT              420
 S  I  I  E  L  P  L  G  K  T  V  E  L  T  L  A  A  G  V  L  G  G  P  H  P  F  H  L  H  G
CACACTTTCCACGTTGTTCGCAGCGCTGGTCAGACTACTCCTAACTACGTCGATCCTATTCTTCGTGACACTGTCAACACCGGTGCTGCT              450
 H  T  F  H  V  V  R  S  A  G  Q  T  T  P  N  Y  V  D  P  I  L  R  D  T  V  N  T  G  A  A GGCGACAATGTTACTATCCGTTTCACCACTGACAACCCTGGACCCTGGTTCCTCCACTGCCACATTGATTGGCACTTGGAAGCCGGTTTC              480
 G  D  N  V  T  I  R  F  T  T  D  N  P  G  P  W  F  L  H  C  H  I  D  W  H  L  E  A  G  F
GCTGTTGTCTTCGCTGAAGGTCTTAACCAGACCAATGCTGCTAACCCCACTCCTGATGCTTGGAACAACTTTTGCGACCTCTACAATGCC              510
 A  V  V  F  A  E  G  L  N  Q  T  N  A  A  N  P  T  P  D  A  W  N  N  L  C  D  L  Y  N  A
CTTCCTGCTGGTGACCAGTAG (SEQ ID NO: 21)                                                                    516
 L  P  A  G  D  Q  *  (SEQ ID NO: 9)
Lentinus sp. LccA (GenBank accession no. FJ693715)
```

```
                                                        -continued

ATGGCCAAGTTTCAGTCTTTGCTCTCCTACACCCTTCTCTCCCTCGTCGCCACTGTCTATGCAGGCATCGGCCCCATTGCTAGCCTCGTC
 M  A  K  F  Q  S  L  L  S  Y  T  L  L  S  L  V  A  T  V  Y  A  G  I  G  P  I  A  S  L  V     30

GTCACCGATGCCCAGATTAGCCCCGACGGCTACTTGCGCGATGCTATCGTGACCAATGGGGTCTTCCCAGCCCTCTGATCACTGGACGT
 V  T  D  A  Q  I  S  P  D  G  Y  L  R  D  A  I  V  T  N  G  V  F  P  A  P  L  I  T  G  R     60

Cu²⁺ binding site-I
AAGGGTGATCACTTCCAGCTGAATGTCGTGGATTCCATGACAAACCACACCATGCTGAAATCCACAAGTATCCACTGGCATGGCTTC       90
 K  G  D  H  F  Q  L  N  V  V  D  S  M  T  N  H  T  M  L  K  S  T  S  I  H  W  H  G  F  R CAGAAGGGCACAAACTGGGCTGATGGTCCTGCATTTGTGAACCAGTGCCCTATTTCCAGCGGCCACTCGTTCCTCTACGACTTCCACGTT   120
 Q  K  G  T  N  W  A  D  G  P  A  F  V  N  Q  C  P  I  S  S  G  H  S  F  L  Y  D  F  H  V Cu²⁺ binding site-II
CCGGACCAAGCAGGGACGTTCTGGTACCACAGTCACTTGTCCACTCAATACTGCGACGGTTTGAGGGGCCCGATGGTTGTGTACGATCCC   150
 P  D  Q  A  G  T  F  W  Y  H  S  H  L  S  T  Q  Y  C  D  G  L  R  G  P  M  V  V  Y  D  P AACGACCCTCATGCAAATCTCTACGACATCGATAACGACAGCACTGTGATAACTCTCGCCGATTGGTATCACGTCGCGGCCAAGCTCGGC   180
 N  D  P  H  A  N  L  Y  D  I  D  N  D  S  T  V  I  T  L  A  D  W  Y  H  V  A  A  K  L  G CCTCGCTTCCCACTTGGGGCTGATGCTACCCTTATCAACGGAAAGGGCAGAAGCCCTGCCACTCCCACAGCAGCACTGTCCGTCATCAAC   210
 P  R  F  P  L  G  A  D  A  T  L  I  N  G  K  G  R  S  P  A  T  P  T  A  A  L  S  V  I  N GTGGTCAAAGGCAAGCGGTATCGGTTCCGCTTGGTTTCAATCTCCTGCGACCCGAACTATGTGTTCAGCATCGACAACCATACGATGACG   240
 V  V  K  G  K  R  Y  R  F  R  L  V  S  I  S  C  D  P  N  Y  V  F  S  I  D  N  H  T  N  T GTCATCGAGGCCGATACCGTGAACACCCAGCCCCTCGCCGTCGACAGCATCCAGATCTTCGCGGCCCAGCGTTACTCATTCATTCTCAAC   270
 A  N  Q  P  V  D  N  Y  W  I  R  A  N  P  N  F  G  N  V  G  F  T  D  G  I  N  S  A  I  L GCCAACCAGCCCGTCGACAACTACTGGATTCGCGCCAACCCGAACTTCGGGAACGTCGGATTTACGGATGGCATCAACTCTGCTATCCTC   300
 A  N  Q  P  V  D  N  Y  W  I  R  A  N  P  N  F  G  N  V  G  F  T  D  G  I  N  S  A  I  L CGTTACACTGGGGCGGCACTGGTCGAACCGTCTGCGACCACCGCTCCGACACTGAGCAACCCTCTCGTCGAGACAAACCTGCATCCTCTT   330
 R  Y  T  G  A  A  L  V  E  P  S  A  T  T  A  P  T  L  S  N  P  L  V  E  T  N  L  H  P  L GCGCCCATGCCTGTGCCCGGACAACCCGTTTCCGGTGGTGTCGATAAGGCTATCAACTTCGCCTTCAACTTCGATGGCACGGACTTCTTC   360
 A  P  M  P  V  P  G  Q  P  V  S  G  G  V  D  K  A  I  N  F  A  F  N  F  D  G  T  D  F  F ATCAACGGCGCGAGCTTCGTCCCACCTACGGTTCCGGTCCTTCTCCAAATCATGAGCGGCGCCAGCACGGCCGAGGACCTCCTTCCTTCC   390
 I  N  G  A  S  F  V  P  P  T  V  P  V  L  L  Q  I  M  S  G  A  S  T  A  Q  D  L  L  P  S Cu²⁺ binding
GGCAGCGTCTACCCGCTTCCATCAAACGCGACGATCGAGCTCTCCTTCCCGGCGACCGCCGCTGCGCCTGGCGCCCCCCACCCCTTCCAC   420
 G  S  V  Y  P  L  P  S  N  A  T  I  E  L  S  F  P  A  T  A  A  A  P  G  A  P  H  P  F  H site-III
TTGCACGGCCACGTCTTCGCCGTCGTCCGCAGCGCGGGAAGCACCACCTACAATTACAACAACCCCATCTGGCGCGATGTCGTCAGCACT   450
 L  H  G  H  V  F  A  V  V  R  S  A  G  S  T  T  Y  N  Y  N  N  P  I  W  R  D  V  V  S  T Cu²⁺ binding
GGCACCCCTGCAGCGGGCGACAACGTCACCATCCGTTTTTCGACGAACAACCCGGGTCCGTGGTTCCTCCACTGCCACATCGACTTCCAC   480
 G  T  P  A  A  G  D  N  V  T  I  R  F  S  T  N  N  P  G  P  W  F  L  H  C  H  I  D  F  H site-IV
CTCGAGGCGGGCTTCGCAGTAGTCATGGCCGAAGACGTCCCCGACATTCCGTCTGCGAACCCTGTGCCCCAGGCGTGGTCGAACCTTTGC   510
 L  E  A  G  F  A  V  V  M  A  E  D  V  P  D  I  P  S  A  N  P  V  P  Q  A  W  S  N  L  C CCAACTTACAACGCGCTCAGTTCTGATGATCAGTAA  (SEQ ID NO: 22)                                          521
 P  T  Y  N  A  L  S  S  D  D  Q  *    (SEQ ID NO: 10)

Lentinus sp. LccB (GenBank accession no. FJ693716)

ATGGCCAAGTTTCAGTCTTTGCTCTCCTACACCCTTCTCTCCCTCGTCGCCACTGTCTATGCAGGCATCGGCCCCATTGCTAGCCTCGTC     30
 M  A  K  F  Q  S  L  L  S  Y  T  L  L  S  L  V  A  T  V  Y  A  G  I  G  P  I  A  S  L  V

GTCACCGATGCCCAGATTAGCCCCGACGGCTACTTGCGCGATGCTATCGTGACCAATGGGGTCTTCCCAGCCCTCTGATCACTGGACGT     60
 V  T  D  A  Q  I  S  P  D  G  Y  L  R  D  A  I  V  T  N  G  V  F  P  A  P  L  I  T  G  R

Cu²⁺ binding site-I
AAGGGTGATCACTTCCAGCTGAATGTCGTGGATTCCATGACAAACCACACCATGCTGAAATCCACAAGTATCCACTGGCATGGCTTC       90
 K  G  D  H  F  Q  L  N  V  V  D  S  M  T  N  H  T  M  L  K  S  T  S  I  H  W  H  G  F  R CAGAAGGGCACAAACTGGGCTGATGGTCCTGCATTTGTGAACCAGTGCCCTATTTCCAGCGGCCACTCGTTCCTCTACGACTTCCACGTT   120
 Q  K  G  T  N  W  A  D  G  P  A  F  V  N  Q  C  P  I  S  S  G  H  S  F  L  Y  D  F  H  V Cu²⁺ binding site-II
CCGGACCAAGCAGGGACGTTCTGGTACCACAGTCACTTGTCCACTCAATACTGCGACGGTTTGAGGGGCCCGATGGTTGTGTACGATCCC   150
 P  D  Q  A  G  T  F  W  Y  H  S  H  L  S  T  Q  Y  C  D  G  L  R  G  P  M  V  V  Y  D  P AACGACCCTCATGCAAATCTCTACGACATCGATAACGACAGCACTGTGATAACTCTCGCCGATTGGTATCACGTCGCGGCCAAGCTCGGC   180
 N  D  P  H  A  N  L  Y  D  I  D  N  D  S  T  V  I  T  L  A  D  W  Y  H  V  A  A  K  L  G CCTCGCTTCCCACTTGGGGCTGATGCTACCCTTATCAACGGAAAGGGCAGAAGCCCTGCCACTCCCACAGCAGCACTGTCCGTCATCAAC   210
 P  R  F  P  L  G  A  D  A  T  L  I  N  G  K  G  R  S  P  A  T  P  T  A  A  L  S  V  I  N GTGGTCAAAGGCAAGCGGTATCGGTTCCGCTTGGTTTCAATCTCCTGCGACCCGAACTATGTGTTCAGCATCGACAACCATACGATGACG   240
 V  V  K  G  K  R  Y  R  F  R  L  V  S  I  S  C  D  P  N  Y  V  F  S  I  D  N  H  T  H  T GTCATCGAGGCCGATACCGTGAACACCCAGCCCCTCGCCGTCGACAGCATCCAGATCTTCGCGGCCCAGCGTTACTCATTCATTCTCAAC   270
 V  I  E  A  D  T  V  N  T  Q  P  L  A  V  D  S  I  Q  I  F  A  A  Q  R  Y  S  F  I  L  N GCCAACCAGCCCGTCGACAACTACTGGATTCGCGCCAACCCGAACTTCGGGAACGTCGGATTTACGGATGGCATCAACTCTGCTATCCTC   300
```

-continued

```
                             A  N  Q  P  V  D  N  Y  W  I  R  A  N  P  N  F  G  N  V  G  F  T  D  G  I  N  S  A  I  L
CGTTACACTGGGGCGGCACTGGTCGAACCGTCTGCGACCACCGCTCCGACACTGAGCAACCCTCTCGTCGAGACAAACCTGCATCCTCTT    330
 R  Y  T  G  A  A  L  V  E  P  S  A  T  T  A  P  T  L  S  N  P  L  V  E  T  N  L  H  P  L
GCGCCCATGCCTGTGCCCGGACAACCCGTTTCCGGTGGTGTCGATAAGGCTATCAACTTCGCCTTCAACTTCGATGGCACGGACTTCTTC    360
 A  P  M  P  V  P  G  Q  P  V  S  G  G  V  D  K  A  I  N  F  A  F  N  F  D  G  T  D  F  F
ATCAACGGCGCGAGCTTCGTCCCACCTACGGTTCCGGTCCTTCTCCAAATCATGAGCGGCGCCAGCACGGCGCAGGACCTCCTTCCTTCC    390
 I  N  G  A  S  F  V  P  P  T  V  P  V  L  L  Q  I  M  S  G  A  S  T  Q  D  L  L  P  S

Cu²⁺ binding
GGCAGCGTCTACCCGCTTCCATCAAACGCGACGATCGAGCTCTCCTTCCCGGCGACCGCCGCTGCGCCTGGCGCCCCCCACCCCTTCCAC    420
 G  S  V  Y  P  L  P  S  N  A  T  I  E  L  S  F  P  A  T  A  A  A  P  G  A  P  H  P  F  H site-III
TTGCACGGCCACGTCTTCGCCGTCGTCCGCAGCGCGGGAAGCACCACCTACAATTACAACAACCCCATCTGGCGCGATGTCGTCAGCACT    450
 L  H  G  H  V  F  A  V  V  R  S  A  G  S  T  T  Y  N  Y  N  N  P  I  W  R  D  V  V  S  T Cu²⁺ binding
GGCACCCCTGCAGCGGGCGACAACGTCACCATCCGTTTTTCGACGAACAACCCGGGTCCGTGGTTCCTCCACTGCCACATCGACTTCCAC    480
 G  T  P  A  A  G  D  N  V  T  I  R  F  S  T  N  N  P  G  P  W  F  L  H  C  H  I  D  F  H CTCGAGGCGGGCTTCGCAGTAGTCTAG (SEQ ID NO: 23)                                                  488
 L  E  A  G  F  A  V  V  *  (SEQ ID NO: 11)
Lentinus sp. LccC (GenBank accession no. GQ220322)

ATGGCCAAGTTCCAGTCGTTGCTTTCTTACACTGTCCTCTCCTTCGTCGCGGCTGCCTATGCTGCCATCGGCCCAGTCGCTGACCTTACC    30
 M  A  K  F  Q  S  L  L  S  Y  T  V  L  S  F  V  A  A  A  Y  A  A  I  G  P  V  A  D  L  T

ATCAGCAATGCCCAAGTCAGCCCCGACGGCTTCCTCCGCGATGCCGTCGTGACCAACGGCCTGGTCCCTGGGCCCCTCATCACGGGCAAC    60
 I  S  N  A  Q  V  S  P  D  G  F  L  R  D  A  V  V  T  N  G  L  V  P  G  P  L  I  T  G  N

Cu²⁺ binding site-I
AAGGGCGATCGCTTCCAGTTGAATGTCATTGATCAAATGACCAACCACACGATGTTGAAGACTACGAGCATTCACTGGCACGGCTTCTTC    90
 K  G  D  R  F  Q  L  N  V  I  D  Q  M  T  N  H  T  M  L  K  T  T  S  I  H  W  H  G  F  F CAGAAGGGCACCAACTGGGCTGATGGACCTGCGTTTGTGAACCAGTGCCCCATTGCCAGCGGCAACTCCTTCCTCTACGACTTCCAGGTC    120
 Q  K  G  T  N  W  A  D  G  P  A  F  V  N  Q  C  P  I  A  S  G  N  S  F  L  Y  D  F  Q  V Cu²⁺ binding site-II
CCTGACCAGGCTGGCACCTTCTGGTATCACAGCCACCTTTCGACCCAGTACTGCGACGGTCTCCGGGGGCCTCTCGTTGTGTACGACCCC    150
 P  D  Q  A  G  T  F  W  Y  H  S  H  L  S  T  Q  Y  C  D  G  L  R  G  P  L  V  V  Y  D  P AATGACCCACACGCTGCCCTCTATGATATCGACGATGATAACACCGTTATTACTTTGACTGACTGGTACCATACTGCGGCCAGGCTCGGA    180
 N  D  P  N  A  A  L  Y  D  I  D  D  D  N  T  V  I  T  L  T  D  W  Y  N  T  A  A  R  L  G CCTCGTTTCCCGCTGGGAGCAGATGCCACTCTCATCAACGGCCTGGGCCGCAGCCAGCCACCGCCGACCGCCAACCTAACTGTCATCAAC    210
 P  R  F  P  L  G  A  D  A  T  L  I  N  G  L  G  R  S  P  A  T  P  T  A  N  L  T  V  I  N GTTACTCAGGGCAAGCGCTACCGCTTCCGCCTCGTGTCGATCTCTTGCGACCCGAACTATGTGTTCAGCATCGACAACCACACGATGAGC    240
 V  T  Q  G  K  R  Y  R  F  R  L  V  S  I  S  C  D  P  N  Y  V  F  S  I  D  N  H  T  M  S GTCATTGAGACGGACACTGTCAACACTCAACCGCTCACGGTCGATAGCATTCAGATCTACGCCGCCCAGCGCTACTCCTTTGTGCTCACC    270
 V  I  E  T  D  T  V  N  T  Q  P  L  T  V  D  S  I  Q  I  Y  A  A  Q  R  Y  S  F  V  L  T GCCAACCAGTCCGTGGATAACTACTGGATCCGGGCAAACCCCAACTTCGGTAACGTCGGCTTCACGGATGCTATCAACTCGGCCATCCTC    300
 A  N  Q  S  V  D  N  Y  W  I  R  A  N  P  N  F  G  N  V  G  F  T  D  A  I  N  S  A  I  L CGCTATGACGGTGCTCCCGACGCTGAGCCCTCCGCTACCACTGCACCGACGTTGACCAACGCTGGTTGAGGCGAACCTTTCACCCGCTT    330
 R  Y  D  G  A  P  D  A  E  P  S  A  T  T  A  P  T  L  T  N  P  L  V  E  A  N  L  N  P  L GCTTCGATGCCCGTGCCCGGATCCCTGTGTCTGGCGGTGTGGACAAGGCCATTAACTTCGTCTTCAACTTCAACGGCACGAACTTCTCC    360
 A  S  M  P  V  P  G  S  V  S  G  G  V  D  K  A  I  N  F  V  F  N  F  N  G  T  N  F  S ATCAACAACGCGACTTTCGTTCCGCCCACCGTTCCGGTGCTGCTCCAGATCATGAGCGGCGCCAACACCGCCCAAGACCTCCTGCCCTCT    390
 I  N  N  A  T  F  V  P  P  T  V  P  V  L  L  Q  I  M  S  G  A  N  T  A  Q  D  L  L  P  S Cu²⁺ binding
GGCAGCGTGTACACACTCCCGTCCAACGCTACCATTGAGCTGTCCTTCCCTGCGACGAGCAACGCCCCCGGCGCTCCTCACCCCTTCCAC    420
 G  S  V  Y  T  L  P  S  N  A  T  I  E  L  S  F  P  A  T  S  N  A  P  G  A  P  H  P  F  H TTGCACGGTCACGTCTTCGCCGTTGTCCGCAGCGCTGGCAGCACCGTCTACAACTACGACAACCCCATCTGGCGCGACGTCGTCAGCACC    450
 L  H  G  H  V  F  A  V  V  R  S  A  G  S  T  V  Y  N  Y  D  N  P  I  W  R  D  V  V  S  T Cu²⁺ binding
GGCACCCCTGCAGCGGGCGACAACGTCACCATCCGCTTCCAGACAACAACCCTGGTCCCTGGTTCCTCCACTGTCACATCGACTTCCAC    480
 G  T  P  A  A  G  D  N  V  T  I  R  F  Q  T  N  N  P  G  P  W  F  L  H  C  H  I  D  F  H site-IV
CTCGACGCCGGCTTTGCCGTGGTCATGGCTGAGGACCCTGTTGACACTCCGACGGCGGATCCCGTTCCCAGGCGTGGTCCGATCTCTGC    510
 L  D  A  G  F  A  V  V  M  A  E  D  P  V  D  T  P  T  A  D  P  V  P  Q  A  W  S  D  L  C CCGACATACGACGCGCTTTCCGTCGACGACCAGTGA (SEQ ID NO: 24)                                         521
 P  T  Y  D  A  L  S  V  D  D  Q  *  (SEQ ID NO: 12)
```

In the above listed sequences, the underlined and italic regions refer to signal peptides, the bold-faced residues refer to glycosylation sites (either predicted by computational methods or determined by mass spectrometry or mutagenesis), and the highlighted regions refer to copper-binding sites. It is known that copper-binding sites are essential to the enzymatic activity of a laccase. Further, in each of the *Lentinus* sp. laccases, an N-terminal domain (i.e., residues 40-265 in precursor LccB and the corresponding regions in LccA and LccC) and a C-terminal domain (i.e., residues 360-488 in precursor LccB and the corresponding domains in LccA and LccC) are functionally important. The glycosylation sites in each of the *Lentinus* sp. laccases have also found to be functionally important.

Also described herein are functional variants of Lcc1, Lcc2, Lcc3, LccA, LccB, and LccC that share at least 85% (e.g., 90%, 95%, or 98%) sequence identity to SEQ ID NO:1, 2, 3, 4, 5, or 6. The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Relative to their wild-type counterparts, the functional variants of Lcc1, Lcc2, Lcc3, LccA, LccB, and LccC can contain conservative mutations inside the functional domains or at the essential residue positions as described above. A mutation is conservative when the amino acids used for the substitutions have structural or chemical characteristics similar to those of the corresponding replaced amino acids. Examples of conservative substitutions can include: substitution of Ala with Gly or Val, substitution of Arg with His or Lys, substitution of Asn with Glu, Gln, or Asp, substitution of Asp with Asn, Glu, or Gln, substitution of Cys with Ser or Ala, substitution of Gln with Asn, Glu, or Asp, substitution of Glu with Gly, Asn, Gln, or Asp, substitution of Gly with Val or Ala, substitution of Ile with Leu, Met, Val, or Phe, substitution of Leu with Ile, Met, Val, or Phe, substitution of Lys with His or Arg, substitution of Met with Ile, Leu, Val, or Phe, substitution of Phe with Trp, Tyr, Met, Ile, or Leu, substitution of Ser with Thr or Ala, substitution of Thr with Ser or Ala, substitution of Trp with Phe or Tyr, substitution of Tyr with His, Phe, or Trp, and substitution of Val with Met, Ile, Leu, or Gly.

Conservative mutations in the functional domains would not abolish the enzymatic activity of the resultant laccase variants. On the other hand, domains not essential to the laccase activity are tolerable to mutations as amino acid substitutions within these domains are unlikely to greatly affect enzyme activity.

Lcc1, Lcc2, Lcc3, LccA, LccB, LccC, and any of its functional variants can be prepared by conventional recombinant technology. Generally, a coding sequence for one of the laccases can be isolated from *Cerrena* sp. WR1 or *Lentinus* sp. via routine molecular cloning technology. Nucleotide sequences coding for one of the variants can be prepared by modifying a wild-type laccase coding sequence. Any of the coding sequences can then be inserted into an expression vector, which contains a suitable promoter in operative linkage with the coding sequence. If necessary, the coding sequence can be subjected to codon optimization based on the type of the host cell to be used for expressing the laccase.

As used herein, a "vector" refers to a nucleic acid molecule capable of transporting another nucleic acid to which it has been linked. The vector can be capable of autonomous replication or integrate into a host DNA. Examples of the vector include a plasmid, cosmid, or viral vector. An expression is a vector in a form suitable for expression of a target nucleic acid in a host cell. Preferably, an expression vector includes one or more regulatory sequences operatively linked to a target nucleic acid sequence to be expressed. The term "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of transcription of RNA desired, and the like.

The term "promoter" refers to a nucleotide sequence containing elements that initiate the transcription of an operably linked nucleic acid sequence in a desired host cell. At a minimum, a promoter contains an RNA polymerase binding site. It can further contain one or more enhancer elements which, by definition, enhance transcription, or one or more regulatory elements that control the on/off status of the promoter. When *E. coli* is used as the host, representative *E. coli* promoters include, but are not limited to, the β-lactamase and lactose promoter systems (see Chang et al., *Nature* 275:615-624, 1978), the SP6, T3, T5, and T7 RNA polymerase promoters (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155-164, 1983), and the Tac and Trc promoters (Russell et al., *Gene* 20:231-243, 1982). When yeast is used as the host, exemplary yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Promoters suitable for driving gene expression in other types of microorganisms are also well known in the art. Examples of mammalian cell promoters include, but are not limited to, CMV promoter, SV40 promoter, and actin promoter.

The expression vector described above is then introduced into a suitable host (e.g., *E. coli*, yeast, an insect cell, and a mammalian cell) for expressing of one of the laccases described herein. Positive transformants/transfectants are selected and over-expression of the enzyme can be confirmed by methods known in the art, e.g., immune-blotting or enzymatic activity analysis. A host cell carrying the expression vector is then cultured in a suitable medium under suitable conditions for laccase production. The culture medium or the cells are harvested for isolation of the enzyme. When the enzyme is expressed in precursor form, i.e., containing an N-terminal signal peptide, it is preferred that the culture medium be collected for enzyme isolation. The activity of the isolated enzyme can then be confirmed by a conventional assay, e.g., those described in Example 1 below.

Alternatively, a wild-type laccase or a variant thereof can be prepared by culturing a suitable *Cerrena* sp. or *Lentinus* sp. strain via a traditional method. See, e.g., Examples 1 and 2 below. The enzyme can be purified from the culture medium.

The laccases described herein can oxidize various aromatic, particularly phenolic substrates (e.g. hydroquinone, guaiacol, 2,6-dimethoxyphenol or phenylene diamine), coupled to the reduction of molecular oxygen to water. As such, they have broad biotechnological and industrial applications. For example, they can be used to detoxify industrial effluents, particularly those from the paper and pulp, textile and petrochemical industries. In addition, the laccases described herein can be used to detect and clean up herbicides, pesticides, and certain explosives in environmental water or soil. They also can be used in treating industrial wastewater. Further, given their capacity of removing xenobiotic substances and producing polymeric products, they can serve as bioremediation agents to reduce environmental contamination, decoloration of phenolic dyes, or detoxification of toxic compounds produced, e.g., in bioethanol fermentation. The laccases can also be used in food industry to remove phenolic compounds in food products, thereby enhancing food quality or to catalyze chemical synthesis.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Isolation and Characterization of Three Novel Laccases from *Cerrena* sp. WR1

(i) *Cerrena* sp. WR1 Cultivation and Laccase Production

Fungus strain *Cerrena* sp. WR1 was maintained on a 3.9% potato dextrose agar (PDA, Difico™, BD) plate. Mycelial plugs from the leading edges of a colony were shattered completely with glass beads in dH$_2$O and inoculated into a 5 L fermenter (Biostat® B, B. Braun Biotech) containing 4 L cultivation broth, 2.4% potato dextrose broth (PDB) (Difico™, BD), 5% soytone, and 0.4 mM CuSO$_4$ at 25° C. at a stirring speed of 200 rpm with an air flow rate of 1 vvm. Three days later, 2,5-xylidine was added to the culture (final concentration 2 mM) to induce laccase production. The fungal culture was cultivated for additional ten days and the supernatant was collected. Its protein concentration was analyzed by the standard Bradford method (Bio-Rad). The laccase activity in the supernatant was also determined via routine technology.

Genomic DNAs were isolated from *Cerrena* sp. WR1, using the Genomic DNA Purification Kit provided by Easy-Pure, Bioman Scientific Co., LTD, Taiwan, following the manufacturer's protocol. Universal primers NS1 (5'-GTAGT-CATATGCTTGTCTC-3'; SEQ ID NO:25) and NS8 (5'-CCGCAGCTTCACCTACGGA-3'; SEQ ID NO:26) were used to amplify a ~1760 bp-long fragment of 18S rDNA via PCR reactions. See Cheng et al., J. Basic Microbiol. 44 (5): 339-350, 2004. PCR analysis was performed, using a Biometra TGradient Thermocycler (Biometra, Goettingen, Germany), to amplify cDNA fragments encoding 18S rRNA. The PCR conditions are: 30 cycles of 94° C. for 1 min, 56° C. for 45 sec, 72° C. for 2 min, and 72° C. for 5 min. 18S rDNAs of other fungal species were obtained from GenBank and phylogenetic analysis was performed using the computational tool provided by the Biology Workbench website (workbench.sdsc.edu/), following the method described in Lai et al., Int. J. Syst. Enol. Microbiol. 51:1873-1880, 2001.

The 18S rDNA sequence of *Cerrena* sp. WR1 was compared with the 18S rDNA sequences from other fungal species retrieved from the GenBank database. A phylogenetic tree was generated based on the results. See FIG. 1. *Cerrena* sp. WR118S rDNA shares 99.15% identity to that from 18S rDNA *C. unicolor*, indicating that these two *Cerrena* strains are very close.

(ii) Protein Purification and Characterization

Mycelia of *Cerrena* sp. WR1 were grown in a culture medium containing 2.4% potato dextrose broth, 5% soytone, and 0.4 mM CuSO$_4$ for 13 days. Fungal cells were removed from the culture medium by filtration using a filter paper (5C, Advantec, Toyo Roshi Kaisha, Ltd.) and then a 0.45 µM membrane (Millipore).

Laccase activity in the medium thus collected was determined by the standard 2,2'-azino-bis-(3-ethylbenzthiazoline-6-sulfonic acid (ABTS) oxidation assay as described in Murugesan et al., Appl. Microbiol. Biotechnol. 72 (5):939-946, 2006. More specifically, 0.5 ml test sample was incubated with 0.5 ml citric acid buffer (100 mM, pH 3.0) containing ABTS (4 mM) and the optical density at 420 nm ($\epsilon_{420}$=36,000 M$^{-1}$ cm$^{-1}$) of the mixture was measured at various time points. One unit of the enzyme activity was defined as the amount of enzyme needed to oxidize 1 µmol of ABTS per min. Kinetic studies were performed independently for at least three times at different substrate concentrations, pH conditions, and temperatures. All chemicals used in this study were obtained from Merck (Darmstadt, Germany) or Sigma-Aldrich (St. Louis, Mo. USA). All spectrophotometric measurements were performed using the Beckman DU 640 spectrophotometer (Beckman Coulter, USA).

Figure 2:
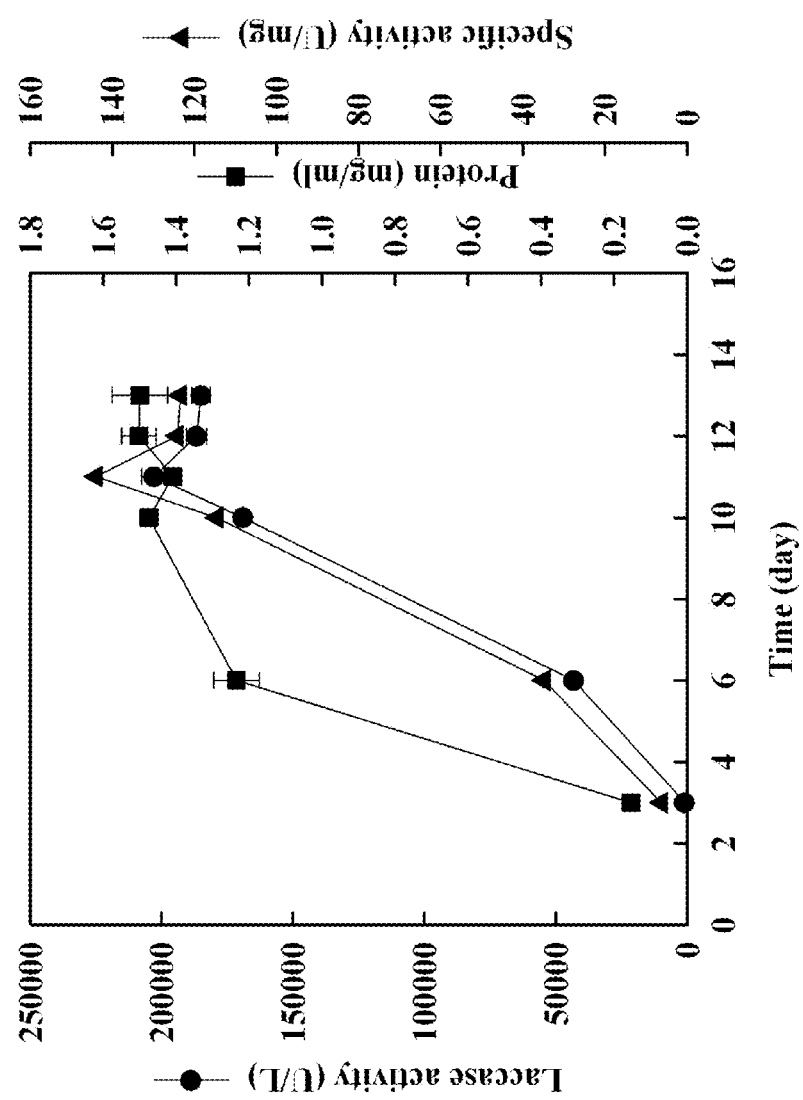
FIG. 2 is a chart showing a time course of laccase activities, protein levels, and specific activities during a 13-day fermentation period of *Cerrena* sp. WR1.

As shown in FIG. 2, the laccase activity in the culture medium increased in the 13-day fermentation period in a time dependent manner. The highest laccase activity reaches approximately 202,000 U/L, and the specific activity of the crude laccases was 144.3 U/mg.

Laccases were isolated from the medium thus collected follow the procedure described below, which was performed at 4° C. The medium was first concentrated using the Labscale™ TFF System (Millipore) with a 10K Pellicon®-XL filter. The concentrated medium was then subjected to ammonium sulfate precipitation. Proteins precipitated with 40-60% ammonium sulfate were collected by centrifugation at 6,000×g for 35 min and resuspended in 50 mM sodium phosphate buffer, pH 6.0 ("buffer A"). The resulting protein solution was loaded onto a Q Sepharose Fast Flow column (2.6× 40 cm, GE Healthcare, Uppsala, Sweden) equilibrated with buffer A. The column was washed with the same buffer and the proteins bound to it were eluted with a linear gradient of NaCl (0 to 1 M) in buffer A at a flow rate of 1 mL/min. Each fraction was examined to determine its laccase activity and those exhibiting laccase activity were pooled, concentrated, and dialyzed against buffer A. Homogeneity of the enzyme was confirmed the conventional SDS-PAGE analysis, as well as by zymography analysis and mass spectrometry described below.

Zymography analysis was performed to determine the enzymatic activity as follows. The proteins, suspended in a lysis buffer, were separated on a 10% SDS polyacrylamide gel. After electrophoresis, the gel was rinsed twice with 50 mM citric acid buffer (pH 3.0) for 5 min each time to remove SDS, then immersed in the same buffer containing 1 mM 2,2'-azino-bis-(3-ethylbenzthiazoline-6-sulfonic acid) (ABTS) (Sigma), which is a laccase substrate. The protein bands exhibiting laccase activity can then be visualized. The exact mass of the purified laccase was determined by use of Thermo Finnegan ProteomeX LTQ (LC-ESI-MS/MS) (Thermo, Mass.) at the Proteomics Core Laboratory, Institute of Plant and Microbial Biology, Academia Sinica, Taiwan.

After the second Q Sepharose Fast Flow column purification, the enzyme was purified about 24.9-fold with a yield of 6.5%, and specific activity of the purified laccase with >95% homogeneity was determined as 2,159.6 U/mg at 30° C. and pH 3.0. The purified laccase, designated as *Cerrena* sp. WR1 Lcc3, was subjected to N-terminal sequencing using a Procise® LC Protein Sequencing System, Model 492 (Applied Biosystems) and LC/MS-MS analysis.

A purified *Cerrena* sp. WR1, designated Lcc3, was also subjected to deglycosylation analysis using the Enzyme Protein Deglycosylation Kit (Sigma-Adlrich), following the manufacturer's protocol. PNGase F, O-glycosidase, α-2(3,6, 8,9) neuraminidase, β-1,4-galactosidase, and β-N-acetylglucosaminidase were used for deglycosylation. The treated laccase, together with an untreated laccase (as a control), was subjected to transblotting onto a polyvinylidene fluoride (PVDF) membrane (Millipore) and periodic acid Schiff staining was then performed as described in Cagatay et al., Veterinary Microbiology 126(1-3): 160-167, 2008 and Gradilone et al., Analytical Biochemistry 261(2):224-227, 1998. The molecular weight of Lcc3, before and after deglycosylation analysis, was determined to be 64.1 and 57.5 kDa, respectively, via SDS-PAGE (10% gel). The glycosylation level in this laccase was calculated to be 11.5%.

UV-Vis absorption spectra analysis showed that Lcc3 exhibited a broad absorption peak at 600 nm and a shoulder absorption at 330 nm. This indicates that Lcc3 contains both type I and type III copper ions.

Thermal denaturation of laccase was determined by differential scanning calorimetry (DSC) using a Nano Differential Scanning calorimeter (N-DSC III) (TA Instruments, New Castle, Del.) at a heating rate of 1° C./min under a temperature from 30 to 95° C. and excess pressure of 3.0 atm. The protein concentration was 0.55 mg/ml in 10 mM sodium phosphate buffer (pH 6.0). Baseline corrections were performed and smoothed by subtracting a buffer thermogram. The data were then analyzed using the Launch NanoAnalyze Software (TA Instruments, New Castle, Del.), assuming a two-state unfolding model. See Pace et al., The Protein Structure: A Practical Approach; Creighton T. E., Ed.: IRL Press; Oxford U.K., pp. 311-330; 1989. Results from this DSC analysis demonstrated that Lcc3 was denatured at a high temperature, with a midpoint temperature ($T_m$) of 73.95° C., in 10 mM sodium phosphate buffer (pH 6.0).

(iii) Effect of Temperature, pH, and Solvent on Laccase Activity and Stability

The effect of temperature on laccase activity was studied using the standard enzymatic activity assay described above under various reaction temperatures (i.e., 20-80° C.). For thermal stability study, the enzyme was pre-incubated in a 50 mM citric acid buffer (pH 3.0) at 50-80° C. for 0-180 min and the residual enzymatic activity was then determined.

Figure 3:
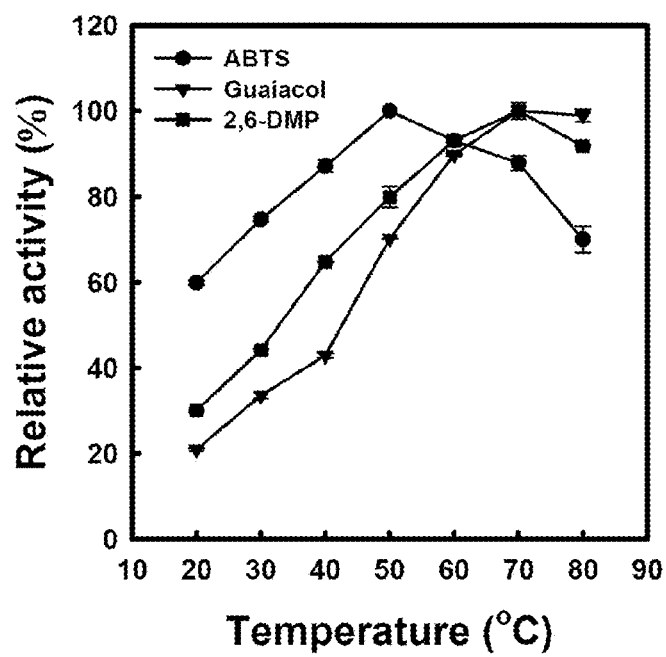
FIG. 3 is a diagram showing the effects of temperature and pH on activity and stability of *Cerrena* sp. WR1 Lcc3. Panel A: effect of temperature on laccase activity; Panel B: effect of temperature on laccase stability; Panel C: effect of pH on laccase activity; Panel D: effect of pH on laccase stability.
Figure 3:
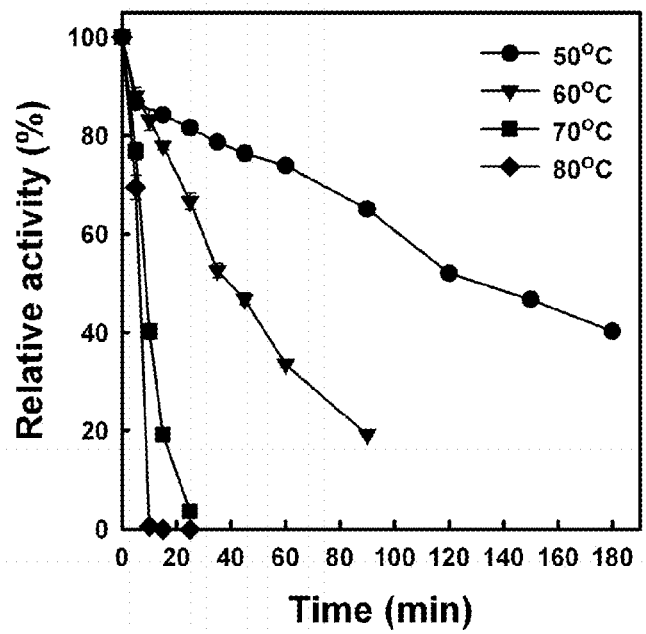
Figure 3:
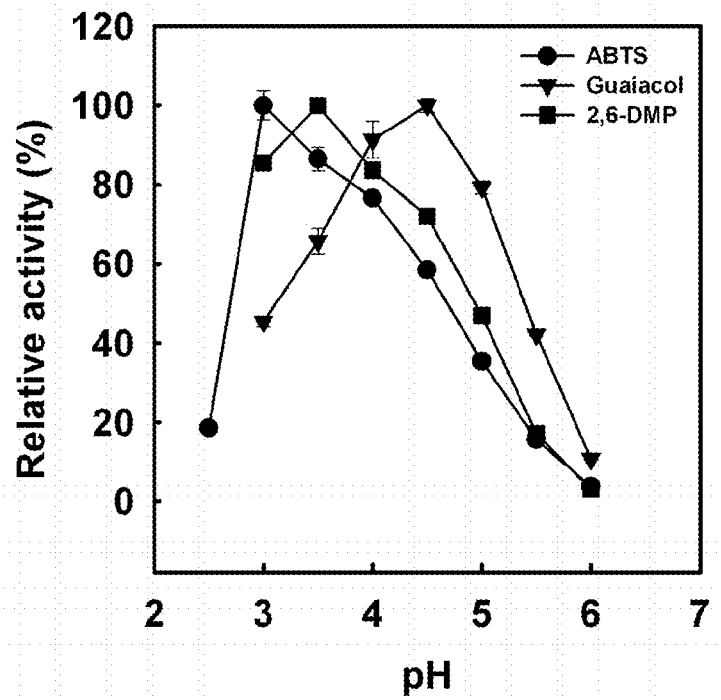
Figure 3:
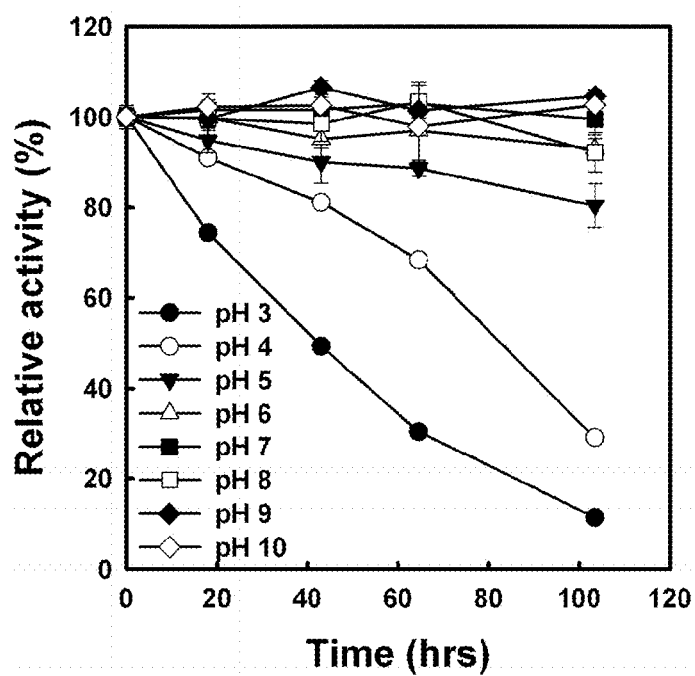

As shown in FIG. 3, panel A, the optimal temperature for *Cerrena* sp. WR1 Lcc3 was 50° C. when ABTS was used as the substrate and 70° C. when guaiacol or 2,6-DMP was used as the substrate. To test thermal stability, the enzyme was kept at various temperatures (50-80° C.) for 10-40 min and the remaining enzymatic activity was determined using the standard activity assay. Thermal stability at a particular temperature is represented by a $t_{1/2}$ value at that temperature, which represents the longest incubation period during which at least 50% of the enzymatic activity remains. The values of $t_{1/2}$ at 50° C., 60° C., and 70° C. were 120 min, 40 min, and 7.5 min, respectively. See FIG. 3, panel B. Surprisingly, the $t_{1/2}$ of the enzyme incubated at room temperature (25° C.) in a 50 mM sodium phosphate buffer (pH 6.0) was determined to be 40 days, indicating that this laccase is very stable at room temperature.

The effect of pH on the laccase activity was investigated at a pH range of 2.5-6.0. Four buffer systems were used in this study: 50 mM glycine-HCl buffer (pH 2.5), 50 mM citric acid buffer (pH 3.0-5.5), 50 mM sodium phosphate buffer (pH 6.0-8.0), and 50 mM glycine-NaOH buffer (pH 9.0-10). To determine the protein stability of laccase at a wide range of pH conditions, the enzyme (0.1 mg/mL in each reaction) was pre-incubated at pH 3.0-10 at 25° C. for 0-5 days and then the residual enzyme activity was determined.

Lcc3 showed a maximal activity at pH 3.0, 3.5, and 4.5, using ABTS, 2,6-DMP, and guaiacol as the substrates, respectively. See FIG. 3, panel C. This laccase was found to be stable under a neutral or basic environment (pH 6-10). It maintained about 100% activity at pH 6-10 after 63 hr incubation. See FIG. 3, panel D. On the other hand, Lcc3 was found to be less stable at an acidic environment (pH 3.0-5.0).

To test the effects of various organic solvents on laccase activity, the enzymatic assay described above was carried out in the presence of one of the organic solvents shown in Table 1 below at various concentrations (1%, 10% and 25%). A *T. versicolor* (Fluka) laccase was used as a reference enzyme in this study. The enzyme concentration used in this study was 0.2 mg/ml. As shown in Table 1, Lcc3 retained at least 81% activity in the presence of 25% methanol and N,N-dimethyl formamide. Further, more than 80% laccase activity remained in the presence of 10% acetonitrile or dimethyl sulfoxide.

TABLE 1

Effect of Various Organic Solvent on *Cerrena* sp. WR1. Lcc3

| Organic solvents | Relative activity (%)* | | |
|---|---|---|---|
| | 1% | 10% | 25% |
| Methanol | 93.0 ± 1.5 | 85.5 ± 0.9 | 74.6 ± 1.4 |
| Ethanol | 94.5 ± 1.8 | 93.9 ± 4.0 | 84.8 ± 3.3 |
| Acetonitrile | 92.7 ± 2.5 | 86.7 ± 0.8 | 77.5 ± 3.2 |
| N,N-dimethylformamide | 100 ± 0.9 | 98.4 ± 0.5 | 81.2 ± 0.5 |
| Dimethyl sulfoxide | 93.5 ± 1.4 | 81.1 ± 2.2 | 55.8 ± 1.7 |

*Assay reactions were performed in 50 mM citric acid buffer (pH 3.0) at 30° C., with ABTS used as the substrate.

To examine the effect of ethanol on *Cerrena* sp. WR1 laccase stability, the enzyme was incubated in a 50 mM sodium phosphate buffer (pH 6.0) containing 1%, 10%, or 25% ethanol at room temperature for up to 52 days and the residual enzyme activity was measured at different time points during incubation. A *T. versicolor* laccase (LccTv) was used as a reference enzyme. The results indicate that LccTv lost approximately 50% activity after being incubated with 25% ethanol for 8 days, while it maintained about 50% activity after a 21-day incubation in the absence of ethanol. Differently, Lcc3 retained around 90% activity after being incubated with 25% ethanol for 10 days and retained approximately 50% enzymatic activity after a 40-day incubation period. This enzyme also retained about 50% enzymatic activity after a 45-day incubation period with 10% ethanol and a 40-day incubation without ethanol. After a 52-day incubation period with 1% ethanol, Lcc3 still exhibited about 61% activity. These results demonstrate that Lcc3 is stable when exposed to ethanol, indicating that this enzyme has a great potential in biofuel industry.

(iv) Laccase Kinetics

Kinetic parameters $K_m$ and $V_{max}$ were determined as follows. Enzymatic activity using various substrates at various concentrations (i.e., ABTS: 1-1000 µM; guaiacol: 1-3000 µM; and 2,6-DMP: 1-2000 µM) was determined in a citrate buffer (50 mM) at the optimum temperature and pH conditions mentioned above. The oxidation reactions of guaiacol and 2,6-DMP were monitored by determining $OD_{436}$ values ($\epsilon$=6,400 $M^{-1}$ $cm^{-1}$) and $OD_{468}$ values ($\epsilon$=49,600 $M^{-1}cm^{-1}$), respectively. The kinetic parameters were determined by nonlinear regression analysis (ENZFITTER software program, Elsevier-Biosoft, Cambridge, UK) using the Michaelis-Menten model.

The affinities ($K_m$), turnover rate ($k_{cat}$), and catalytic efficiency ($k_{cat}/K_m$) of Lcc3 were determined to be 3.27 μM, 934.6 $s^{-1}$, and 285.8 $s^{-1}$ $μM^{-1}$ for ABTS, 849.1 μM, 147.9 $s^{-1}$, and 0.21 $s^{-1}$ $μM^{-1}$ for guaiacol, and 392.7 μM, 109.2 $s^{-1}$, and 0.28 $s^{-1}$ $μM^{-1}$ for 2,6-DMP, respectively. The kinetics of the Cerrena sp. WR1 laccases were compared with laccases from other fungal species and the results are shown in Table 2 below:

TABLE 2

Kinetic properties of laccases from various microorganisms

| Fungal Species | Specific activity (U/mg) | $k_{cat}$ ($s^{-1}$) | $K_m$ (μM) | $k_{cat}/K_m$ ($s^{-1}$ $μM^{-1}$) | Optimum temperature (° C.) | $t_{1/2}$ (min) | |
|---|---|---|---|---|---|---|---|
| Cerrena sp. WR1[a] | 1013.5 | 934.6 | 3.27 | 285.8 | 50 (at pH 3.0) | 120 | (at 50° C.) |
| | | | | | | 40 | (at 60° C.) |
| | | | | | | 8 | (at 70° C.) |
| Cerrena sp. WR1[b] | 189.7 | 147.9 | 849.1 | 0.21 | 70 (at pH 4.5) | — | |
| Cerrena sp. WR1[c] | 118.3 | 109.2 | 392.7 | 0.28 | 70 (at pH 3.5) | — | |
| Trametes versicolor[a] | 750 | — | — | — | 50 (at pH 3.0) | 15 | (at 50° C.) |
| | | | | | | 5 | (at 70° C.) |
| Melanocarpus sp.[a] | 42.45 | — | — | — | 70 (at pH 6.0) | >360 | (at 50° C.) |
| | | | | | | <15 | (at 70° C.) |
| Coriolus versicolor[a] | 0.3 | — | — | — | 25 (at pH 4.5) | — | |
| Trametes versicolor[a] | 310 | 351.3 | 37.3 | 9.4 | 55 (at pH 4.0) | — | |
| Trametes C30 LAC2[a] | 934 | 683.33 | 536 | 1.27 | 55 (at pH 5.7) | — | |
| Trametes pubescens LAP2[a] | 1100 | 350 | 43 | 8.14 | 25 (at pH 4.0) | — | |
| Cerrena unicolor[a] | | | 800 | | 70 (at pH 3.5) | <25 | (at 50° C.) |
| Panus(Lentinus)tigrinus 8/18[a] | | | 33.4 | | | | |
| Agaricus blazei[a] | 174.6 | 21 | 63 | 0.33 | 25 (at pH 2.3) | >250 | (at 25° C.) |
| Panus tigrinu[a] | — | 185.69 | 31 | 5.99 | 30 (at pH 3.5) | 150 | (at 25° C.) |
| Pleurofus sajor-caju[a] | 1244.4 | 520.24 | 56 | 9.29 | 40 (at pH 5.0) | — | |
| Pycnoporus sanguineus[a] | 340.76 | 1.155 | 77 | 0.015 | 25 (at pH 3.0) | — | |

[a]Kinetic properties with ABTS used as the substrate.
[b]Kinetic properties with guaiacol used as the substrate.
[c]Kinetic properties with 2,6-DMP used as the substrate.

(v) Lignin Degradation and Dye Decoloration Analysis

Figure 4:
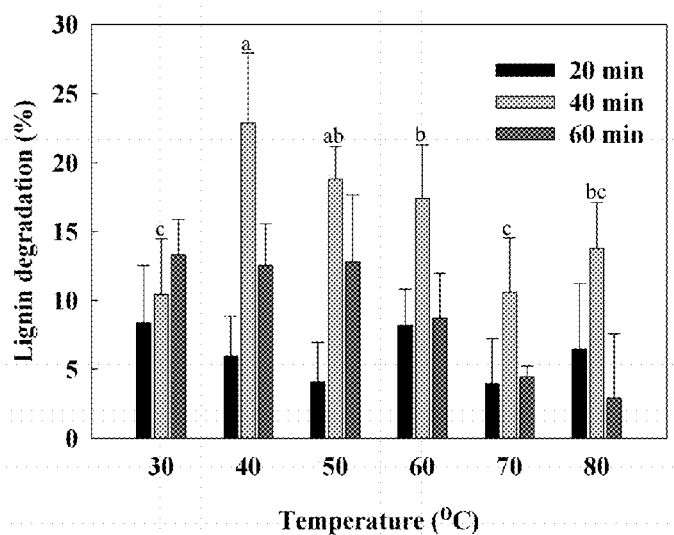
FIG. 4 is a chart showing lignin degradation (panel A) and RBBR decoloration (panel B) by crude laccase fraction from *Cerrena* sp. WR1 or by Lcc3.
Figure 4:
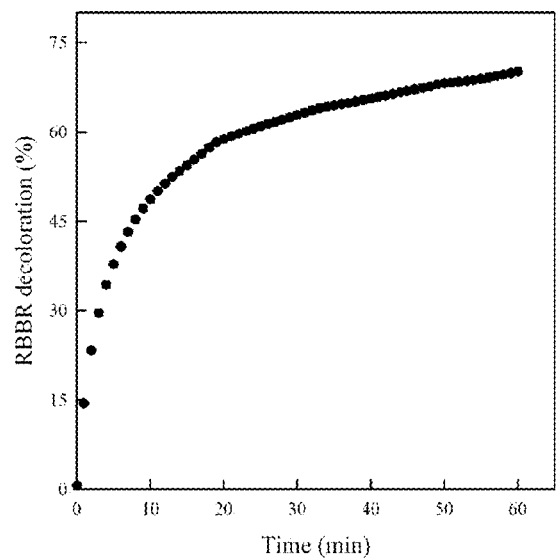

Lignin degradation reaction was carried out by mixing a crude laccase broth (containing 100 U enzyme) with 50 ml reaction buffer (50 mM citric acid solution; pH 3.0) containing 100 mg smashed rice straw materials. The mixture was incubated at 30-80° C. for 20-60 min. Sodium azide was added to the mixture at a final concentration of 1 mM to stop the enzymatic reaction. The processed rice straw was collected by filtration and dried at 60° C. The lignin contents in the rice straw before and after treatment were determined following the method described in kappa number of ISO 302:2004 (International Organization for Standardization). The results were shown in FIG. 4, panel A. The highest lignin degradation efficiency per 100 U is Lcc3 was around 22.9%, which was observed when performing the degradation reaction at 40° C. for 40 min.

Dye decoloration reaction was performed by mixing a partially purified laccase broth (containing 8 U enzyme) with a 1 ml reaction buffer (50 mM citric acid solution; pH 3.0) containing 0.02% RBBR (Sigma). The mixture was incubated at 20° C. for 1 h. Dye decoloration was determined by monitoring the change in absorbance at 595 nm and the dye decoloration efficiency (%) was defined as the relative amount of dye reduced after the treatment. See FIG. 4, panel B. Lcc3 exhibited 70.1% decoloration efficiencies against RBBR at 20° C.

(vi) Cloning of Laccase Genes from Cerrena sp. WR1 and Expressing Laccases in Pichia Mycelia of Cerrena sp. WR1, after being cultured in PDB for 13 days, were harvested by paper filtration and ground in liquid nitrogen. Total RNA was isolated from the mycelia using the RNeasy® Mini Kit (Qiagen). The first pool of cDNA fragments was obtained by RT-PCR with the SuperScript® III RTS First-Strand cDNA Synthesis Kit (Invitrogen). The Cerrena sp. WR1 laccase genes were then amplified using two degenerate primers LAC-N1 (5'-CAYTGGCAYGGNTTYTTYCA-3'; SEQ ID NO:27) and LAC-C1 (5'-TGRAARTCDATRTGRCARTG-3'; SEQ ID NO:28). These two primers were designed based on the sequences in highly conserved copper-binding regions I and IV in fungal laccases. See Hoshida et al., The Society for Biotechnology, Japan, 92(4):372-380. The PCR products were cloned into a vector plasmid, using the Zero Blunt® TOPO® PCR Cloning Kit (Invitrogen), and subjected to sequencing analysis to determine the full-length cDNA sequences coding for the laccases.

Three Cerrena sp. WR1 laccase genes, i.e., lcc1, lcc2, and lcc3, were identified. lcc1 cDNA (SEQ ID NO:19), including 1,557 bp, encodes a polypeptide of 518 amino acid residues (SEQ ID NO:7); the lcc2 cDNA (SEQ ID NO:20), including 1,554 bp, encodes a polypeptide of 517 amino acid residues (SEQ ID NO:8); and the lcc3 cDNA (SEQ ID NO:21), including 1,551 bp, encodes a polypeptide of 516 amino acid residues (SEQ ID NO:9). Each of the three polypeptides are in precursor form including a 21-amino-acid long signal peptide at its N-terminus.

The EasySelect™ Pichia Expression System (Invitrogen) was used in this study for expression of Lcc1, Lcc2, and Lcc3 laccases. cDNA fragments coding for these three laccases were cloned into Pichia expression vector pPICZA or pPIC- ZαB via EcoRI and NotI restriction sites. More specifically, the lcc1 ene coding for Lcc1 precursor (including a signal peptide sequence) was cloned into pPICA to generate expression plasmid pPICZA-lcc1 and the lcc2 and lcc3 genes coding for mature Lcc2 and Lcc3 were cloned into pPICZαB to obtain expression plasmids pPICZαB-lcc2 and pPICZαB-lcc3, respectively. The three expression plasmids were introduced into *P. pastoris* X-33 cells following the method described in Invitrogen's protocol. Positive transformants were cultured in BMMY (1% yeast extract, 2% peptone, 100 mM potassium phosphate, pH 6.0, 1.34% yeast nitrogen base, 0.00004% biotin, and 0.5% methanol) at 25° C., 200 rpm for 12-26 days. Methanol was added to the culture media daily to reach a final concentration of 0.5%. During the cultivation, 1 ml of the supernatant was collected at various time points. The laccase activity and cell density in the supernatant were determined following the method described above or routine procedures.

Figure 5:
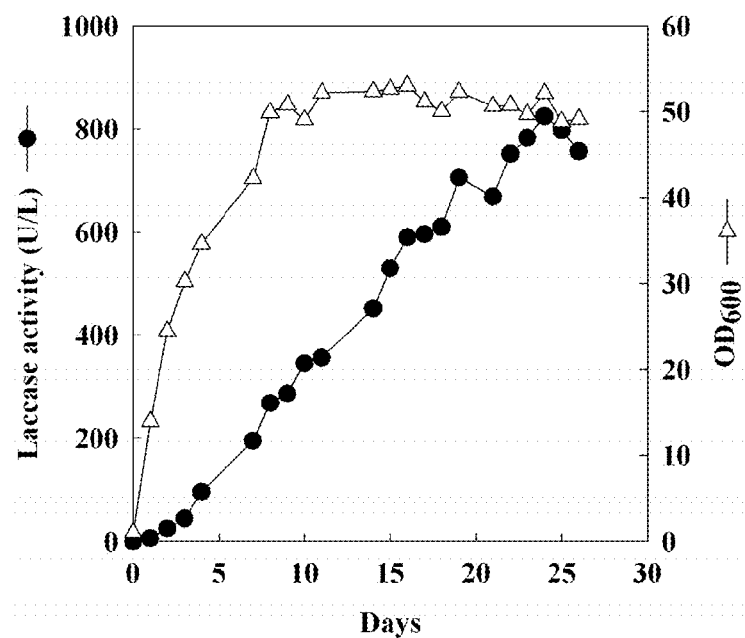
FIG. 5 is a diagram showing production of Lcc1, Lcc2, and Lcc3 in *P. pastoris* host cells via recombinant technology and growth curves of the host cells. Panel A: Lcc1; Panel B; Lcc2, and Panel C: Lcc3.
Figure 5:
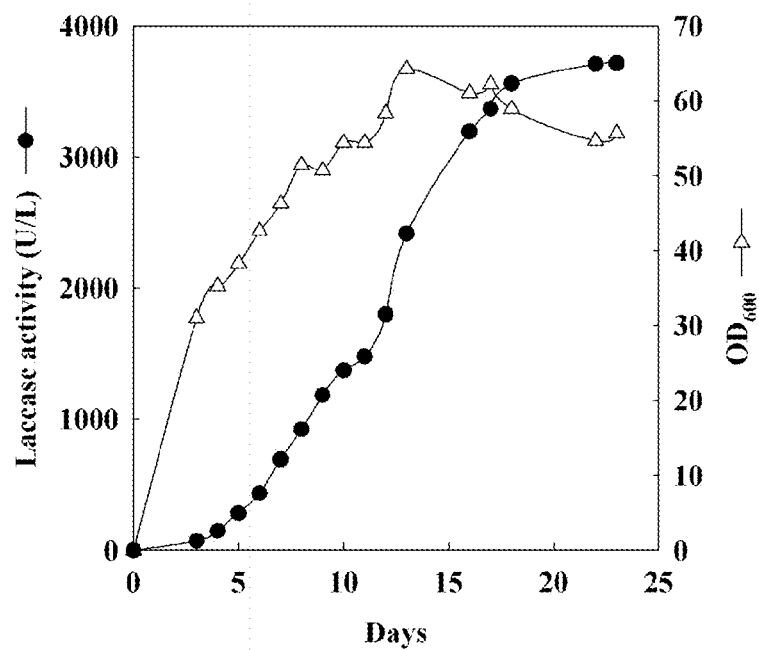
Figure 5:
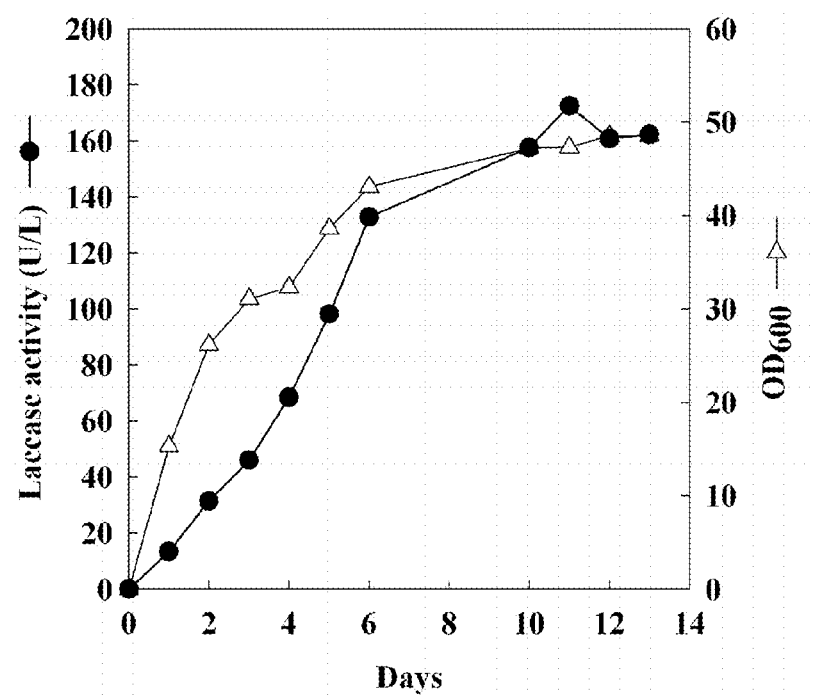

Precursor Lcc1 and mature Lcc2 and Lcc3 were successfully expressed in *P. pastoris* strain X-33 via routine procedures. As shown in FIG. 5, approximately 800 U/L (Lcc1), 160 U/L (Lcc2), and 3700 U/L (Lcc3) were observed in culture media after 13-26 day cultivation.

Example 2

Isolation and Characterization of Three Novel Laccases from *Lentinus* sp (i) *Lentinus* sp. Cultivation and Laccase Production A target *Lentinus* sp. strain was maintained on a potato dextrose agar (PDA) plate following routine procedures. A mycelium from the slant was transferred to a fresh PDA plate and incubated at 28° C. for 5 days. The resulting mycelial discs from the peripheral region of an actively growing colony were used as an inoculum.

Figure 6:
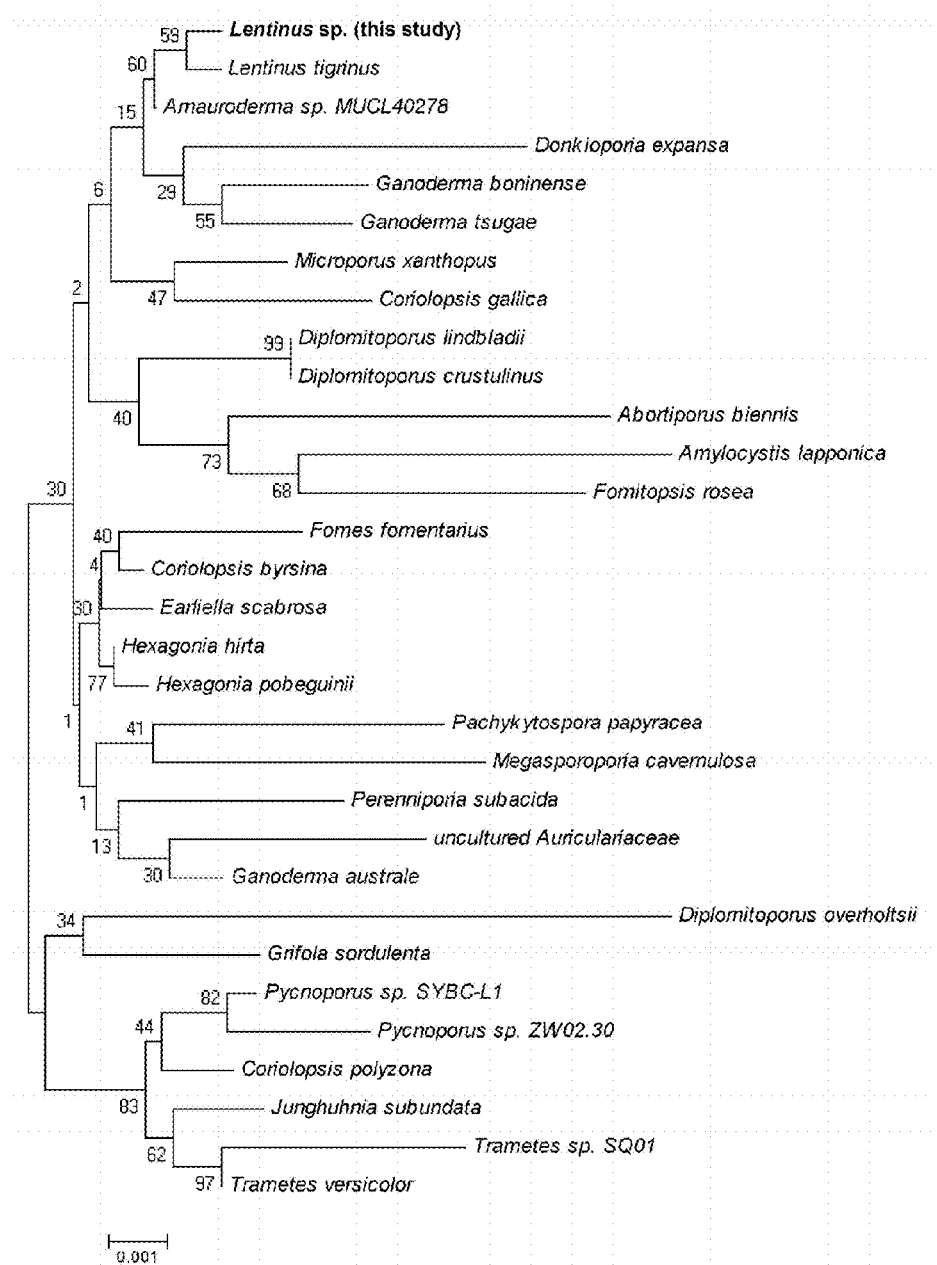
FIG. 6 is a diagram showing the phylogenetic relationship between *Lentinus* sp. and other fungal strains. Bootstrap values at nodes refer to the percentage of 500 replicates. Scale bar: base substitutions per 100 bases.

The phylogeny of the target *Lentinus* sp. strain was determined based on its 18S rDNA sequence, following the method described in Example 1 above. Briefly, DNA fragments encoding 18S rRNA were obtained by PCR as described above. The resultant DNA fragments, including 1783 bp, were confirmed by double-strand DNA sequencing as coding for the 18S rRNA. The rDNA sequence thus obtained was compared with other fungal 18S rDNA sequences obtained from the GenBank database via the Clustal method using the MEGA 4.1 software (DNASTAR, Madison, Wis.). The alignment result was then analyzed with the same software for calculation of distance matrix. Neighbor-joining correction of distances was used to construct a phylogenetic tree, shown in FIG. 6.

The result indicate that the target *Lentinus* sp. strain in the current study was closest to the species of *Lentinus tigrinus* (GenBank accession no. AY946269), with 99.2% 18S rDNA sequence identity as determined by the neighbor-joining method.

(ii) Protein Purification and Characterization

A *Lentinus* sp. strain inoculum, prepared as described above, was inoculated into a medium containing 2.4% potato dextrose broth, 5% soytone, and 0.4 mM $CuSO_4$ and cultured at 25° C. and 150 rpm for 18 days. Three days after inoculation, 2,5-xylidine was added to a final concentration of 2 mM as an inducer for laccase production. During the cultivation, 1 ml of the supernatant was collected at various time points and the laccase activity/protein concentration in the supernatant was determined as described in Example 1 above. More than 90% of the laccase proteins were found to be secreted into the culture medium.

After the 18-day cultivation, the culture medium was collected and concentrated using the Labscale™ TFF System (Millipore, Billerica, Mass.) with a 10K Pellicon®-XL filter. The filtrate was dialyzed against a 50 mM sodium phosphate buffer (pH 6.0), and then purified using two sequential Q Sepharose columns (2.6×30.0 cm, GE Healthcare, Uppsala, Sweden), both of which were pre-equilibrated with the same buffer. Proteins were eluted with a 0-1.0 M NaCl gradient in a 50 mM sodium phosphate buffer (pH 6.0) at a flow rate of 0.5 ml/min. The fractions exhibiting laccase activity were pooled and dialyzed against a 50 mM sodium phosphate buffer (pH 6.0) containing 1.0 M NaCl and then concentrated with an Amicon Ultra-15 centrifugal filter device (Millipore). A final gel filtration purification procedure using a Superdex 200 column (GE Healthcare) (1.6×90 cm, flow rate: 0.2 ml/min) was performed to obtain a purified laccase protein fraction with >96% homogeneity as determined by SDS-PAGE.

Zymography analysis was performed as described above to determine laccase activity. The exact mass of the purified laccase was determined by use of Thermo Finnegan ProteomeX LTQ (LC-ESI-MS/MS) (Thermo, Mass.) at the Proteomics Core Laboratory, Institute of Plant and Microbial Biology, Academia Sinica, Taiwan. The purified laccase was also subjected to Glycoprotein analysis following the method described in Example 1 above.

Figure 7:
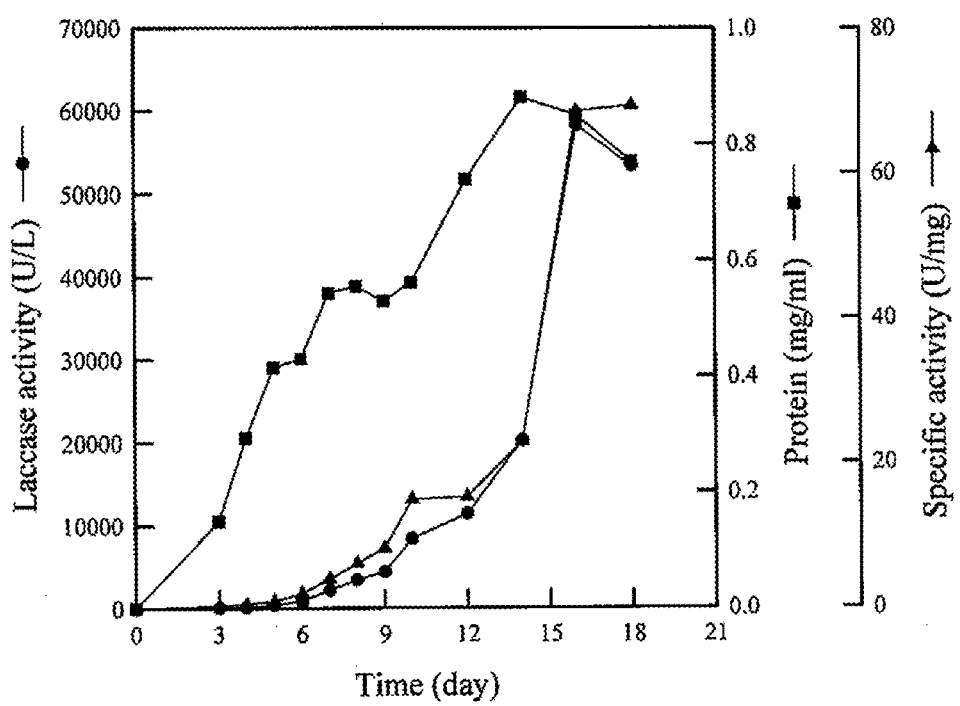
FIG. 7 is a chart showing a time course of laccase activities, protein levels, and specific activities during a 13-day fermentation period of *Lentinus* sp.
Figure 8:
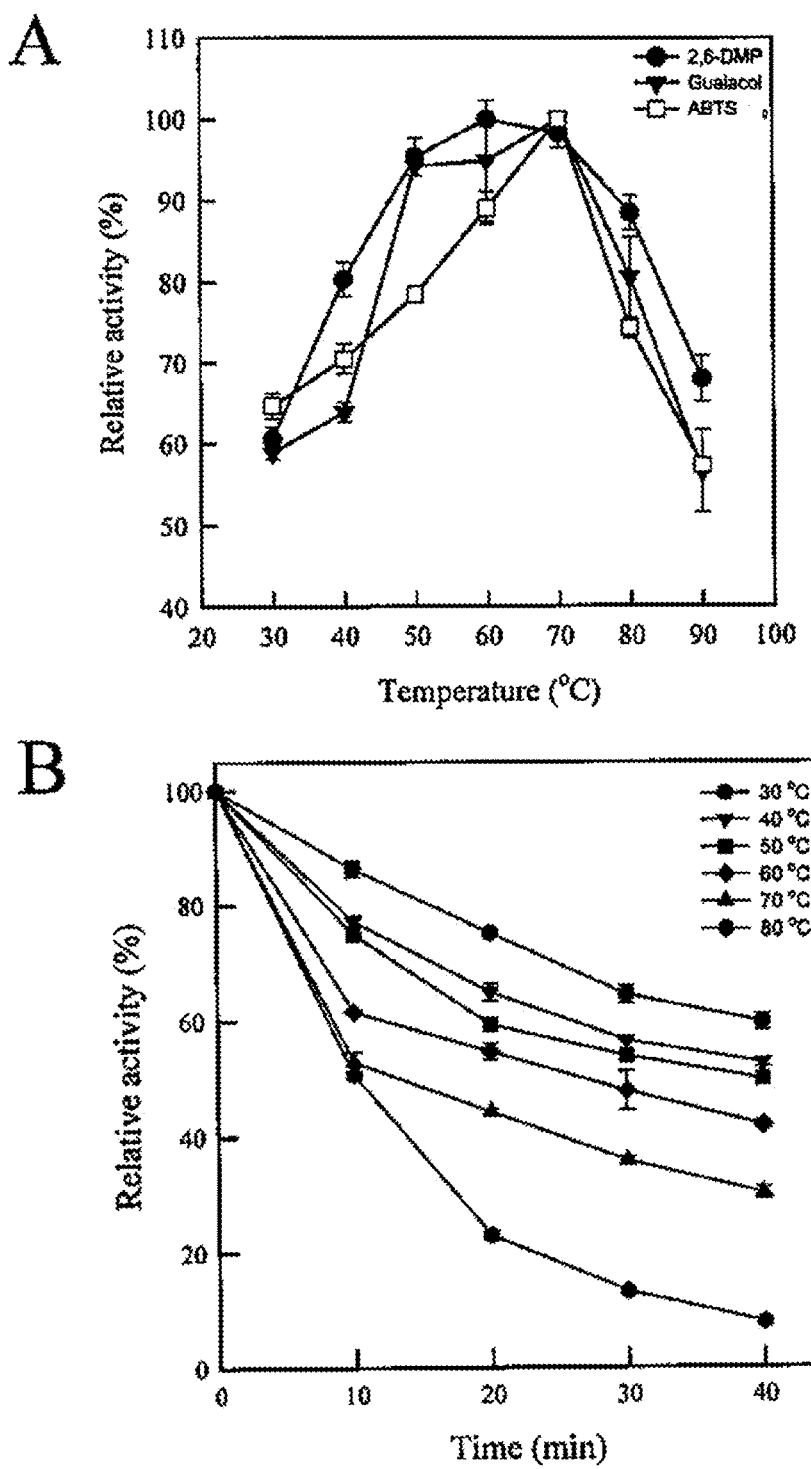
FIG. 8 is a diagram showing the effects of temperature and pH on activity and stability of *Lentinus* sp. laccases. Panel A: effect of temperature on laccase activity; Panel B: effect of temperature on laccase stability; Panel C: effect of pH on laccase activity; Panel D: effect of pH on laccase stability.
Figure 8:
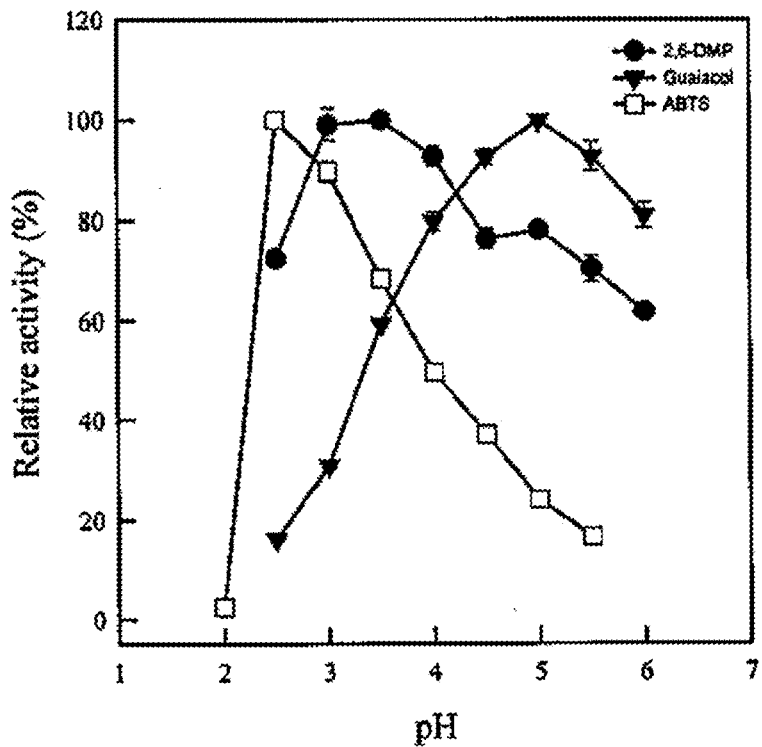
Figure 8:
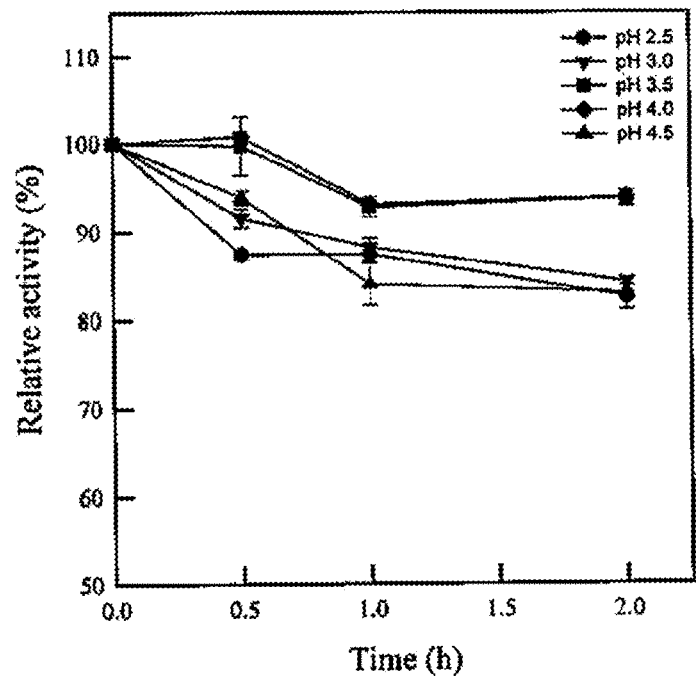

The optimized laccase production in liquid culture of *Lentinus* sp. is shown in FIG. 7. After a 16-day cultivation at 25° C., the laccase activity in the culture medium peaked at approximately 58,273 U/L, and the specific activity in the medium reached around 68.6 U/mg. See FIG. 7. Further, laccase was enriched about 35.1-fold with a 3.6% yield after the anion-exchange and gel-filtration column chromatography. The specific activity of the enriched laccase fraction (with >96% homogeneity) was determined to be 1427.1 U/mg at 30° C. and pH 3.0. The results obtained from the zymography analysis and glycoprotein analysis of the purified *Lentinus* sp. laccase indicate that this enzyme has a molecule weight of 59.1 (glycosylated) and 55.2 kDa (deglycosylated). The glycosylation level in the enzyme was about 6.6%. UV-Vis absorption spectral analysis showed that the purified enzyme has a dominant absorption peak at 600 nm and a broad shoulder absorption at 330 nm, indicating that this enzyme contains both type I and type III copper ions. Results from a DSC assay as described above show that the *Lentinus* sp. laccase denatured at a high temperature, with a midpoint temperature ($T_m$) of 77.1° C.

(iii) Effect of Temperature, pH, and Solvent on Laccase Activity and Stability

To determine the effect of temperature on the enzyme activity, a standard enzymatic activity assay was performed under various temperatures (i.e., 30-90° C.). For thermal stability study, laccase was pre-incubated in a 50 mM citric acid buffer (pH 3.0) at 30-80° C. for 10-40 min and the residual enzymatic activity was then determined by the standard assay. See Example 1 above. Values of $t_{1/2}$ were determined accordingly.

The results show that the optimal temperature for the *Lentinus* sp. laccase was 70° C. when ABTS or guaiacol was used as the substrate and the optimal temperature was 60° C. when 2,6-dimethoxyphenol (2,6-DMP) was used as the substrate. Values of $t_{1/2}$ at 50° C., 60° C., and 70° C. were 30 min, 20 min, and 15 min, respectively. When determined at 30° C. or 40° C., the $t_{1/2}$ value was greater than 40 min. The $t_{1/2}$ of the enzyme incubated at room temperature (25° C.) in 50 mM sodium phosphate buffer was around 118 h.

The effect of pH on laccase activity was investigated at pH 2.0-6.0, using a glycine-HCl buffer (pH 2.0-2.5) or a citric acid buffer (pH 2.5-6.0). To determine protein stability in different pH conditions, the enzyme was pre-incubated at pH 2.5-4.5 at 25° C. for 0-2 h and the residual enzyme activity was determined by the standard enzymatic assay.

The purified *Lentinus* sp. laccase showed a maximal activity at pH 2.5, 3.5, and 5.0 when ABTS, 2,6-DMP, and guaiacol, respectively, were used as the substrates. This enzyme was also found to be very stable under acidic conditions. More specifically, it remained more than 80% of its original activity against ABTS after being incubated at pH 2.5-4.5 for 2 h.

The enzyme stability in the presence of an organic solvent was investigated as follows. The purified *Lentinus* sp. laccase was pre-incubated in 50 mM sodium phosphate buffer (pH 6.0) containing 1%, 10%, or 25% of an organic solvent (i.e., methanol, ethanol, acetonitrile; acetone, and N,N-dimethyl formamide) at room temperature for up to 120 hours. *T. versicolor* (Fluka No. 53739) laccase was used as a reference enzyme in this study. The residual enzymatic activity was determined at different time intervals during the incubation by the standard assay. The results are shown in Table 3 below:

TABLE 3

Effects of various organic solvents on *Lentinus* sp. laccase activity

| Organic solvents | Relative activity (%)* | |
|---|---|---|
| | 1% | 10% |
| Methanol | 101.4 ± 6.4 | 101.0 ± 4.1 |
| Ethanol | 103.6 ± 8.7 | 88.3 ± 3.9 |
| Acetone | 69.2 ± 3.0 | 62.8 ± 2.9 |
| Acetonitrile | 91.8 ± 1.7 | 86.4 ± 6.8 |
| N,N-Dimethylformamide | 79.9 ± 5.0 | 56.3 ± 5.4 |
| Dimethyl sulfoxide | 78.4 ± 6.1 | 1.5 ± 0.8 |

*Assay reactions were performed in 50 mM citric acid buffer (pH 3.0) at 30° C., with ABTS used as the substrate.

The laccase stability after incubation with methanol or ethanol for an extended period was further investigated. The *Lentinus* sp. laccase or the reference laccase was incubated with 1-25% methanol or ethanol in a 50 mM sodium phosphate buffer (pH 6.0) at room temperature for up to 120 hours and enzymatic activities were determined at various time intervals during the incubation, using ABTS as the substrate. Surprisingly, the *Lentinus* sp. laccase showed an increased enzymatic activity (i.e., 149%) 6 hours after incubation with 10% of methanol or ethanol. The enzyme activity of the *Lentinus* sp. laccase maintained as 95% in 25% ethanol while that of the reference laccase reduced to 41%. This result indicates that the *Lentinus* sp. laccase is resistant to ethanol/methanol, rendering it an ideal candidate enzyme for use in the biofuel industry.

(iv) Laccase Kinetics

Kinetic parameters were determined following conventional methods. See also Example 1 above. The results are shown in Table 4 below:

TABLE 4

Kinetic properties of laccases from various microorganisms

| Fungal Species | Specific activity (U/mg) | $k_{cat}$ ($s^{-1}$) | $K_m$ (μM) | $k_{cat}/K_m$ ($s^{-1}\mu M^{-1}$) | Optimum temperature (° C.) | $t_{1/2}$ (min) |
|---|---|---|---|---|---|---|
| *Lentinus* sp.[a] | 2047.1 | 2016.5 | 8.4 | 239.5 | 70 (at pH 2.5) | >40 (at 50° C.) 15 (at 70° C.) |
| *Lentinus* sp.[b] | 310.3 | 305.5 | 523.5 | 0.58 | 70 (at pH 5.0) | — |
| *Lentinus* sp.[c] | 123.8 | 121.9 | 434.5 | 0.28 | 60 (at pH 3.5) | — |
| *Coriolus versicolor*[a] (Sigma No. 38837) | 0.3 | — | — | — | 25 (at pH 4.5) | — |
| *Trametes versicolor*[a] (Fluka No. 53739) | 750 | — | — | — | 50 (at pH 3.0) | 15 (at 50° C.) 5 (at 70° C.) |
| *Melanocarpus* sp.[a] (US 7,183,090 B2) | 42.45 | — | — | — | 70 (at pH 6.0) | >360 (at 50° C.) <15 (at 70° C.) |
| *Agaricus blazei*[a] | 174.6 | 21 | 63 | 0.33 | 25 (at pH 2.3) | >250 (at 25° C.) |
| *Panus tigrinus*[a] | — | 185.69 | 31 | 5.99 | 30 (at pH 3.5) | 150 (at 25° C.) |
| *Pleurofus sajor-caju*[a] | 1244.4 | 520.24 | 56 | 9.29 | 40 (at pH 5.0) | — |
| *Pycnoporus sanguineus*[a] | 340.76 | 1.155 | 77 | 0.015 | 25 (at pH 3.0) | — |
| *Trametes* C30 LAC2[a] | 934 | 683.33 | 536 | 1.27 | 55 (at pH 5.7) | — |
| *Trametes pubescens* LAP2[a] | 1100 | 350 | 43 | 8.14 | 25 (at pH 4.0) | — |
| *Trametes versicolor*[a] | 310.0 | 351.3 | 37.3 | 9.4 | 55 (at pH 4.0) | — |

(v) Lignin Degradation and Decoloration Analysis

Figure 9:
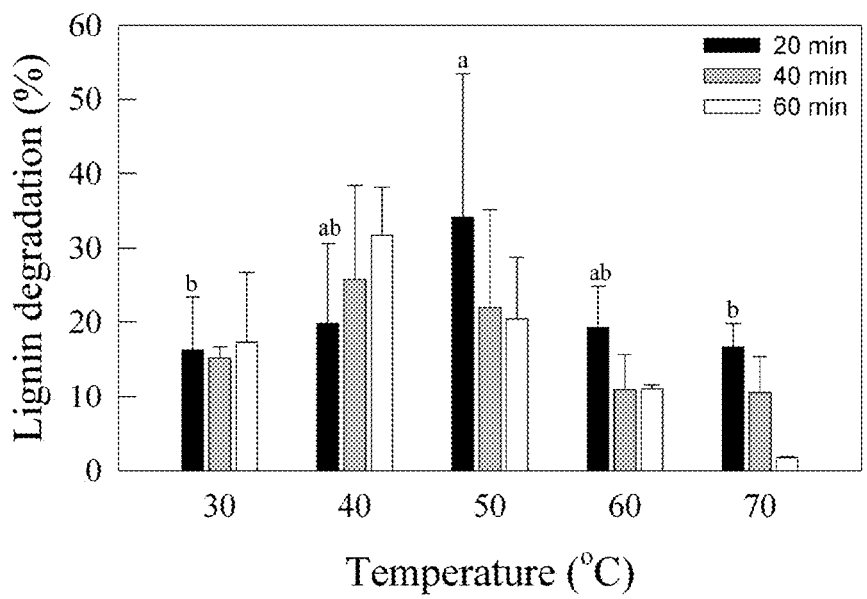
FIG. 9 is a chart showing lignin degradation (panel A) and RBBR decoloration (panel B) by crude laccase fraction from *Lentinus* sp.
Figure 9:
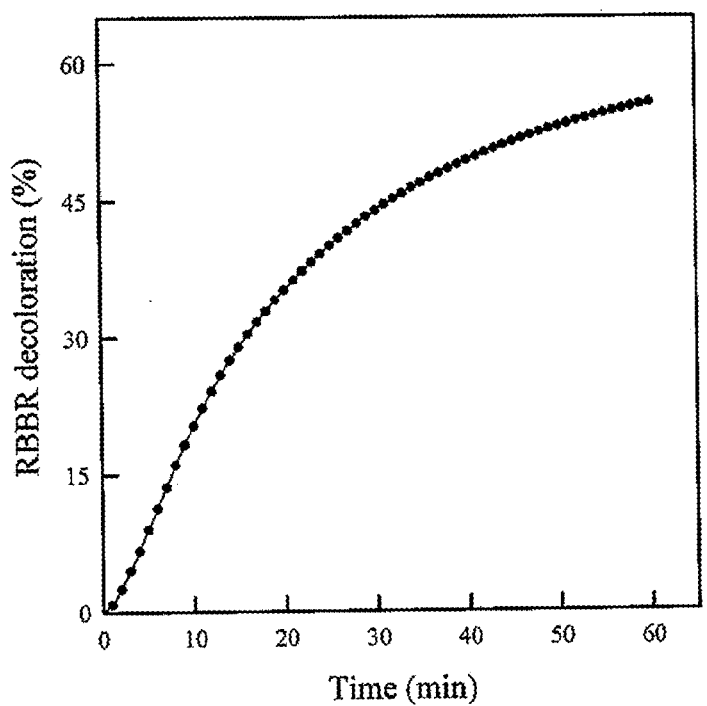

The lignin degradation reaction and the dye decoloration reaction were carried out following the methods described in Example 1 above. The results show that the highest lignin degradation efficiency, i.e., 34.1%, was observed when the reaction was carried out at 50° C. for 20 min. See FIG. 9, pane A. The lignin degradation efficiencies were 22%-25% at 40-50° C. for 40 min and 32% at 40° C. for 60 min. See FIG. 9, panel A. The results also show that the highest RBBR decoloration efficiency is around 47.7%. See FIG. 9, panel B.

(vi) Cloning of Laccase Genes from *Lentinus* sp. and Expressing Laccases in *Pichia*

Total RNAs from *Lentinus* sp. were isolated and cDNAs encoding laccases were amplified via PCR, following the methods described in Example 1 above. Full-length laccase cDNAs were then amplified using the following specific primers:

```
lcc5-1:
                                      (SEQ ID NO: 29)
5'-GCGACGTGATACCAATCGGCGAGAGTTA-3';

lcc5-2:
                                      (SEQ ID NO: 30)
```

```
          -continued
5'-CCATGCTGAAATCCACAAGTATCCACTG-3';

lcc3-1:
                                       (SEQ ID NO: 31)
5'-CCTAACCTGCGCATCGGCTTCCCCCAGC-3';
and lcc3-2:
                                       (SEQ ID NO: 32)
5'-CGCAAAAACCCTGCGTCCGCATTACCCAGC-3'.
```

Three *Lentinus* sp. laccase genes, designated lccA (SEQ ID NO: 22; GenBank accession no. FJ693715), lccB (SEQ ID NO: 23; GenBank accession no. FJ693716), and lccC (SEQ ID NO: 24; GenBank accession no. GQ220322), were identified. lccA includes 1,566 by and encodes a polypeptide of 521 amino acid residues (SEQ ID NO:10); lccB gene includes 1,467 by and encodes a polypeptide of 488 amino acid residues (SEQ ID NO:11); lccC gene includes 1,566 by and encodes a polypeptide of 521 amino acid residues (SEQ ID NO:12). All of the encoded polypeptides are in precursor form, i.e., including a 21-amino-acid signal peptide at the N-terminus.

The full-length *Lentinus* sp. lccA gene was amplified via PCR using primers lcc1-F: 5'-TTCGAAACGAGGAATTC-CCACCATG-3' (SEQ ID NO: 33) and lcc1-R: 5'-TTCTA-GATCCTGATCATCAGAACTG-3' (SEQ ID NO: 34). The PCR product was cloned into the *Pichia* expression vector pPICZB (Invitrogen) via the EcoR1 and Xba1 cloning sites to obtain an expression plasmid pPICZ-lccA.

pPICZ-lccA was introduced into *Pichia pastoris* strain X-33 host cells (Invitrogen) and positive transformants were selected for LccA expression. Briefly, a positive transformant was cultured in BMMY medium containing 1% yeast extract, 2% peptone, 1.34% yeast nitrogen base, 0.00004% biotin, and 0.5% methanol at 25° C. and 200 rpm for 20 days. Methanol was daily added to reach a final concentration of 0.5%. Within the 20-day cultivation, 1 ml of the supernatant was collected; laccase activity and cell growth were determined.

Figure 10:
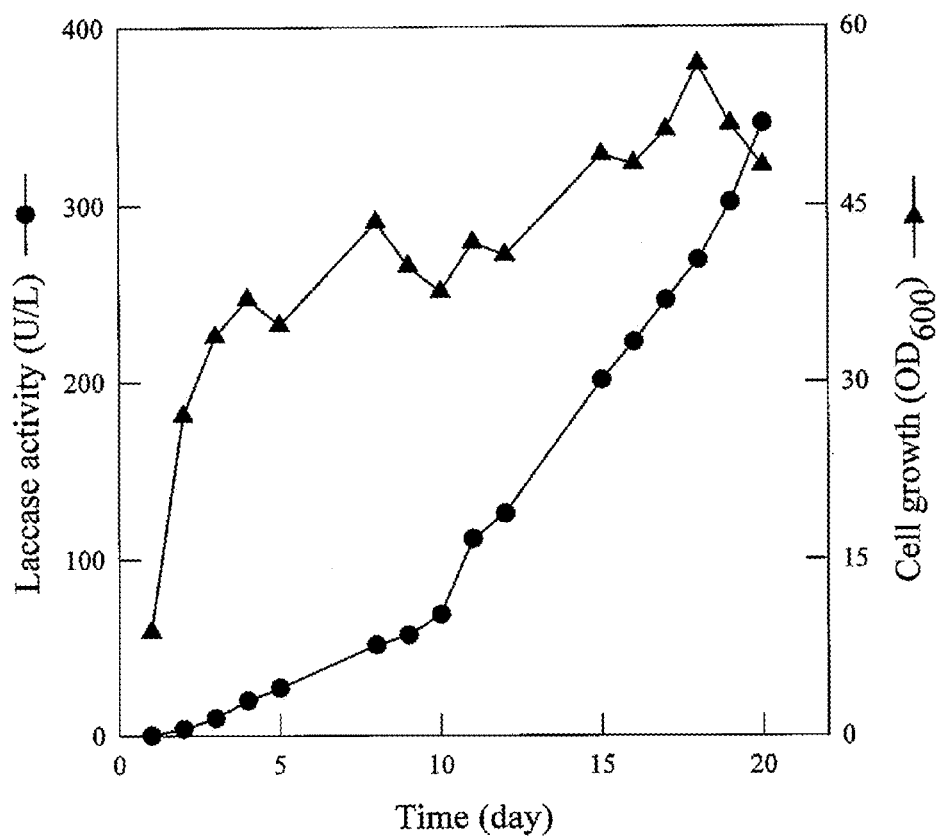
FIG. 10 is a diagram showing production of LccA in *P. pastoris* host cells via recombinant technology and growth curves of the host cells.

As shown in FIG. 10, a high laccase activity (about 400 U/L) was detected in the culture medium after 18-day cultivation, indicating that the expressed LccA was secreted into the medium.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated polypeptide, comprising an amino acid sequence that is at least 95% identical to the sequence of SEQ ID NO:6, the polypeptide having four conserved laccase copper binding sites, and wherein the sequence of the polypeptide and the sequence of SEQ ID NO:6 have identical residues at positions corresponding to residues 193-201, 203-208, 211-216, 274-281, 348-356, and 436-442 of the sequence of SEQ ID NO:6, and wherein the polypeptide exhibits laccase enzymatic activity.

2. The isolated polypeptide of claim 1, comprising the amino acid sequence of SEQ ID NO:6.

3. The isolated polypeptide of claim 2, comprising the amino acid sequence of SEQ ID NO:12.

4. A method of oxidizing a laccase substrate, comprising contacting the isolated polypeptide of claim 1 with a laccase substrate.

5. The method of claim 4, wherein the substrate is selected from the group consisting of hardwood stem, softwood stem, nut shell, corn cob, paper, straw, sorted refuse, leaf, cotton seeds hair, swine waste, cattle manure, grass, sugar cane bagasse, bamboo, fiber, coffee pulp, banana waste, and yucca waste.

6. The method of claim 4, wherein the substrate is an aromatic dye, an industrial effluent, an environmental contaminant, or a toxic compound.

7. The method of claim 4, wherein the polypeptide contains the amino acid sequence of SEQ ID NO: 6.

* * * * *

SEQUENCE LISTING

```
<160> NUMBER OF SEQ ID NOS: 34

<210> SEQ ID NO 1
<211> LENGTH: 497
<212> TYPE: PRT
<213> ORGANISM: Cerrena sp

<400> SEQUENCE: 1

Ala Ile Gly Pro Val Thr Asp Leu Glu Ile Thr Asn Gly Thr Ile Ser
1               5                   10                  15

Pro Asp Gly Tyr Ser Arg Ala Ala Val Leu Ala Gly Gly Ser Phe Pro
            20                  25                  30

Gly Pro Leu Ile Thr Gly Asn Lys Ser Asp Asn Phe Gln Ile Asn Val
        35                  40                  45

Val Asn Ser Leu Ala Asp Ser Asp Met Leu Lys Ser Thr Thr Val His
    50                  55                  60

Trp His Gly Phe Phe Gln Lys Gly Thr Asn Trp Ala Asp Gly Pro Ala
65                  70                  75                  80

Phe Val Asn Gln Cys Pro Ile Ala Thr Gly Asn Ser Phe Leu Tyr Asn
                85                  90                  95

Phe Asn Ala Thr Asp Gln Ala Gly Thr Phe Trp Tyr His Ser His Leu
            100                 105                 110

Glu Thr Gln Tyr Cys Asp Gly Leu Arg Gly Pro Met Val Val Tyr Asp
        115                 120                 125

Pro Asp Asp Pro His Ala Asp Leu Tyr Asp Val Asp Asp Ser Thr
    130                 135                 140

Val Ile Thr Leu Ala Asp Trp Tyr His Thr Leu Ala Arg Leu Gly Ala
145                 150                 155                 160

Ala Phe Pro Thr Ser Asp Ala Thr Leu Ile Asn Gly Leu Gly Arg Tyr
```

```
                            165                 170                 175
Ser Asp Gly Asn Thr Thr Asp Leu Ala Val Ile Thr Val Glu Ser Gly
                180                 185                 190

Lys Arg Tyr Arg Phe Arg Leu Val Ser Ile Ser Cys Asp Pro Asn Phe
            195                 200                 205

Thr Phe Ser Ile Asp Asn His Thr Met Thr Ile Ile Glu Ala Asp Ala
        210                 215                 220

Val Asn Tyr Thr Pro Leu Asp Val Asp Glu Ile Gln Ile Phe Ala Gly
225                 230                 235                 240

Gln Arg Tyr Ser Phe Ile Leu Thr Ala Asn Gln Thr Val Asp Asn Tyr
                245                 250                 255

Trp Ile Arg Ala Asp Pro Asn Val Gly Thr Thr Gly Phe Asp Asn Gly
            260                 265                 270

Ile Asn Ser Ala Ile Leu Arg Tyr Ser Gly Ala Asp Glu Val Glu Pro
        275                 280                 285

Thr Thr Asn Gln Thr Thr Ser Thr Asn Pro Leu Val Glu Ala Asn Leu
    290                 295                 300

Val Pro Leu Asp Gly Ala Ala Pro Gly Glu Ala Val Ala Gly Gly
305                 310                 315                 320

Val Asp Tyr Ala Leu Asn Leu Ala Leu Ala Phe Asp Gly Thr Asn Leu
                325                 330                 335

Asp Phe Thr Val Asn Gly Tyr Glu Tyr Thr Ser Pro Thr Pro Val
            340                 345                 350

Leu Leu Gln Ile Leu Ser Gly Ala Ser Ser Val Asp Asp Leu Leu Pro
        355                 360                 365

Ser Gly Ser Ile Tyr Ser Leu Pro Ser Asn Ser Thr Ile Glu Leu Ser
    370                 375                 380

Ile Pro Ala Leu Ala Val Gly Ala Pro His Pro Ile His Leu His Gly
385                 390                 395                 400

His Thr Phe Ser Val Val Arg Ser Ala Gly Ser Thr Thr Tyr Asn Tyr
                405                 410                 415

Asp Asn Pro Pro Arg Arg Asp Val Val Ser Ile Gly Thr Ala Thr Asp
            420                 425                 430

Asp Asn Val Thr Ile Arg Phe Thr Thr Asp Asn Pro Gly Pro Trp Phe
        435                 440                 445

Leu His Cys His Ile Asp Phe His Leu Glu Ala Gly Phe Ala Val Val
    450                 455                 460

Phe Ala Glu Asp Phe Asn Asp Thr Ala Ser Ala Asn Thr Val Thr Thr
465                 470                 475                 480

Glu Trp Ser Asp Leu Cys Thr Thr Tyr Asp Ala Leu Ser Ser Asp Asp
                485                 490                 495

Leu

<210> SEQ ID NO 2
<211> LENGTH: 496
<212> TYPE: PRT
<213> ORGANISM: Cerrena sp

<400> SEQUENCE: 2

Ala Ile Gly Pro Val Thr Asp Leu Thr Ile Thr Asn Ala Thr Ile Ser
1               5                   10                  15

Pro Asp Gly Phe Ser Arg Gln Ala Val Leu Ala Gly Gly Val Phe Pro
                20                  25                  30

Gly Pro Leu Ile Thr Gly Asn Lys Gly Asp Asn Phe Gln Ile Asn Val
            35                  40                  45
```

```
Val Asn Ser Leu Glu Asn Ser Asp Met Leu Lys Ser Thr Thr Ile His
 50                  55                  60

Trp His Gly Phe Phe Gln Lys Gly Thr Asn Trp Ala Asp Gly Pro Ala
65              70                  75                  80

Phe Val Asn Gln Cys Pro Ile Ala Thr Gly Asn Ser Phe Leu Tyr Asn
                 85                  90                  95

Phe Asn Ala Asp Asp Gln Ala Gly Thr Phe Trp Tyr His Ser His Leu
            100                 105                 110

Ser Thr Gln Tyr Cys Asp Gly Leu Arg Gly Pro Met Val Val Tyr Asp
        115                 120                 125

Pro Asn Asp Pro His Ala Ser Leu Tyr Asp Val Asp Asp Glu Ser Thr
    130                 135                 140

Val Ile Thr Leu Ala Asp Trp Tyr His Thr Leu Ala Arg Leu Gly Ala
145                 150                 155                 160

Ala Phe Pro Thr Ala Asp Ala Thr Leu Ile Asn Gly Leu Gly Arg Tyr
                165                 170                 175

Ser Asp Gly Thr Thr Ser Asp Leu Ala Val Ile Thr Val Glu Ser Gly
            180                 185                 190

Lys Arg Tyr Arg Phe Arg Leu Val Asn Ile Ser Cys Asp Pro Asn Tyr
        195                 200                 205

Thr Phe Ser Ile Asp Asn His Thr Phe Thr Val Ile Glu Val Asp Gly
    210                 215                 220

Val Asn His Ala Ala Leu Asp Val Asp Glu Ile Gln Ile Phe Ala Gly
225                 230                 235                 240

Gln Arg Tyr Ser Phe Val Leu Thr Ala Asn Gln Thr Val Asp Asn Tyr
                245                 250                 255

Trp Ile Arg Ala Asn Pro Asn Leu Gly Thr Thr Gly Phe Asp Asn Gly
            260                 265                 270

Ile Asn Ser Ala Ile Leu Arg Tyr Ser Gly Ala Asn Glu Thr Glu Pro
        275                 280                 285

Thr Thr Thr Gln Thr Thr Ala Thr Ala Leu Ser Glu Ala Ser Leu
    290                 295                 300

Val Pro Leu Glu Asp Pro Ala Ala Pro Gly Glu Ala Val Ala Gly Gly
305                 310                 315                 320

Val Asp Tyr Ala Leu Asn Leu Ala Phe Ala Phe Asp Gly Ala Asn Leu
                325                 330                 335

Asp Phe Thr Val Asn Gly Glu Thr Tyr Val Ser Pro Thr Val Pro Val
            340                 345                 350

Leu Leu Gln Ile Leu Ser Gly Ala Ser Ser Val Ser Asp Leu Leu Pro
        355                 360                 365

Ala Gly Ser Val Tyr Ser Leu Pro Ser Asn Ser Thr Ile Glu Leu Ser
    370                 375                 380

Met Pro Gly Gly Val Val Gly Gly Pro His Leu His Leu His Gly
385                 390                 395                 400

His Ala Phe Ser Val Val Arg Ser Ala Gly Ser Asp Thr Tyr Asn Tyr
                405                 410                 415

Val Asn Pro Pro Arg Arg Asp Val Val Asn Ile Gly Ala Ala Gly Asp
            420                 425                 430

Asn Val Thr Ile Arg Phe Thr Thr Asp Asn Pro Gly Pro Trp Phe Leu
        435                 440                 445

His Cys His Ile Asp Phe His Leu Glu Ala Gly Phe Ala Val Val Phe
    450                 455                 460

Ala Glu Asp Phe Asn Ala Thr Ala Ser Ser Asn Thr Val Thr Thr Glu
```

```
                465                 470                 475                 480
            Trp Ser Asn Leu Cys Thr Thr Tyr Asp Ala Leu Ser Ala Asp Asp Gln
                            485                 490                 495

<210> SEQ ID NO 3
<211> LENGTH: 495
<212> TYPE: PRT
<213> ORGANISM: Cerrena sp

<400> SEQUENCE: 3

Ala Ile Gly Pro Val Ala Asp Leu His Ile Thr Asp Ala Asn Val Ser
1               5                   10                  15

Pro Asp Gly Phe Thr Arg Pro Ala Val Leu Ala Gly Gly Thr Phe Pro
            20                  25                  30

Gly Pro Leu Ile Thr Gly Lys Gln Gly Asp Asn Phe Gln Ile Asn Val
        35                  40                  45

Ile Asp Glu Leu Thr Asp Ala Thr Met Leu Lys Ser Thr Ser Ile His
50                  55                  60

Trp His Gly Ile Phe Gln Lys Gly Thr Asn Trp Ala Asp Gly Pro Ser
65                  70                  75                  80

Phe Val Asn Gln Cys Pro Ile Thr Thr Gly Asn Ser Phe Leu Tyr Asp
                85                  90                  95

Phe Ser Val Pro Asp Gln Thr Gly Thr Tyr Trp Tyr His Ser His Leu
            100                 105                 110

Ser Thr Gln Tyr Cys Asp Gly Leu Arg Gly Ala Leu Val Ile Tyr Asp
        115                 120                 125

Asp Asn Asp Pro His Lys Asp Leu Tyr Asp Val Asp Asp Glu Thr Thr
130                 135                 140

Val Ile Thr Leu Ala Asp Trp Tyr His Thr Gln Ala Arg Leu Ile Thr
145                 150                 155                 160

Gly Val Pro Val Ser Asp Ala Thr Leu Ile Asn Gly Leu Gly Arg Tyr
                165                 170                 175

Leu Asn Gly Pro Thr Asp Ala Pro Leu Ala Val Ile Thr Val Asp Gln
            180                 185                 190

Gly Lys Arg Tyr Arg Phe Arg Leu Val Ser Ile Ser Cys Asp Pro Asn
        195                 200                 205

Phe Val Phe Ser Ile Asp Asn His Ser Met Thr Val Ile Glu Val Asp
210                 215                 220

Ala Val Asn Ser Gln Pro Leu Val Val Asp Ser Ile Gln Ile Phe Ala
225                 230                 235                 240

Ala Gln Arg Tyr Ser Phe Ile Leu Asn Ala Asn Gln Ser Val Gly Asn
                245                 250                 255

Tyr Trp Ile Arg Ala Asn Pro Asn Leu Gly Asn Thr Gly Phe Thr Asn
            260                 265                 270

Gly Ile Asn Ser Ala Ile Leu Arg Tyr Asn Gly Ala Pro Val Ala Glu
        275                 280                 285

Pro Asn Thr Thr Gln Thr Ala Ser Thr Asn Pro Leu Asn Glu Val Asn
290                 295                 300

Leu His Pro Leu Val Pro Thr Pro Val Pro Gly Thr Pro Gln Pro Gly
305                 310                 315                 320

Gly Val Asp Val Val Gln Asn Leu Val Leu Gly Phe Ser Gly Gly Lys
                325                 330                 335

Phe Thr Ile Asn Gly Val Ala Phe Ser Pro Pro Thr Val Pro Val Leu
            340                 345                 350

Leu Gln Ile Leu Ser Gly Thr Thr Thr Ala Gln Asp Leu Leu Pro Thr
```

```
                355                 360                 365
Gly Ser Ile Ile Glu Leu Pro Leu Gly Lys Thr Val Glu Leu Thr Leu
370                 375                 380

Ala Ala Gly Val Leu Gly Gly Pro His Pro Phe His Leu His Gly His
385                 390                 395                 400

Thr Phe His Val Val Arg Ser Ala Gly Gln Thr Thr Pro Asn Tyr Val
                405                 410                 415

Asp Pro Ile Leu Arg Asp Thr Val Asn Thr Gly Ala Ala Gly Asp Asn
                420                 425                 430

Val Thr Ile Arg Phe Thr Thr Asp Asn Pro Gly Pro Trp Phe Leu His
                435                 440                 445

Cys His Ile Asp Trp His Leu Glu Ala Gly Phe Ala Val Val Phe Ala
                450                 455                 460

Glu Gly Leu Asn Gln Thr Asn Ala Ala Asn Pro Thr Pro Asp Ala Trp
465                 470                 475                 480

Asn Asn Leu Cys Asp Leu Tyr Asn Ala Leu Pro Ala Gly Asp Gln
                485                 490                 495

<210> SEQ ID NO 4
<211> LENGTH: 500
<212> TYPE: PRT
<213> ORGANISM: Lentinus sp

<400> SEQUENCE: 4

Gly Ile Gly Pro Ile Ala Ser Leu Val Val Thr Asp Ala Gln Ile Ser
1               5                   10                  15

Pro Asp Gly Tyr Leu Arg Asp Ala Ile Val Thr Asn Gly Val Phe Pro
                20                  25                  30

Ala Pro Leu Ile Thr Gly Arg Lys Gly Asp His Phe Gln Leu Asn Val
                35                  40                  45

Val Asp Ser Met Thr Asn His Thr Met Leu Lys Ser Thr Ser Ile His
50                  55                  60

Trp His Gly Phe Phe Gln Lys Gly Thr Asn Trp Ala Asp Gly Pro Ala
65                  70                  75                  80

Phe Val Asn Gln Cys Pro Ile Ser Ser Gly His Ser Phe Leu Tyr Asp
                85                  90                  95

Phe His Val Pro Asp Gln Ala Gly Thr Phe Trp Tyr His Ser His Leu
                100                 105                 110

Ser Thr Gln Tyr Cys Asp Gly Leu Arg Gly Pro Met Val Val Tyr Asp
                115                 120                 125

Pro Asn Asp Pro His Ala Asn Leu Tyr Asp Ile Asp Asn Asp Ser Thr
                130                 135                 140

Val Ile Thr Leu Ala Asp Trp Tyr His Val Ala Ala Lys Leu Gly Pro
145                 150                 155                 160

Arg Phe Pro Leu Gly Ala Asp Ala Thr Leu Ile Asn Gly Lys Gly Arg
                165                 170                 175

Ser Pro Ala Thr Pro Thr Ala Ala Leu Ser Val Ile Asn Val Val Lys
                180                 185                 190

Gly Lys Arg Tyr Arg Phe Arg Leu Val Ser Ile Ser Cys Asp Pro Asn
                195                 200                 205

Tyr Val Phe Ser Ile Asp Asn His Thr Met Thr Val Ile Glu Ala Asp
                210                 215                 220

Thr Val Asn Thr Gln Pro Leu Ala Val Asp Ser Ile Gln Ile Phe Ala
225                 230                 235                 240

Ala Gln Arg Tyr Ser Phe Ile Leu Asn Ala Asn Gln Pro Val Asp Asn
```

```
            245                 250                 255
Tyr Trp Ile Arg Ala Asn Pro Asn Phe Gly Asn Val Gly Phe Thr Asp
            260                 265                 270
Gly Ile Asn Ser Ala Ile Leu Arg Tyr Thr Gly Ala Ala Leu Val Glu
            275                 280                 285
Pro Ser Ala Thr Thr Ala Pro Thr Leu Ser Asn Pro Leu Val Glu Thr
290                 295                 300
Asn Leu His Pro Leu Ala Pro Met Pro Val Pro Gly Gln Pro Val Ser
305                 310                 315                 320
Gly Gly Val Asp Lys Ala Ile Asn Phe Ala Phe Asn Phe Asp Gly Thr
                325                 330                 335
Asp Phe Phe Ile Asn Gly Ala Ser Phe Val Pro Pro Thr Val Pro Val
                340                 345                 350
Leu Leu Gln Ile Met Ser Gly Ala Ser Thr Ala Gln Asp Leu Leu Pro
                355                 360                 365
Ser Gly Ser Val Tyr Pro Leu Pro Ser Asn Ala Thr Ile Glu Leu Ser
            370                 375                 380
Phe Pro Ala Thr Ala Ala Ala Pro Gly Ala Pro His Pro Phe His Leu
385                 390                 395                 400
His Gly His Val Phe Ala Val Val Arg Ser Ala Gly Ser Thr Thr Tyr
                405                 410                 415
Asn Tyr Asn Asn Pro Ile Trp Arg Asp Val Val Ser Thr Gly Thr Pro
                420                 425                 430
Ala Ala Gly Asp Asn Val Thr Ile Arg Phe Ser Thr Asn Asn Pro Gly
                435                 440                 445
Pro Trp Phe Leu His Cys His Ile Asp Phe His Leu Glu Ala Gly Phe
            450                 455                 460
Ala Val Val Met Ala Glu Asp Val Pro Asp Ile Pro Ser Ala Asn Pro
465                 470                 475                 480
Val Pro Gln Ala Trp Ser Asn Leu Cys Pro Thr Tyr Asn Ala Leu Ser
                485                 490                 495
Ser Asp Asp Gln
            500

<210> SEQ ID NO 5
<211> LENGTH: 467
<212> TYPE: PRT
<213> ORGANISM: Lentinus sp

<400> SEQUENCE: 5

Gly Ile Gly Pro Ile Ala Ser Leu Val Val Thr Asp Ala Gln Ile Ser
1               5                   10                  15
Pro Asp Gly Tyr Leu Arg Asp Ala Ile Val Thr Asn Gly Val Phe Pro
                20                  25                  30
Ala Pro Leu Ile Thr Gly Arg Lys Gly Asp His Phe Gln Leu Asn Val
            35                  40                  45
Val Asp Ser Met Thr Asn His Thr Met Leu Lys Ser Thr Ser Ile His
    50                  55                  60
Trp His Gly Phe Phe Gln Lys Gly Thr Asn Trp Ala Asp Gly Pro Ala
65                  70                  75                  80
Phe Val Asn Gln Cys Pro Ile Ser Ser Gly His Ser Phe Leu Tyr Asp
                85                  90                  95
Phe His Val Pro Asp Gln Ala Gly Thr Phe Trp Tyr His Ser His Leu
                100                 105                 110
Ser Thr Gln Tyr Cys Asp Gly Leu Arg Gly Pro Met Val Val Tyr Asp
```

```
                    115                 120                 125
Pro Asn Asp Pro His Ala Asn Leu Tyr Asp Ile Asp Asn Asp Ser Thr
    130                 135                 140

Val Ile Thr Leu Ala Asp Trp Tyr His Val Ala Ala Lys Leu Gly Pro
145                 150                 155                 160

Arg Phe Pro Leu Gly Ala Asp Ala Thr Leu Ile Asn Gly Lys Gly Arg
                165                 170                 175

Ser Pro Ala Thr Pro Thr Ala Ala Leu Ser Val Ile Asn Val Val Lys
            180                 185                 190

Gly Lys Arg Tyr Arg Phe Arg Leu Val Ser Ile Ser Cys Asp Pro Asn
        195                 200                 205

Tyr Val Phe Ser Ile Asp Asn His Thr Met Thr Val Ile Glu Ala Asp
    210                 215                 220

Thr Val Asn Thr Gln Pro Leu Ala Val Asp Ser Ile Gln Ile Phe Ala
225                 230                 235                 240

Ala Gln Arg Tyr Ser Phe Ile Leu Asn Ala Asn Gln Pro Val Asp Asn
                245                 250                 255

Tyr Trp Ile Arg Ala Asn Pro Asn Phe Gly Asn Val Gly Phe Thr Asp
            260                 265                 270

Gly Ile Asn Ser Ala Ile Leu Arg Tyr Thr Gly Ala Ala Leu Val Glu
        275                 280                 285

Pro Ser Ala Thr Thr Ala Pro Thr Leu Ser Asn Pro Leu Val Glu Thr
    290                 295                 300

Asn Leu His Pro Leu Ala Pro Met Pro Val Pro Gly Gln Pro Val Ser
305                 310                 315                 320

Gly Gly Val Asp Lys Ala Ile Asn Phe Ala Phe Asn Phe Asp Gly Thr
                325                 330                 335

Asp Phe Phe Ile Asn Gly Ala Ser Phe Val Pro Pro Thr Val Pro Val
            340                 345                 350

Leu Leu Gln Ile Met Ser Gly Ala Ser Thr Ala Gln Asp Leu Leu Pro
        355                 360                 365

Ser Gly Ser Val Tyr Pro Leu Pro Ser Asn Ala Thr Ile Glu Leu Ser
    370                 375                 380

Phe Pro Ala Thr Ala Ala Ala Pro Gly Ala Pro His Pro Phe His Leu
385                 390                 395                 400

His Gly His Val Phe Ala Val Val Arg Ser Ala Gly Ser Thr Thr Tyr
                405                 410                 415

Asn Tyr Asn Asn Pro Ile Trp Arg Asp Val Val Ser Thr Gly Thr Pro
            420                 425                 430

Ala Ala Gly Asp Asn Val Thr Ile Arg Phe Ser Thr Asn Asn Pro Gly
        435                 440                 445

Pro Trp Phe Leu His Cys His Ile Asp Phe His Leu Glu Ala Gly Phe
    450                 455                 460

Ala Val Val
465

<210> SEQ ID NO 6
<211> LENGTH: 500
<212> TYPE: PRT
<213> ORGANISM: Lentinus sp

<400> SEQUENCE: 6

Ala Ile Gly Pro Val Ala Asp Leu Thr Ile Ser Asn Ala Gln Val Ser
1               5                   10                  15

Pro Asp Gly Phe Leu Arg Asp Ala Val Val Thr Asn Gly Leu Val Pro
```

```
                20                  25                  30
Gly Pro Leu Ile Thr Gly Asn Lys Gly Asp Arg Phe Gln Leu Asn Val
            35                  40                  45
Ile Asp Gln Met Thr Asn His Thr Met Leu Lys Thr Thr Ser Ile His
50                  55                  60
Trp His Gly Phe Phe Gln Lys Gly Thr Asn Trp Ala Asp Gly Pro Ala
65                  70                  75                  80
Phe Val Asn Gln Cys Pro Ile Ala Ser Gly Asn Ser Phe Leu Tyr Asp
                85                  90                  95
Phe Gln Val Pro Asp Gln Ala Gly Thr Phe Trp Tyr His Ser His Leu
            100                 105                 110
Ser Thr Gln Tyr Cys Asp Gly Leu Arg Gly Pro Leu Val Val Tyr Asp
        115                 120                 125
Pro Asn Asp Pro His Ala Ala Leu Tyr Asp Ile Asp Asp Asn Thr
    130                 135                 140
Val Ile Thr Leu Thr Asp Trp Tyr His Thr Ala Ala Arg Leu Gly Pro
145                 150                 155                 160
Arg Phe Pro Leu Gly Ala Asp Ala Thr Leu Ile Asn Gly Leu Gly Arg
                165                 170                 175
Ser Pro Ala Thr Pro Thr Ala Asn Leu Thr Val Ile Asn Val Thr Gln
            180                 185                 190
Gly Lys Arg Tyr Arg Phe Arg Leu Val Ser Ile Ser Cys Asp Pro Asn
        195                 200                 205
Tyr Val Phe Ser Ile Asp Asn His Thr Met Ser Val Ile Glu Thr Asp
    210                 215                 220
Thr Val Asn Thr Gln Pro Leu Thr Val Asp Ser Ile Gln Ile Tyr Ala
225                 230                 235                 240
Ala Gln Arg Tyr Ser Phe Val Leu Thr Ala Asn Gln Ser Val Asp Asn
                245                 250                 255
Tyr Trp Ile Arg Ala Asn Pro Asn Phe Gly Asn Val Gly Phe Thr Asp
            260                 265                 270
Ala Ile Asn Ser Ala Ile Leu Arg Tyr Asp Gly Ala Pro Asp Ala Glu
        275                 280                 285
Pro Ser Ala Thr Thr Ala Pro Thr Leu Thr Asn Pro Leu Val Glu Ala
    290                 295                 300
Asn Leu His Pro Leu Ala Ser Met Pro Val Pro Gly Ser Pro Val Ser
305                 310                 315                 320
Gly Gly Val Asp Lys Ala Ile Asn Phe Val Phe Asn Phe Asn Gly Thr
                325                 330                 335
Asn Phe Ser Ile Asn Asn Ala Thr Phe Val Pro Pro Thr Val Pro Val
            340                 345                 350
Leu Leu Gln Ile Met Ser Gly Ala Asn Thr Ala Gln Asp Leu Leu Pro
        355                 360                 365
Ser Gly Ser Val Tyr Thr Leu Pro Ser Asn Ala Thr Ile Glu Leu Ser
    370                 375                 380
Phe Pro Ala Thr Ser Asn Ala Pro Gly Ala Pro His Pro Phe His Leu
385                 390                 395                 400
His Gly His Val Phe Ala Val Val Arg Ser Ala Gly Ser Thr Val Tyr
                405                 410                 415
Asn Tyr Asp Asn Pro Ile Trp Arg Asp Val Val Ser Thr Gly Thr Pro
            420                 425                 430
Ala Ala Gly Asp Asn Val Thr Ile Arg Phe Gln Thr Asn Asn Pro Gly
        435                 440                 445
```

```
Pro Trp Phe Leu His Cys His Ile Asp Phe His Leu Asp Ala Gly Phe
    450             455                 460
Ala Val Val Met Ala Glu Asp Pro Val Asp Thr Pro Thr Ala Asp Pro
465             470                 475                 480
Val Pro Gln Ala Trp Ser Asp Leu Cys Pro Thr Tyr Asp Ala Leu Ser
                485                 490                 495
Val Asp Asp Gln
            500

<210> SEQ ID NO 7
<211> LENGTH: 518
<212> TYPE: PRT
<213> ORGANISM: Cerrena sp

<400> SEQUENCE: 7

Met Leu Asn Phe Asn Ser Leu Ser Thr Phe Ala Val Leu Ala Leu Ser
1               5                   10                  15
Met Arg Ala Asn Ala Ala Ile Gly Pro Val Thr Asp Leu Glu Ile Thr
            20                  25                  30
Asn Gly Thr Ile Ser Pro Asp Gly Tyr Ser Arg Ala Ala Val Leu Ala
        35                  40                  45
Gly Gly Ser Phe Pro Gly Pro Leu Ile Thr Gly Asn Lys Ser Asp Asn
    50                  55                  60
Phe Gln Ile Asn Val Val Asn Ser Leu Ala Asp Ser Asp Met Leu Lys
65                  70                  75                  80
Ser Thr Thr Val His Trp His Gly Phe Phe Gln Lys Gly Thr Asn Trp
                85                  90                  95
Ala Asp Gly Pro Ala Phe Val Asn Gln Cys Pro Ile Ala Thr Gly Asn
            100                 105                 110
Ser Phe Leu Tyr Asn Phe Asn Ala Thr Asp Gln Ala Gly Thr Phe Trp
        115                 120                 125
Tyr His Ser His Leu Gly Thr Gln Tyr Cys Asp Gly Leu Arg Gly Pro
    130                 135                 140
Met Val Val Tyr Asp Pro Asp Pro His Ala Asp Leu Tyr Asp Val
145                 150                 155                 160
Asp Asp Asp Ser Thr Val Ile Thr Leu Ala Asp Trp Tyr His Thr Leu
                165                 170                 175
Ala Arg Leu Gly Ala Ala Phe Pro Thr Ser Asp Ala Thr Leu Ile Asn
            180                 185                 190
Gly Leu Gly Arg Tyr Ser Asp Gly Asn Thr Thr Asp Leu Ala Val Ile
        195                 200                 205
Thr Val Glu Ser Gly Lys Arg Tyr Arg Phe Arg Leu Val Ser Ile Ser
    210                 215                 220
Cys Asp Pro Asn Phe Thr Phe Ser Ile Asp Asn His Thr Met Thr Ile
225                 230                 235                 240
Ile Glu Ala Asp Ala Val Asn Tyr Thr Pro Leu Asp Val Asp Glu Ile
                245                 250                 255
Gln Ile Phe Ala Gly Gln Arg Tyr Ser Phe Ile Leu Thr Ala Asn Gln
            260                 265                 270
Thr Val Asp Asn Tyr Trp Ile Arg Ala Asp Pro Asn Val Gly Thr Thr
        275                 280                 285
Gly Phe Asp Asn Gly Ile Asn Ser Ala Ile Leu Arg Tyr Ser Gly Ala
    290                 295                 300
Asp Glu Val Glu Pro Thr Thr Asn Gln Thr Thr Ser Thr Asn Pro Leu
305                 310                 315                 320
```

-continued

```
Val Glu Ala Asn Leu Val Pro Leu Asp Gly Ala Ala Pro Gly Glu
            325                 330                 335

Ala Val Ala Gly Gly Val Asp Tyr Ala Leu Asn Leu Ala Leu Ala Phe
            340                 345                 350

Asp Gly Thr Asn Leu Asp Phe Thr Val Asn Gly Tyr Glu Tyr Thr Ser
            355                 360                 365

Pro Thr Val Pro Val Leu Leu Gln Ile Leu Ser Gly Ala Ser Ser Val
            370                 375                 380

Asp Asp Leu Leu Pro Ser Gly Ser Ile Tyr Ser Leu Pro Ser Asn Ser
385                 390                 395                 400

Thr Ile Glu Leu Ser Ile Pro Ala Leu Ala Val Gly Ala Pro His Pro
            405                 410                 415

Ile His Leu His Gly His Thr Phe Ser Val Val Arg Ser Ala Gly Ser
            420                 425                 430

Thr Thr Tyr Asn Tyr Asp Asn Pro Pro Arg Arg Asp Val Val Ser Ile
            435                 440                 445

Gly Thr Ala Thr Asp Asp Asn Val Thr Ile Arg Phe Thr Thr Asp Asn
            450                 455                 460

Pro Gly Pro Trp Phe Leu His Cys His Ile Asp Phe His Leu Glu Ala
465                 470                 475                 480

Gly Phe Ala Val Val Phe Ala Glu Asp Phe Asn Asp Thr Ala Ser Ala
            485                 490                 495

Asn Thr Val Thr Thr Glu Trp Ser Asp Leu Cys Thr Thr Tyr Asp Ala
            500                 505                 510

Leu Ser Ser Asp Asp Leu
            515

<210> SEQ ID NO 8
<211> LENGTH: 517
<212> TYPE: PRT
<213> ORGANISM: Cerrena sp

<400> SEQUENCE: 8

Met Ile Asn Phe Asn Ser Leu Leu Thr Phe Thr Val Leu Ala Leu Ser
1               5                   10                  15

Met Arg Ala His Ala Ala Ile Gly Pro Val Thr Asp Leu Thr Ile Thr
            20                  25                  30

Asn Ala Thr Ile Ser Pro Asp Gly Phe Ser Arg Gln Ala Val Leu Ala
            35                  40                  45

Gly Gly Val Phe Pro Gly Pro Leu Ile Thr Gly Asn Lys Gly Asp Asn
        50                  55                  60

Phe Gln Ile Asn Val Val Asn Ser Leu Glu Asn Ser Asp Met Leu Lys
65                  70                  75                  80

Ser Thr Thr Ile His Trp His Gly Phe Phe Gln Lys Gly Thr Asn Trp
            85                  90                  95

Ala Asp Gly Pro Ala Phe Val Asn Gln Cys Pro Ile Ala Thr Gly Asn
            100                 105                 110

Ser Phe Leu Tyr Asn Phe Asn Ala Asp Asp Gln Ala Gly Thr Phe Trp
        115                 120                 125

Tyr His Ser His Leu Ser Thr Gln Tyr Cys Asp Gly Leu Arg Gly Pro
    130                 135                 140

Met Val Val Tyr Asp Pro Asn Asp Pro His Ala Ser Leu Tyr Asp Val
145                 150                 155                 160

Asp Asp Glu Ser Thr Val Ile Thr Leu Ala Asp Trp Tyr His Thr Leu
            165                 170                 175
```

```
Ala Arg Leu Gly Ala Ala Phe Pro Thr Ala Asp Ala Thr Leu Ile Asn
            180                 185                 190

Gly Leu Gly Arg Tyr Ser Asp Gly Thr Thr Ser Asp Leu Ala Val Ile
        195                 200                 205

Thr Val Glu Ser Gly Lys Arg Tyr Arg Phe Arg Leu Val Asn Ile Ser
210                 215                 220

Cys Asp Pro Asn Tyr Thr Phe Ser Ile Asp Asn His Thr Phe Thr Val
225                 230                 235                 240

Ile Glu Val Asp Gly Val Asn His Ala Ala Leu Asp Val Asp Glu Ile
                245                 250                 255

Gln Ile Phe Ala Gly Arg Tyr Ser Phe Val Leu Thr Ala Asn Gln
            260                 265                 270

Thr Val Asp Asn Tyr Trp Ile Arg Ala Asn Pro Asn Leu Gly Thr Thr
    275                 280                 285

Gly Phe Asp Asn Gly Ile Asn Ser Ala Ile Leu Arg Tyr Ser Gly Ala
        290                 295                 300

Asn Glu Thr Glu Pro Thr Thr Thr Gln Thr Thr Ala Thr Ala Ala Leu
305                 310                 315                 320

Ser Glu Ala Ser Leu Val Pro Leu Glu Asp Pro Ala Ala Pro Gly Glu
                325                 330                 335

Ala Val Ala Gly Gly Val Asp Tyr Ala Leu Asn Leu Ala Phe Ala Phe
            340                 345                 350

Asp Gly Ala Asn Leu Asp Phe Thr Val Asn Gly Glu Thr Tyr Val Ser
    355                 360                 365

Pro Thr Val Pro Val Leu Leu Gln Ile Leu Ser Gly Ala Ser Ser Val
        370                 375                 380

Ser Asp Leu Leu Pro Ala Gly Ser Val Tyr Ser Leu Pro Ser Asn Ser
385                 390                 395                 400

Thr Ile Glu Leu Ser Met Pro Gly Val Val Gly Gly His Pro
                405                 410                 415

Leu His Leu His Gly His Ala Phe Ser Val Val Arg Ser Ala Gly Ser
            420                 425                 430

Asp Thr Tyr Asn Tyr Val Asn Pro Pro Arg Arg Asp Val Val Asn Ile
    435                 440                 445

Gly Ala Ala Gly Asp Asn Val Thr Ile Arg Phe Thr Thr Asp Asn Pro
450                 455                 460

Gly Pro Trp Phe Leu His Cys His Ile Asp Phe His Leu Glu Ala Gly
465                 470                 475                 480

Phe Ala Val Val Phe Ala Glu Asp Phe Asn Ala Thr Ala Ser Ser Asn
                485                 490                 495

Thr Val Thr Thr Glu Trp Ser Asn Leu Cys Thr Thr Tyr Asp Ala Leu
            500                 505                 510

Ser Ala Asp Asp Gln
            515

<210> SEQ ID NO 9
<211> LENGTH: 516
<212> TYPE: PRT
<213> ORGANISM: Cerrena sp

<400> SEQUENCE: 9

Met Ala Phe Arg Thr Gly Phe Ser Ala Phe Ile Ser Leu Ser Leu Ala
1               5                   10                  15

Leu Gly Ala Leu Ala Ala Ile Gly Pro Val Ala Asp Leu His Ile Thr
            20                  25                  30
```

```
Asp Ala Asn Val Ser Pro Asp Gly Phe Thr Arg Pro Ala Val Leu Ala
        35                  40                  45
Gly Gly Thr Phe Pro Gly Pro Leu Ile Thr Gly Lys Gln Gly Asp Asn
 50                  55                  60
Phe Gln Ile Asn Val Ile Asp Glu Leu Thr Asp Ala Thr Met Leu Lys
 65                  70                  75                  80
Ser Thr Ser Ile His Trp His Gly Ile Phe Gln Lys Gly Thr Asn Trp
                 85                  90                  95
Ala Asp Gly Pro Ser Phe Val Asn Gln Cys Pro Ile Thr Thr Gly Asn
                100                 105                 110
Ser Phe Leu Tyr Asp Phe Ser Val Pro Asp Gln Thr Gly Thr Tyr Trp
            115                 120                 125
Tyr His Ser His Leu Ser Thr Gln Tyr Cys Asp Gly Leu Arg Gly Ala
        130                 135                 140
Leu Val Ile Tyr Asp Asp Asn Asp Pro His Lys Asp Leu Tyr Asp Val
145                 150                 155                 160
Asp Asp Glu Thr Thr Val Ile Thr Leu Ala Asp Trp Tyr His Thr Gln
                165                 170                 175
Ala Arg Leu Ile Thr Gly Val Pro Val Ser Asp Ala Thr Leu Ile Asn
            180                 185                 190
Gly Leu Gly Arg Tyr Leu Asn Gly Pro Thr Asp Ala Pro Leu Ala Val
        195                 200                 205
Ile Thr Val Asp Gln Gly Lys Arg Tyr Arg Phe Arg Leu Val Ser Ile
210                 215                 220
Ser Cys Asp Pro Asn Phe Val Phe Ser Ile Asp Asn His Ser Met Thr
225                 230                 235                 240
Val Ile Glu Val Asp Ala Val Asn Ser Gln Pro Leu Val Val Asp Ser
                245                 250                 255
Ile Gln Ile Phe Ala Ala Gln Arg Tyr Ser Phe Ile Leu Asn Ala Asn
            260                 265                 270
Gln Ser Val Gly Asn Tyr Trp Ile Arg Ala Asn Pro Asn Leu Gly Asn
        275                 280                 285
Thr Gly Phe Thr Asn Gly Ile Asn Ser Ala Ile Leu Arg Tyr Asn Gly
290                 295                 300
Ala Pro Val Ala Glu Pro Asn Thr Thr Gln Thr Ala Ser Thr Asn Pro
305                 310                 315                 320
Leu Asn Glu Val Asn Leu His Pro Leu Val Pro Thr Pro Val Pro Gly
                325                 330                 335
Thr Pro Gln Pro Gly Gly Val Asp Val Gln Asn Leu Val Leu Gly
            340                 345                 350
Phe Ser Gly Gly Lys Phe Thr Ile Asn Gly Val Ala Phe Ser Pro Pro
        355                 360                 365
Thr Val Pro Val Leu Leu Gln Ile Leu Ser Gly Thr Thr Thr Ala Gln
370                 375                 380
Asp Leu Leu Pro Thr Gly Ser Ile Ile Glu Leu Pro Leu Gly Lys Thr
385                 390                 395                 400
Val Glu Leu Thr Leu Ala Ala Gly Val Leu Gly Gly Pro His Pro Phe
                405                 410                 415
His Leu His Gly His Thr Phe His Val Val Arg Ser Ala Gly Gln Thr
            420                 425                 430
Thr Pro Asn Tyr Val Asp Pro Ile Leu Arg Asp Thr Val Asn Thr Gly
        435                 440                 445
Ala Ala Gly Asp Asn Val Thr Ile Arg Phe Thr Thr Asp Asn Pro Gly
450                 455                 460
```

```
Pro Trp Phe Leu His Cys His Ile Asp Trp His Leu Glu Ala Gly Phe
465                 470                 475                 480

Ala Val Val Phe Ala Glu Gly Leu Asn Gln Thr Asn Ala Ala Asn Pro
            485                 490                 495

Thr Pro Asp Ala Trp Asn Asn Leu Cys Asp Leu Tyr Asn Ala Leu Pro
500                 505                 510

Ala Gly Asp Gln
        515

<210> SEQ ID NO 10
<211> LENGTH: 521
<212> TYPE: PRT
<213> ORGANISM: Lentinus sp

<400> SEQUENCE: 10

Met Ala Lys Phe Gln Ser Leu Leu Ser Tyr Thr Leu Leu Ser Leu Val
1               5                   10                  15

Ala Thr Val Tyr Ala Gly Ile Gly Pro Ile Ala Ser Leu Val Val Thr
            20                  25                  30

Asp Ala Gln Ile Ser Pro Asp Gly Tyr Leu Arg Asp Ala Ile Val Thr
        35                  40                  45

Asn Gly Val Phe Pro Ala Pro Leu Ile Thr Gly Arg Lys Gly Asp His
50                  55                  60

Phe Gln Leu Asn Val Val Asp Ser Met Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Val Asn Gln Cys Pro Ile Ser Ser Gly His
            100                 105                 110

Ser Phe Leu Tyr Asp Phe His Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Met Val Val Tyr Asp Pro Asn Asp Pro His Ala Asn Leu Tyr Asp Ile
145                 150                 155                 160

Asp Asn Asp Ser Thr Val Ile Thr Leu Ala Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Lys Gly Arg Ser Pro Ala Thr Pro Thr Ala Ala Leu Ser Val
        195                 200                 205

Ile Asn Val Val Lys Gly Lys Arg Tyr Arg Phe Arg Leu Val Ser Ile
210                 215                 220

Ser Cys Asp Pro Asn Tyr Val Phe Ser Ile Asp Asn His Thr Met Thr
225                 230                 235                 240

Val Ile Glu Ala Asp Thr Val Asn Thr Gln Pro Leu Ala Val Asp Ser
                245                 250                 255

Ile Gln Ile Phe Ala Ala Gln Arg Tyr Ser Phe Ile Leu Asn Ala Asn
            260                 265                 270

Gln Pro Val Asp Asn Tyr Trp Ile Arg Ala Asn Pro Asn Phe Gly Asn
        275                 280                 285

Val Gly Phe Thr Asp Gly Ile Asn Ser Ala Ile Leu Arg Tyr Thr Gly
    290                 295                 300

Ala Ala Leu Val Glu Pro Ser Ala Thr Thr Ala Pro Thr Leu Ser Asn
305                 310                 315                 320
```

Pro Leu Val Glu Thr Asn Leu His Pro Leu Ala Pro Met Pro Val Pro
                325                 330                 335

Gly Gln Pro Val Ser Gly Val Asp Lys Ala Ile Asn Phe Ala Phe
            340                 345                 350

Asn Phe Asp Gly Thr Asp Phe Ile Asn Gly Ala Ser Phe Val Pro
            355                 360                 365

Pro Thr Val Pro Val Leu Leu Gln Ile Met Ser Gly Ala Ser Thr Ala
                370                 375                 380

Gln Asp Leu Leu Pro Ser Gly Ser Val Tyr Pro Leu Pro Ser Asn Ala
385                 390                 395                 400

Thr Ile Glu Leu Ser Phe Pro Ala Thr Ala Ala Pro Gly Ala Pro
                405                 410                 415

His Pro Phe His Leu His Gly His Val Phe Ala Val Val Arg Ser Ala
                420                 425                 430

Gly Ser Thr Thr Tyr Asn Tyr Asn Asn Pro Ile Trp Arg Asp Val Val
            435                 440                 445

Ser Thr Gly Thr Pro Ala Ala Gly Asp Asn Val Thr Ile Arg Phe Ser
450                 455                 460

Thr Asn Asn Pro Gly Pro Trp Phe Leu His Cys His Ile Asp Phe His
465                 470                 475                 480

Leu Glu Ala Gly Phe Ala Val Val Met Ala Glu Asp Val Pro Asp Ile
                485                 490                 495

Pro Ser Ala Asn Pro Val Pro Gln Ala Trp Ser Asn Leu Cys Pro Thr
            500                 505                 510

Tyr Asn Ala Leu Ser Ser Asp Asp Gln
            515                 520

<210> SEQ ID NO 11
<211> LENGTH: 488
<212> TYPE: PRT
<213> ORGANISM: Lentinus sp

<400> SEQUENCE: 11

Met Ala Lys Phe Gln Ser Leu Leu Ser Tyr Thr Leu Leu Ser Leu Val
1               5                   10                  15

Ala Thr Val Tyr Ala Gly Ile Gly Pro Ile Ala Ser Leu Val Val Thr
            20                  25                  30

Asp Ala Gln Ile Ser Pro Asp Gly Tyr Leu Arg Asp Ala Ile Val Thr
            35                  40                  45

Asn Gly Val Phe Pro Ala Pro Leu Ile Thr Gly Arg Lys Gly Asp His
    50                  55                  60

Phe Gln Leu Asn Val Val Asp Ser Met Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Val Asn Gln Cys Pro Ile Ser Ser Gly His
            100                 105                 110

Ser Phe Leu Tyr Asp Phe His Val Pro Asp Gln Ala Gly Thr Phe Trp
            115                 120                 125

Tyr His Ser His Leu Ser Thr Gln Tyr Cys Asp Gly Leu Arg Gly Pro
    130                 135                 140

Met Val Val Tyr Asp Pro Asn Asp Pro His Ala Asn Leu Tyr Asp Ile
145                 150                 155                 160

Asp Asn Asp Ser Thr Val Ile Thr Leu Ala Asp Trp Tyr His Val Ala
                165                 170                 175

```
Ala Lys Leu Gly Pro Arg Phe Pro Leu Gly Ala Asp Ala Thr Leu Ile
            180                 185                 190

Asn Gly Lys Gly Arg Ser Pro Ala Thr Pro Thr Ala Ala Leu Ser Val
            195                 200                 205

Ile Asn Val Val Lys Gly Lys Arg Tyr Arg Phe Arg Leu Val Ser Ile
210                 215                 220

Ser Cys Asp Pro Asn Tyr Val Phe Ser Ile Asp Asn His Thr Met Thr
225                 230                 235                 240

Val Ile Glu Ala Asp Thr Val Asn Thr Gln Pro Leu Ala Val Asp Ser
                245                 250                 255

Ile Gln Ile Phe Ala Ala Gln Arg Tyr Ser Phe Ile Leu Asn Ala Asn
                260                 265                 270

Gln Pro Val Asp Asn Tyr Trp Ile Arg Ala Asn Pro Asn Phe Gly Asn
                275                 280                 285

Val Gly Phe Thr Asp Gly Ile Asn Ser Ala Ile Leu Arg Tyr Thr Gly
            290                 295                 300

Ala Ala Leu Val Glu Pro Ser Ala Thr Thr Ala Pro Thr Leu Ser Asn
305                 310                 315                 320

Pro Leu Val Glu Thr Asn Leu His Pro Leu Ala Pro Met Pro Val Pro
                325                 330                 335

Gly Gln Pro Val Ser Gly Gly Val Asp Lys Ala Ile Asn Phe Ala Phe
                340                 345                 350

Asn Phe Asp Gly Thr Asp Phe Phe Ile Asn Gly Ala Ser Phe Val Pro
                355                 360                 365

Pro Thr Val Pro Val Leu Leu Gln Ile Met Ser Gly Ala Ser Thr Ala
370                 375                 380

Gln Asp Leu Leu Pro Ser Gly Ser Val Tyr Pro Leu Pro Ser Asn Ala
385                 390                 395                 400

Thr Ile Glu Leu Ser Phe Pro Ala Thr Ala Ala Pro Gly Ala Pro
            405                 410                 415

His Pro Phe His Leu His Gly His Val Phe Ala Val Val Arg Ser Ala
                420                 425                 430

Gly Ser Thr Thr Tyr Asn Tyr Asn Asn Pro Ile Trp Arg Asp Val Val
            435                 440                 445

Ser Thr Gly Thr Pro Ala Ala Gly Asp Asn Val Thr Ile Arg Phe Ser
            450                 455                 460

Thr Asn Asn Pro Gly Pro Trp Phe Leu His Cys His Ile Asp Phe His
465                 470                 475                 480

Leu Glu Ala Gly Phe Ala Val Val
                485

<210> SEQ ID NO 12
<211> LENGTH: 521
<212> TYPE: PRT
<213> ORGANISM: Lentinus sp

<400> SEQUENCE: 12

Met Ala Lys Phe Gln Ser Leu Leu Ser Tyr Thr Val Leu Ser Phe Val
1               5                   10                  15

Ala Ala Ala Tyr Ala Ala Ile Gly Pro Val Ala Asp Leu Thr Ile Ser
            20                  25                  30

Asn Ala Gln Val Ser Pro Asp Gly Phe Leu Arg Asp Ala Val Val Thr
            35                  40                  45

Asn Gly Leu Val Pro Gly Pro Leu Ile Thr Gly Asn Lys Gly Asp Arg
50                  55                  60
```

```
Phe Gln Leu Asn Val Ile Asp Gln Met Thr Asn His Thr Met Leu Lys
 65                  70                  75                  80

Thr Thr Ser Ile His Trp His Gly Phe Phe Gln Lys Gly Thr Asn Trp
                 85                  90                  95

Ala Asp Gly Pro Ala Phe Val Asn Gln Cys Pro Ile Ala Ser Gly Asn
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Leu Val Val Tyr Asp Pro Asn Asp Pro His Ala Ala Leu Tyr Asp Ile
145                 150                 155                 160

Asp Asp Asp Asn Thr Val Ile Thr Leu Thr Asp Trp Tyr His Thr Ala
                165                 170                 175

Ala Arg Leu Gly Pro Arg Phe Pro Leu Gly Ala Asp Ala Thr Leu Ile
            180                 185                 190

Asn Gly Leu Gly Arg Ser Pro Ala Thr Pro Thr Ala Asn Leu Thr Val
        195                 200                 205

Ile Asn Val Thr Gln Gly Lys Arg Tyr Arg Phe Arg Leu Val Ser Ile
    210                 215                 220

Ser Cys Asp Pro Asn Tyr Val Phe Ser Ile Asp Asn His Thr Met Ser
225                 230                 235                 240

Val Ile Glu Thr Asp Thr Val Asn Thr Gln Pro Leu Thr Val Asp Ser
                245                 250                 255

Ile Gln Ile Tyr Ala Ala Gln Arg Tyr Ser Phe Val Leu Thr Ala Asn
            260                 265                 270

Gln Ser Val Asp Asn Tyr Trp Ile Arg Ala Asn Pro Asn Phe Gly Asn
        275                 280                 285

Val Gly Phe Thr Asp Ala Ile Asn Ser Ala Ile Leu Arg Tyr Asp Gly
    290                 295                 300

Ala Pro Asp Ala Glu Pro Ser Ala Thr Thr Ala Pro Thr Leu Thr Asn
305                 310                 315                 320

Pro Leu Val Glu Ala Asn Leu His Pro Leu Ala Ser Met Pro Val Pro
                325                 330                 335

Gly Ser Pro Val Ser Gly Val Asp Lys Ala Ile Asn Phe Val Phe
            340                 345                 350

Asn Phe Asn Gly Thr Asn Phe Ser Ile Asn Asn Ala Thr Phe Val Pro
        355                 360                 365

Pro Thr Val Pro Val Leu Leu Gln Ile Met Ser Gly Ala Asn Thr Ala
    370                 375                 380

Gln Asp Leu Leu Pro Ser Gly Ser Val Tyr Thr Leu Pro Ser Asn Ala
385                 390                 395                 400

Thr Ile Glu Leu Ser Phe Pro Ala Thr Ser Asn Ala Pro Gly Ala Pro
                405                 410                 415

His Pro Phe His Leu His Gly His Val Phe Ala Val Val Arg Ser Ala
            420                 425                 430

Gly Ser Thr Val Tyr Asn Tyr Asp Asn Pro Ile Trp Arg Asp Val Val
        435                 440                 445

Ser Thr Gly Thr Pro Ala Ala Gly Asp Asn Val Thr Ile Arg Phe Gln
    450                 455                 460

Thr Asn Asn Pro Gly Pro Trp Phe Leu His Cys His Ile Asp Phe His
465                 470                 475                 480

Leu Asp Ala Gly Phe Ala Val Val Met Ala Glu Asp Pro Val Asp Thr
```

|   |   |   |   |   | 485 |   |   |   | 490 |   |   |   | 495 |   |
|---|---|---|---|---|-----|---|---|---|-----|---|---|---|-----|---|
| Pro | Thr | Ala | Asp | Pro | Val | Pro | Gln | Ala | Trp | Ser | Asp | Leu | Cys | Pro | Thr |
|   |   |   |   | 500 |   |   |   |   | 505 |   |   |   |   | 510 |

Tyr Asp Ala Leu Ser Val Asp Asp Gln
    515            520

```
<210> SEQ ID NO 13
<211> LENGTH: 1494
<212> TYPE: DNA
<213> ORGANISM: Cerrena sp

<400> SEQUENCE: 13
gctatcggtc ctgtcactga cttagaaatc acgaacggca ccatctctcc cgatggctat      60
tctcgtgcag ccgtccttgc tggaggctct ttccccggcc cacttatcac aggaaacaaa     120
agtgacaact tccaaatcaa cgttgtgaac tcgttggccg attccgacat gcttaagtct     180
acaaccgttc actggcacgg tttcttccaa aagggtacca ctgggctga cggccctgct      240
ttcgtcaacc agtgtcccat gcgacgggc aactcttttcc tttacaactt caacgctacg     300
gaccaggctg gtactttctg gtaccattct cacttggaga ctcagtactg tgatggtctt     360
cgtggcccga tggttgtcta tgacccagac gatcctcatg ctgacctcta cgatgtcgac     420
gacgatagca ctgtcattac tcttgccgat tggtatcaca cccttgctcg acttggtgcc     480
gctttcccga cttcggacgc tactttgatc aacggtttgg gccgttacag cgatggtaac     540
acaaccgatc tcgctgtcat tactgtcgaa tccggcaaga ggtaccgatt caggctggtc     600
agcatttctt gcgatcccaa cttcactttc tccatcgaca ccacaccat gacaatcatc      660
gaggctgatg ctgtcaacta tacaccctc gatgttgacg agattcaaat cttcgctggt      720
caacgttact ccttcattct cactgccaac cagaccgtcg acaactactg gattcgtgct     780
gaccccaacg ttggtacgac tggcttcgac aatggcatca actccgctat ccttcgttac     840
agcggtgccg acgaggtcga gcctaccacc aaccagacca ccagtactaa ccctcttgtt     900
gaggctaact tggttcctct cgatggtgct gctgctcccg tgaagctgt cgctggaggt      960
gttgactatg cgctgaactt ggctctcgct ttcgacggta caaacctcga tttcaccgtc    1020
aacggttacg agtacacctc tcctaccgtc ccagtcctac tccaaattct cagcggtgcc    1080
tcttccgtcg acgacttgct ccccagtgga agcatttact cactgccaag caactccact    1140
atcgagctca gtattcccgc acttgccgtc ggtgctcccc accctatcca tttgcacggt    1200
cacactttct ctgtcgttcg tagtgccgga tccaccacct acaactacga caacccccct    1260
cgtcgtgacg tcgtcagcat tggtaccgcc actgatgata acgttaccat tcgtttcacc    1320
accgacaacc cgggaccttg gttcctccac tgtcacattg acttccactt ggaagctggt    1380
ttcgcagtcg tctttgctga agactttaat gacactgctt ctgctaacac tgtcaccact    1440
gaatggagcg acctctgcac tacctacgat gccctctcct ccgatgacct ctaa          1494

<210> SEQ ID NO 14
<211> LENGTH: 1491
<212> TYPE: DNA
<213> ORGANISM: Cerrena sp

<400> SEQUENCE: 14
gctatcggtc ccgtcactga cctcacaatc actaatgcca ccatttcccc ggatggtttc      60
tctcgtcaag ccgtgcttgc tggaggtgtt ttccctggtc cgcttattac cggaaacaag    120
ggcgacaact tccaaatcaa tgttgttaat tcattggaaa actctgacat gcttaagtct    180
```

```
acgaccattc actggcacgg tttcttccag aagggtacca actgggccga tggtcctgcc    240
ttcgttaacc aatgccccat cgccacgggc aactctttcc tgtacaactt caacgcagac    300
gaccaggctg gtacattctg gtaccactct cacttgtcta ctcaatattg cgatggtctc    360
cgaggcccta tggtcgtcta cgacccgaac gatcctcacg cttccctcta cgatgttgat    420
gatgagagca ctgtgattac cctcgccgat tggtaccaca cccttgcccg acttggtgca    480
gctttcccga ctgcgatgc taccctcatt aacggcttgg tcgttacag cgatggtact    540
acttcggacc ttgctgttat caccgttgag tccggaaaga ggtaccgatt ccgattggtc    600
aacatttctt gcgaccccaa ctacactttc tctatcgaca accacacatt caccgtcatt    660
gaggtcgatg gtgtcaacca cgcggcgctt gatgtcgatg aaatccagat cttcgctggt    720
caacgttact cctttgttct cactgctaac caaaccgtcg acaactactg gatccgtgca    780
aaccccaatc tcggaaccac cggcttcgac aacggcatca actccgctat cctccgttac    840
agcggtgcta acgagactga acccaccacc acccagacca ccgctactgc tgctctcagc    900
gaagctagcc tcgttcctct cgaggaccct gctgctcctg gtgaggccgt tgccggaggt    960
gtcgattatg ctttgaactt ggcattcgcc ttcgacggtg ccaaccttga cttcacagtc   1020
aacggtgaaa cctacgtctc ccctaccgtc cccgtcctcc tccaaattct tagcggtgct   1080
tcctccgtct ctgacttgct ccctgcccga agcgtctact ccttgcccag caactccacc   1140
atcgagctca gcatgcctgg aggtgtcgtc ggtggtggtc accccttca cttgcacggt   1200
cacgccttct ccgttgttcg tagtgccggc tctgacactt acaactacgt caacccccct   1260
cgccgtgatg ttgtcaacat tggtgctgct ggtgacaacg tcactatccg tttcaccact   1320
gacaaccccg accctggtt cctccactgc cacatcgatt tccacttgga agctggcttc   1380
gctgtcgtct ttgctgagga cttcaacgcc accgcttctt ctaacaccgt caccactgag   1440
tggagcaacc tttgcaccac ctacgacgcc ctctctgccg acgatcagta a            1491

<210> SEQ ID NO 15
<211> LENGTH: 1488
<212> TYPE: DNA
<213> ORGANISM: Cerrena sp

<400> SEQUENCE: 15
gctatcggtc ctgttgctga ccttcacatc acggatgcga acgtttctcc tgatggcttc     60
actcgacctg ctgtccttgc tggtggcacc ttccccggcc ctctcattac gggaaagcag    120
ggtgacaact tccagatcaa tgtcatcgac gaactcacgg acgcgactat gttgaagtct    180
acgtctattc attggcacgg tatcttccag aaaggcacca actgggctga cggcccctcc    240
ttcgtcaatc agtgccccat cactacagga aactcgttcc tgtacgactt ttctgtcccc    300
gaccagaccg gcacgtactg gtatcacagt catttatcca cccagtactg tgacggtttg    360
cgaggagccc ttgtcattta cgacgacaat gatcctcaca aggatctcta tgatgttgat    420
gatgagacta ccgtcatcac cctcgccgac tggtatcata cccaggctcg cctgatcact    480
ggtgtccctg tctccgatgc gactctgatc aacggtcttg gccgttatct taatggccca    540
accgatgctc cgctcgctgt tatcactgtc gaccaaggaa acgttatcg tttccgtctc    600
gtctctattt catgcgaccc gaacttcgtc ttctccattg acaaccattc catgactgtc    660
attgaagtcg atgctgtcaa cagccagcct ctcgtcgtcg actctattca aatcttcgcg    720
gcacagcgat actccttcat tttgaatgcc aaccaaagtg tcggaaacta ctggatccgt    780
gccaaccccca acttgggcaa cactggtttt acgaatggca ttaactcggc cattcttcgg    840
```

| | |
|---|---|
| tacaatggtg ctcctgttgc tgagcccaac accacccaaa ctgctagcac caacccttg | 900 |
| aacgaggtta accttcaccc tctagttccc acgcccgtcc ctggtactcc tcagcctggc | 960 |
| ggtgttgatg ttgtccagaa ccttgtcctc ggtttcagcg gcggcaagtt cactatcaac | 1020 |
| ggtgttgcct tttctccccc gacggtccca gttctccttc aaatccttag cggtactact | 1080 |
| actgcccaag atcttcttcc cactggatcc attatcgagc ttcccctcgg aaagactgtt | 1140 |
| gaacttaccc tggcagcggg cgttctcggt ggtcccacc ccttccactt gcacggtcac | 1200 |
| actttccacg ttgttcgcag cgctggtcag actactccta actacgtcga tcctattctt | 1260 |
| cgtgacactg tcaacaccgg tgctgctggc acaatgttta ctatccgttt caccactgac | 1320 |
| aaccctggac cctggttcct ccactgccac attgattggc acttggaagc cggtttcgct | 1380 |
| gttgtcttcg ctgaaggtct taaccagacc aatgctgcta accccactcc tgatgcttgg | 1440 |
| aacaaccttt gcgacctcta caatgccctt cctgctggtg accagtag | 1488 |

<210> SEQ ID NO 16
<211> LENGTH: 1503
<212> TYPE: DNA
<213> ORGANISM: Lentinus sp

<400> SEQUENCE: 16

| | |
|---|---|
| ggcatcggcc ccattgctag cctcgtcgtc accgatgccc agattagccc cgacggctac | 60 |
| ttgcgcgatg ctatcgtgac caatgggtc ttcccagccc ctctgatcac tggacgtaag | 120 |
| ggtgatcact tccagctgaa tgtcgtggat tccatgacaa accacaccat gctgaaatcc | 180 |
| acaagtatcc actggcatgg cttcttccag aagggcacaa actgggctga tggtcctgca | 240 |
| tttgtgaacc agtgccctat ttccagcggc cactcgttcc tctacgactt ccacgttccg | 300 |
| gaccaagcag ggacgttctg gtaccacagt cacttgtcca ctcaatactg cgacggtttg | 360 |
| aggggcccga tggttgtgta cgatcccaac gaccctcatg caaatctcta cgacatcgat | 420 |
| aacgacagca ctgtgataac tctcgccgat tggtatcacg tcgcgccaa gctcggccct | 480 |
| cgcttcccac ttggggctga tgctacccct atcaacggaa agggcagaag ccctgccact | 540 |
| cccacagcag cactgtccgt catcaacgtg gtcaaaggca agcggtatcg gttccgcttg | 600 |
| gtttcaatct cctgcgaccc gaactatgtg ttcagcatcg acaaccatac gatgacggtc | 660 |
| atcgaggccg ataccgtgaa cacccagccc ctcgccgtcg acagcatcca gatcttcgcg | 720 |
| gcccagcgtt actcattcat tctcaacgcc aaccagcccg tcgacaacta ctggattcgc | 780 |
| gccaacccga acttcgggaa cgtcggattt acggatggca tcaactctgc tatcctccgt | 840 |
| tacactgggg cggcactggt cgaaccgtct gcgaccaccg ctccgacact gagcaaccct | 900 |
| ctcgtcgaga caaacctgca tcctcttgcg cccatgcctg tgcccggaca cccgtttcc | 960 |
| ggtggtgtcg ataaggctat caacttcgcc ttcaacttcg atggcacgga cttcttcatc | 1020 |
| aacgcgcgca gcttcgtccc cctacggtt ccggtcctttc tccaaatcat gagcggcgcc | 1080 |
| agcacggcgc aggacctcct tccttccggc agcgtctacc cgcttccatc aaacgcgacg | 1140 |
| atcgagctct ccttcccggc gaccgccgct gcgcctggcg ccccccaccc cttccacttg | 1200 |
| cacggccacg tcttcgccgt cgtccgcagc gcgggaagca ccacctacaa ttacaacaac | 1260 |
| cccatctggc gcgatgtcgt cagcactggc accctgcag cgggcgacaa cgtcaccatc | 1320 |
| cgttttttcga cgaacaaccc gggtccgtgg ttcctccact gccacatcga cttccacctc | 1380 |
| gaggcgggct tcgcagtagt catggccgaa gacgtccccg acattccgtc tgcgaaccct | 1440 |
| gtgccccagg cgtggtcgaa cctttgccca acttacaacg cgctcagttc tgatgatcag | 1500 |

```
taa                                                                     1503

<210> SEQ ID NO 17
<211> LENGTH: 1404
<212> TYPE: DNA
<213> ORGANISM: Lentinus sp

<400> SEQUENCE: 17
ggcatcggcc ccattgctag cctcgtcgtc accgatgccc agattagccc cgacggctac      60
ttgcgcgatg ctatcgtgac caatggggtc ttcccagccc ctctgatcac tggacgtaag     120
ggtgatcact tccagctgaa tgtcgtggat tccatgacaa accacaccat gctgaaatcc     180
acaagtatcc actggcatgg cttcttccag aagggcacaa actgggctga tggtcctgca     240
tttgtgaacc agtgccctat ttccagcggc cactcgttcc tctacgactt ccacgttccg     300
gaccaagcag ggacgttctg gtaccacagt cacttgtcca ctcaatactg cgacggtttg     360
aggggcccga tggttgtgta cgatcccaac gaccctcatg caaatctcta cgacatcgat     420
aacgacagca ctgtgataac tctcgccgat tggtatcacg tcgcggccaa gctcggccct     480
cgcttcccac ttggggctga tgctaccctt atcaacggaa agggcagaag ccctgccact     540
cccacagcag cactgtccgt catcaacgtg gtcaaaggca agcggtatcg gttccgcttg     600
gtttcaatct cctgcgaccc gaactatgtg ttcagcatcg acaaccatac gatgacggtc     660
atcgaggccg ataccgtgaa cacccagccc ctcgccgtcg acagcatcca gatcttcgcg     720
gcccagcgtt actcattcat tctcaacgcc aaccagcccg tcgacaacta ctggattcgc     780
gccaacccga acttcgggaa cgtcggattt acggatggca tcaactctgc tatcctccgt     840
tacactgggg cggcactggt cgaaccgtct gcgaccaccg ctccgacact gagcaaccct     900
ctcgtcgaga caaacctgca tcctcttgcg cccatgcctg tgcccggaca accgtttcc      960 ggtggtgtcg ataaggctat caacttcgcc ttcaacttcg atggcacgga cttcttcatc    1020
aacggcgcga gcttcgtccc acctacggtt ccggtccttc tccaaatcat gagcggcgcc    1080
agcacggcgc aggacctcct tccttccggc agcgtctacc cgcttccatc aaacgcgacg    1140
atcgagctct ccttcccggc gaccgccgct gcgcctggcg ccccccaccc cttccacttg    1200
cacggccacg tcttcgccgt cgtccgcagc gcgggaagca ccacctacaa ttacaacaac    1260
cccatctggc gcgatgtcgt cagcactggc accccctgcag cgggcgacaa cgtcaccatc    1320 cgttttttcga cgaacaaccc gggtccgtgg ttcctccact gccacatcga cttccacctc    1380
gaggcgggct tcgcagtagt ctag                                           1404

<210> SEQ ID NO 18
<211> LENGTH: 1503
<212> TYPE: DNA
<213> ORGANISM: Lentinus sp

<400> SEQUENCE: 18
gccatcggcc cagtcgctga ccttaccatc agcaatgccc aagtcagccc cgacggcttc      60
ctccgcgatg ccgtcgtgac caacggcctg gtccctgggc ccctcatcac gggcaacaag     120
ggcgatcgct tccagttgaa tgtcattgat caaatgacca accacacgat gttgaagact     180
acgagcattc actggcacgg cttcttccag aagggcacca actgggctga tggacctgcg     240
tttgtgaacc agtgccccat tgccagcggc aactccttcc tctacgactt ccaggtccct     300
gaccaggctg gcaccttctg gtatcacagc caccttcgac cccagtactg cgacggtctc     360 cggggggcctc tcgttgtgta cgaccccaat gacccacacg ctgccctcta tgatatcgac     420
```

| | |
|---|---|
| gatgataaca ccgttattac tttgactgac tggtaccata ctgcggccag gctcggacct | 480 |
| cgtttcccgc tgggagcaga tgccactctc atcaacggcc tgggccgcag cccagccacg | 540 |
| ccgaccgcca acctaactgt catcaacgtt actcagggca agcgctaccg cttccgcctc | 600 |
| gtgtcgatct cttgcgaccc gaactatgtg ttcagcatcg acaaccacac gatgagcgtc | 660 |
| attgagacgg acactgtcaa cactcaaccg ctcacggtcg atagcattca gatctacgcc | 720 |
| gcccagcgct actcctttgt gctcaccgcc aaccagtccg tggataacta ctggatccgg | 780 |
| gcaaacccca acttcggtaa cgtcggcttc acggatgcta tcaactcggc catcctccgc | 840 |
| tatgacggtg ctcccgacgc tgagccctcc gctaccactg caccgacgtt gaccaacccg | 900 |
| ctggttgagg cgaaccttca cccgcttgct tcgatgcccg tgcccggatc ccctgtgtct | 960 |
| ggcggtgtgg acaaggccat taacttcgtc ttcaacttca acggcacgaa cttctccatc | 1020 |
| aacaacgcga ctttcgttcc gcccaccgtt ccggtgctgc tccagatcat gagcggcgcc | 1080 |
| aacaccgccc aagacctcct gccctctggc agcgtgtaca cactcccgtc caacgctacc | 1140 |
| attgagctgt ccttccctgc gacgagcaac gcccccggcg ctcctcaccc cttccacttg | 1200 |
| cacggtcacg tcttcgccgt tgtccgcagc gctggcagca ccgtctacaa ctacgacaac | 1260 |
| cccatctggc gcgacgtcgt cagcaccggc accctgcag cgggcgacaa cgtcaccatc | 1320 |
| cgcttccaga ccaacaaccc tggtccctgg ttcctccact gtcacatcga cttccacctc | 1380 |
| gacgccggct tgccgtggt catggctgag gaccctgttg acactccgac ggcggatccc | 1440 |
| gttccccagg cgtggtccga tctctgcccg acatacgacg cgctttccgt cgacgaccag | 1500 |
| tga | 1503 |

<210> SEQ ID NO 19
<211> LENGTH: 1557
<212> TYPE: DNA
<213> ORGANISM: Cerrena sp

<400> SEQUENCE: 19

| | |
|---|---|
| atgcttaact ttaattcgct ttccaccttc gcagtccttg ctttgtcgat gcgcgcaaat | 60 |
| gccgctatcg gtcctgtcac tgacttagaa atcacgaacg gcaccatctc tcccgatggc | 120 |
| tattctcgtg cagccgtcct tgctggaggc tctttccccg gcccacttat cacaggaaac | 180 |
| aaaagtgaca acttccaaat caacgttgtg aactcgttgg ccgattccga catgcttaag | 240 |
| tctacaaccg ttcactggca cggtttcttc caaaagggta ccaactgggc tgacggccct | 300 |
| gctttcgtca accagtgtcc cattgcgacg ggcaactctt tcctttacaa cttcaacgct | 360 |
| acggaccagg ctggtacttt ctggtaccat tctcacttgg agactcagta ctgtgatggt | 420 |
| cttcgtggcc cgatggttgt ctatgaccca acgatcctc atgctgacct ctacgatgtc | 480 |
| gacgacgata gcactgtcat tactcttgcc gattggtatc acacccttgc tcgacttggt | 540 |
| gccgctttcc cgacttcgga cgctactttg atcaacggtt gggccgtta cagcgatggt | 600 |
| aacacaaccg atctcgctgt cattactgtc gaatccggca agaggtaccg attcaggctg | 660 |
| gtcagcattt cttgcgatcc caacttcact ttctccatcg acaaccacac catgacaatc | 720 |
| atcgaggctg atgctgtcaa ctatacaccc ctcgatgttg acgagattca aatcttcgct | 780 |
| ggtcaacgtt actccttcat tctcactgcc aaccagaccg tcgacaacta ctggattcgt | 840 |
| gctgacccca acgttggtac gactggcttc gacaatggca tcaactccgc tatccttcgt | 900 |
| tacagcggtg ccgacgaggt cgagcctacc accaaccaga ccaccagtac taaccctctt | 960 |
| gttgaggcta acttggttcc tctcgatggt gctgctgctc ccggtgaagc tgtcgctgga | 1020 |

```
ggtgttgact atgcgctgaa cttggctctc gctttcgacg gtacaaacct cgatttcacc    1080
gtcaacggtt acgagtacac ctctcctacc gtcccagtcc tactccaaat tctcagcggt    1140
gcctcttccg tcgacgactt gctccccagt ggaagcattt actcactgcc aagcaactcc    1200
actatcgagc tcagtattcc cgcacttgcc gtcggtgctc ccacccctat ccatttgcac    1260
ggtcacactt tctctgtcgt tcgtagtgcc ggatccacca cctacaacta cgacaacccc    1320
cctcgtcgtg acgtcgtcag cattggtacc gccactgatg ataacgttac cattcgtttc    1380
accaccgaca acccgggacc ttggttcctc cactgtcaca ttgacttcca cttggaagct    1440
ggtttcgcag tcgtctttgc tgaagacttt aatgacactg cttctgctaa cactgtcacc    1500
actgaatgga gcgacctctg cactacctac gatgccctct cctccgatga cctctaa      1557
```

<210> SEQ ID NO 20
<211> LENGTH: 1554
<212> TYPE: DNA
<213> ORGANISM: Cerrena sp

<400> SEQUENCE: 20

```
atgattaact ttaattcgtt acttactttc acagtcctag cactgtcgat gcgcgcacat      60
gccgctatcg gtcccgtcac tgacctcaca atcactaatg ccaccatttc cccggatggt     120
ttctctcgtc aagccgtgct tgctggaggt gttttccctg gtccgcttat taccggaaac     180
aagggcgaca acttccaaat caatgttgtt aattcattgg aaaactctga catgcttaag     240
tctacgacca ttcactggca cggttttctt cagaagggta ccaactgggc cgatggtcct     300
gccttcgtta accaatgccc catcgccacg ggcaactctt cctgtacaa cttcaacgca      360 gacgaccagg ctggtacatt ctggtaccac tctcacttgt ctactcaata ttgcgatggt     420
ctccgaggcc ctatggtcgt ctacgacccg aacgatcctc acgcttccct ctacgatgtt     480
gatgatgaga gcactgtgat taccctcgcc gattggtacc acacccttgc ccgacttggt     540
gcagctttcc cgactgcgga tgctacccct attaacggct tgggtcgtta cagcgatggt     600
actacttcgg accttgctgt tatcaccgtt gagtccggaa agaggtaccg attccgattg     660
gtcaacattt cttgcgaccc caactacact ttctctatcg acaaccacac attcaccgtc     720
attgaggtcg atggtgtcaa ccacgcggcg cttgatgtcg atgaaatcca gatcttcgct     780
ggtcaacgtt actcctttgt tctcactgct aaccaaaccg tcgacaacta ctggatccgt     840
gcaaacccca atctcggaac caccggcttc gacaacggca tcaactccgc tatcctccgt     900
tacagcggtg ctaacgagac tgaacccacc accacccaga ccaccgctac tgctgctctc     960
agcgaagcta gctcgttcc tctcgaggac cctgctgctc tggtgaggc cgttgccgga      1020 ggtgtcgatt atgctttgaa cttggcattc gccttgacg tgccaacct tgacttcaca      1080 gtcaacggtg aaacctacgt ctcccctacc gtcccgtcc tcctccaaat tcttagcggt      1140
gcttcctccg tctctgactt gctccctgcc ggaagcgtct actccttgcc cagcaactcc    1200
accatcgagc tcagcatgcc tggaggtgtc gtcggtggtg gtcacccct tcacttgcac     1260 ggtcacgcct tctccgttgt tcgtagtgcc ggctctgaca cttacaacta cgtcaacccc    1320
cctcgccgtg atgttgtcaa cattggtgct gctggtgaca cgtcactat ccgtttcacc     1380 actgacaacc ccgacccctg ttcctccac tgccacatcg atttccactt ggaagctggc     1440
ttcgctgtcg tctttgctga ggacttcaac gccaccgctt cttctaacac cgtcaccact    1500
gagtggagca acctttgcac cacctacgac gccctctctg ccgacgatca gtaa          1554
```

<210> SEQ ID NO 21

<211> LENGTH: 1551
<212> TYPE: DNA
<213> ORGANISM: Cerrena sp

<400> SEQUENCE: 21

```
atggccttcc gaaccgggtt ttccgctttc atctctctca gccttgccct tggtgcactc      60
gctgctatcg gtcctgttgc tgaccttcac atcacggatg cgaacgtttc tcctgatggc     120
ttcactcgac ctgctgtcct tgctggtggc accttcccg gccctctcat tacgggaaag      180
cagggtgaca acttccagat caatgtcatc gacgaactca cggacgcgac tatgttgaag     240
tctacgtcta ttcattggca cggtatcttc agaaaggca ccaactgggc tgacggcccc      300
tccttcgtca atcagtgccc catcactaca ggaaactcgt tcctgtacga cttttctgtc     360
cccgaccaga ccggcacgta ctggtatcac agtcatttat ccacccagta ctgtgacggt     420
ttgcgaggag cccttgtcat ttacgacgac aatgatcctc acaaggatct ctatgatgtt     480
gatgatgaga ctaccgtcat caccctcgcc gactggtatc atacccaggc tcgcctgatc     540
actggtgtcc ctgtctccga tgcgactctg atcaacggtc ttggccgtta tcttaatggc     600
ccaaccgatg ctccgctcgc tgttatcact gtcgaccaag gaaaacgtta tcgtttccgt     660
ctcgtctcta tttcatgcga cccgaacttc gtcttctcca ttgacaacca ttccatgact     720
gtcattgaag tcgatgctgt caacagccag cctctcgtcg tcgactctat tcaaatcttc     780
gcggcacagc gatactcctt cattttgaat gccaaccaaa gtgtcggaaa ctactggatc     840
cgtgccaacc ccaacttggg caacactggt tttacgaatg cattaactc ggccattctt     900
cggtacaatg gtgctcctgt tgctgagccc aacaccaccc aaactgctag caccaacccc     960
ttgaacgagg ttaaccttca ccctctagtt cccacgcccg tccctggtac tcctcagcct    1020
ggcggtgttg atgttgtcca gaaccttgtc ctcggtttca gcggcggcaa gttcactatc    1080
aacggtgttg cctttctctc cccgacggtc ccagttctcc ttcaaatcct tagcggtact    1140
actactgccc aagatcttct tcccactgga tccattatcg agcttcccct cggaaagact    1200
gttgaactta ccctggcagc gggcgttctc ggtggtcccc acccttcca cttgcacggt    1260
cacactttcc acgttgttcg cagcgctggt cagactactc taactacgt cgatcctatt    1320
cttcgtgaca ctgtcaacac cggtgctgct ggcgacaatg ttactatccg tttcaccact    1380
gacaaccctg accctggtt cctccactgc cacattgatt ggcacttgga agccggtttc    1440
gctgttgtct cgctgaagg tcttaaccag accaatgctg ctaacccca tcctgatgct    1500
tggaacaacc tttgcgacct ctacaatgcc cttcctgctg gtgaccagta g            1551
```

<210> SEQ ID NO 22
<211> LENGTH: 1566
<212> TYPE: DNA
<213> ORGANISM: Lentinus sp

<400> SEQUENCE: 22

```
atggccaagt tcagtctttt gctctcctac acccttctct ccctcgtcgc cactgtctat      60
gcaggcatcg gccccattgc tagcctcgtc gtcaccgatg cccagattag ccccgacggc     120
tacttgcgcg atgctatcgt gaccaatggg gtcttcccag ccctctgat cactggacgt      180
aagggtgatc acttccagct gaatgtcgtg gattccatga caaccacac catgctgaaa     240
tccacaagta tccactggca tggcttcttc cagaagggca caaactggg ctgatggtcct     300
gcatttgtga accagtgccc tatttccagc ggccactcgt tcctctacga cttccacgtt    360
ccggaccaag cagggacgtt ctggtaccac agtcacttgt ccactcaata ctgcgacggt    420
```

```
ttgaggggcc cgatggttgt gtacgatccc aacgaccctc atgcaaatct ctacgacatc      480
gataacgaca gcactgtgat aactctcgcc gattggtatc acgtcgcggc caagctcggc      540
cctcgcttcc cacttggggc tgatgctacc cttatcaacg gaaagggcag aagccctgcc      600
actcccacag cagcactgtc cgtcatcaac gtggtcaaag gcaagcggta tcggttccgc      660
ttggtttcaa tctcctgcga cccgaactat gtgttcagca tcgacaacca tacgatgacg      720
gtcatcgagg ccgataccgt gaacacccag cccctcgccg tcgacagcat ccagatcttc      780
gcggcccagc gttactcatt cattctcaac gccaaccagc ccgtcgacaa ctactggatt      840
cgcgccaacc cgaacttcgg gaacgtcgga tttacggatg gcatcaactc tgctatcctc      900
cgttacactg gggcggcact ggtcgaaccg tctgcgacca ccgctccgac actgagcaac      960
cctctcgtcg agacaaacct gcatcctctt gcgcccatgc ctgtgcccgg acaacccgtt     1020
tccggtggtg tcgataaggc tatcaacttc gccttcaact tcgatggcac ggacttcttc     1080
atcaacggcg cgagcttcgt cccacctacg gttccggtcc ttctccaaat catgagcggc     1140
gccagcacgg cgcaggacct ccttccttcc ggcagcgtct acccgcttcc atcaaacgcg     1200
acgatcgagc tctccttccc ggcgaccgcc gctgcgcctg cgcccccca ccccttccac      1260 ttgcacggcc acgtcttcgc cgtcgtccgc agcgcgggaa gcaccaccta caattacaac     1320
aaccccatct ggcgcgatgt cgtcagcact ggcaccctg cagcgggcga caacgtcacc      1380 atccgtttt cgacgaacaa cccgggtccg tggttcctcc actgccacat cgacttccac      1440
ctcgaggcgg gcttcgcagt agtcatggcc gaagacgtcc ccgacattcc gtctgcgaac     1500
cctgtgcccc aggcgtggtc gaacctttgc ccaacttaca acgcgctcag ttctgatgat     1560
cagtaa                                                                 1566

<210> SEQ ID NO 23
<211> LENGTH: 1467
<212> TYPE: DNA
<213> ORGANISM: Lentinus sp

<400> SEQUENCE: 23
atggccaagt tcagtctttt gctctcctac acccttctct ccctcgtcgc cactgtctat       60
gcaggcatcg gccccattgc tagcctcgtc gtcaccgatg cccagattag ccccgacggc      120
tacttgcgcg atgctatcgt gaccaatggg gtcttcccag cccctctgat cactggacgt      180
aagggtgatc acttccagct gaatgtcgtg gattccatga caaaccacac catgctgaaa      240
tccacaagta tccactggca tggcttcttc cagaagggca caactgggc tgatggtcct      300 gcatttgtga accagtgccc tatttccagc ggccactcgt tcctctacga cttccacgtt      360
ccggaccaag cagggacgtt ctggtaccac agtcacttgt ccactcaata ctgcgacggt      420
ttgaggggcc cgatggttgt gtacgatccc aacgaccctc atgcaaatct ctacgacatc      480
gataacgaca gcactgtgat aactctcgcc gattggtatc acgtcgcggc caagctcggc      540
cctcgcttcc cacttggggc tgatgctacc cttatcaacg gaaagggcag aagccctgcc      600
actcccacag cagcactgtc cgtcatcaac gtggtcaaag gcaagcggta tcggttccgc      660
ttggtttcaa tctcctgcga cccgaactat gtgttcagca tcgacaacca tacgatgacg      720
gtcatcgagg ccgataccgt gaacacccag cccctcgccg tcgacagcat ccagatcttc      780
gcggcccagc gttactcatt cattctcaac gccaaccagc ccgtcgacaa ctactggatt      840
cgcgccaacc cgaacttcgg gaacgtcgga tttacggatg gcatcaactc tgctatcctc      900
cgttacactg gggcggcact ggtcgaaccg tctgcgacca ccgctccgac actgagcaac      960
```

| | |
|---|---|
| cctctcgtcg agacaaacct gcatcctctt gcgcccatgc ctgtgcccgg acaacccgtt | 1020 |
| tccggtggtg tcgataaggc tatcaacttc gccttcaact tcgatggcac ggacttcttc | 1080 |
| atcaacggcg cgagcttcgt cccacctacg gttccggtcc ttctccaaat catgagcggc | 1140 |
| gccagcacgg cgcaggacct ccttccttcc ggcagcgtct acccgcttcc atcaaacgcg | 1200 |
| acgatcgagc tctccttccc ggcgaccgcc gctgcgcctg gcgcccccca ccccttccac | 1260 |
| ttgcacggcc acgtcttcgc cgtcgtccgc agcgcgggaa gcaccaccta caattacaac | 1320 |
| aaccccatct ggcgcgatgt cgtcagcact ggcacccctg cagcgggcga caacgtcacc | 1380 |
| atccgttttt cgacgaacaa cccgggtccg tggttcctcc actgccacat cgacttccac | 1440 |
| ctcgaggcgg gcttcgcagt agtctag | 1467 |

<210> SEQ ID NO 24
<211> LENGTH: 1566
<212> TYPE: DNA
<213> ORGANISM: Lentinus sp

<400> SEQUENCE: 24

| | |
|---|---|
| atggccaagt ccagtcgtt gctttcttac actgtcctct ccttcgtcgc ggctgcctat | 60 |
| gctgccatcg gcccagtcgc tgaccttacc atcagcaatg cccaagtcag ccccgacggc | 120 |
| ttcctccgcg atgccgtcgt gaccaacggc ctggtccctg gcccctcat cacgggcaac | 180 |
| aagggcgatc gcttccagtt gaatgtcatt gatcaaatga ccaaccacac gatgttgaag | 240 |
| actacgagca ttcactggca cggcttcttc cagaagggca ccaactgggc tgatggacct | 300 |
| gcgtttgtga accagtgccc cattgccagc ggcaactcct tcctctacga cttccaggtc | 360 |
| cctgaccagg ctggcacctt ctggtatcac agccaccttt cgacccagta ctgcgacggt | 420 |
| ctccgggggc ctctcgttgt gtacgacccc aatgacccac acgctgccct ctatgatatc | 480 |
| gacgatgata acaccgttat tactttgact gactggtacc atactgcggc caggctcgga | 540 |
| cctcgtttcc cgctgggagc agatgccact ctcatcaacg gcctgggccg cagcccagcc | 600 |
| acgccgaccg ccaacctaac tgtcatcaac gttactcagg gcaagcgcta ccgcttccgc | 660 |
| ctcgtgtcga tctcttgcga cccgaactat gtgttcagca tcgacaacca cacgatgagc | 720 |
| gtcattgaga cggacactgt caacactcaa ccgctcacgg tcgatagcat tcagatctac | 780 |
| gccgcccagc gctactcctt tgtgctcacc gccaaccagt ccgtggataa ctactggatc | 840 |
| cgggcaaacc ccaacttcgg taacgtcggc ttcacggatg ctatcaactc ggccatcctc | 900 |
| cgctatgacg gtgctcccga cgctgagccc tccgctacca ctgcaccgac gttgaccaac | 960 |
| ccgctggttg aggcgaacct tcacccgctt gcttcgatgc ccgtgcccgg atccctgtg | 1020 |
| tctggcggtg tggacaaggc cattaacttc gtcttcaact tcaacggcac gaacttctcc | 1080 |
| atcaacaacg cgactttcgt tccgcccacc gttccggtgc tgctccagat catgagcggc | 1140 |
| gccaacaccg cccaagacct cctgccctct ggcagcgtgt acacactccc gtccaacgct | 1200 |
| accattgagc tgtccttccc tgcgacgagc aacgcccccg cgctcctca cccttccac | 1260 |
| ttgcacggtc acgtcttcgc cgttgtccgc agcgctggca gcaccgtcta caactacgac | 1320 |
| aaccccatct ggcgcgacgt cgtcagcacc ggcacccctg cagcgggcga caacgtcacc | 1380 |
| atccgcttcc agaccaacaa ccctggtccg tggttcctcc actgtcacat cgacttccac | 1440 |
| ctcgacgccg gctttgccgt ggtcatggct gaggaccctg ttgacactcc gacggcggat | 1500 |
| cccgttcccc aggcgtggtc cgatctctgc ccgacatacg acgcgctttc cgtcgacgac | 1560 |
| cagtga | 1566 |

```
<210> SEQ ID NO 25
<211> LENGTH: 19
<212> TYPE: DNA
<213> ORGANISM: Artificial sequence
<220> FEATURE:
<223> OTHER INFORMATION: Synthetic primer

<400> SEQUENCE: 25
gtagtcatat gcttgtctc                                              19

<210> SEQ ID NO 26
<211> LENGTH: 19
<212> TYPE: DNA
<213> ORGANISM: Artificial sequence
<220> FEATURE:
<223> OTHER INFORMATION: Synthetic primer

<400> SEQUENCE: 26
ccgcagcttc acctacgga                                              19

<210> SEQ ID NO 27
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or t

<400> SEQUENCE: 27
caytggcayg gnttyttyca                                             20

<210> SEQ ID NO 28
<211> LENGTH: 20
<212> TYPE: DNA
<213> ORGANISM: Artificial sequence
<220> FEATURE:
<223> OTHER INFORMATION: Synthetic primer

<400> SEQUENCE: 28
tgraartcda trtgrcartg                                             20

<210> SEQ ID NO 29
<211> LENGTH: 28
<212> TYPE: DNA
<213> ORGANISM: Artificial sequence
<220> FEATURE:
<223> OTHER INFORMATION: Synthetic primer

<400> SEQUENCE: 29
gcgacgtgat accaatcggc gagagtta                                    28

<210> SEQ ID NO 30
<211> LENGTH: 28
<212> TYPE: DNA
<213> ORGANISM: Artificial sequence
<220> FEATURE:
<223> OTHER INFORMATION: Synthetic primer

<400> SEQUENCE: 30
ccatgctgaa atccacaagt atccactg                                    28

<210> SEQ ID NO 31
<211> LENGTH: 28
<212> TYPE: DNA
```

```
<213> ORGANISM: Artificial sequence
<220> FEATURE:
<223> OTHER INFORMATION: Synthetic primer

<400> SEQUENCE: 31
cctaacctgc gcatcggctt cccccagc                                          28

<210> SEQ ID NO 32
<211> LENGTH: 30
<212> TYPE: DNA
<213> ORGANISM: Artificial sequence
<220> FEATURE:
<223> OTHER INFORMATION: Synthetic primer

<400> SEQUENCE: 32
cgcaaaaacc ctgcgtccgc attacccagc                                        30

<210> SEQ ID NO 33
<211> LENGTH: 25
<212> TYPE: DNA
<213> ORGANISM: Artificial sequence
<220> FEATURE:
<223> OTHER INFORMATION: Synthetic primer

<400> SEQUENCE: 33
ttcgaaacga ggaattccca ccatg                                             25

<210> SEQ ID NO 34
<211> LENGTH: 25
<212> TYPE: DNA
<213> ORGANISM: Artificial sequence
<220> FEATURE:
<223> OTHER INFORMATION: Synthetic primer

<400> SEQUENCE: 34
ttctagatcc tgatcatcag aactg                                             25
```